(12) United States Patent
Meruelo et al.

(10) Patent No.: US 8,114,961 B2
(45) Date of Patent: Feb. 14, 2012

(54) HUMAN LAMININ RECEPTOR CRYSTAL AND USES THEREOF

(76) Inventors: Daniel Meruelo, Scarborough, NY (US); Kelly Victoria Jamieson, New York, NY (US); Stevan Ralph Hubbard, New York, NY (US)

( * ) Notice: Subject to any disclaimer, the term of this patent is extended or adjusted under 35 U.S.C. 154(b) by 344 days.

(21) Appl. No.: 12/181,653

(22) Filed: Jul. 29, 2008

(65) Prior Publication Data

US 2009/0104708 A1    Apr. 23, 2009

Related U.S. Application Data

(60) Provisional application No. 60/981,583, filed on Oct. 22, 2007.

(51) Int. Cl.
*C07K 14/00* (2006.01)
*G01N 31/00* (2006.01)

(52) U.S. Cl. .......................................... 530/350; 436/4

(58) Field of Classification Search ........................ None
See application file for complete search history.

(56) References Cited

PUBLICATIONS

Jamieson et al., "Crystal Structure of the Human Laminin Receptor Precursor", JBC, 2007, 283(6):3002-3005.*
McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol., 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*

* cited by examiner

*Primary Examiner* — Suzanne M Noakes
(74) *Attorney, Agent, or Firm* — Alston & Bird LLP

(57) ABSTRACT

A human laminin receptor crystal is disclosed. Methods are disclosed for using various computer and non-computer means in order to develop models for use in the development of novel therapeutics that block and/or mimic laminin receptor interactions in the setting of, among others, Alzheimer's disease, other neurological disorders, cancer, and viral and bacterial infections.

6 Claims, 3 Drawing Sheets
(2 of 3 Drawing Sheet(s) Filed in Color)

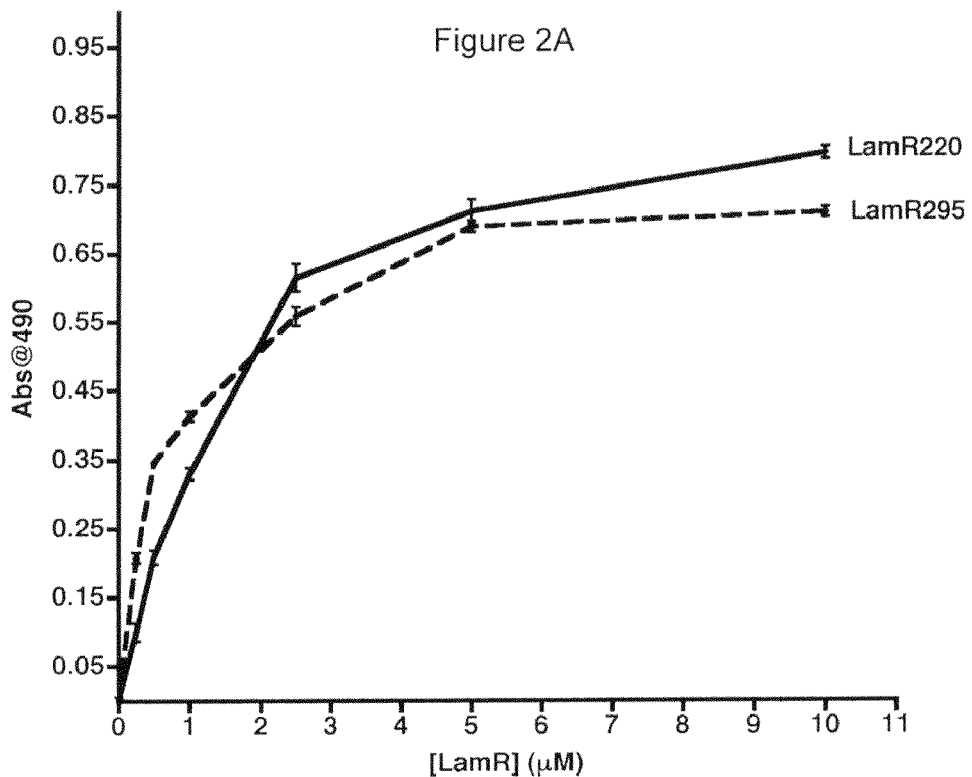
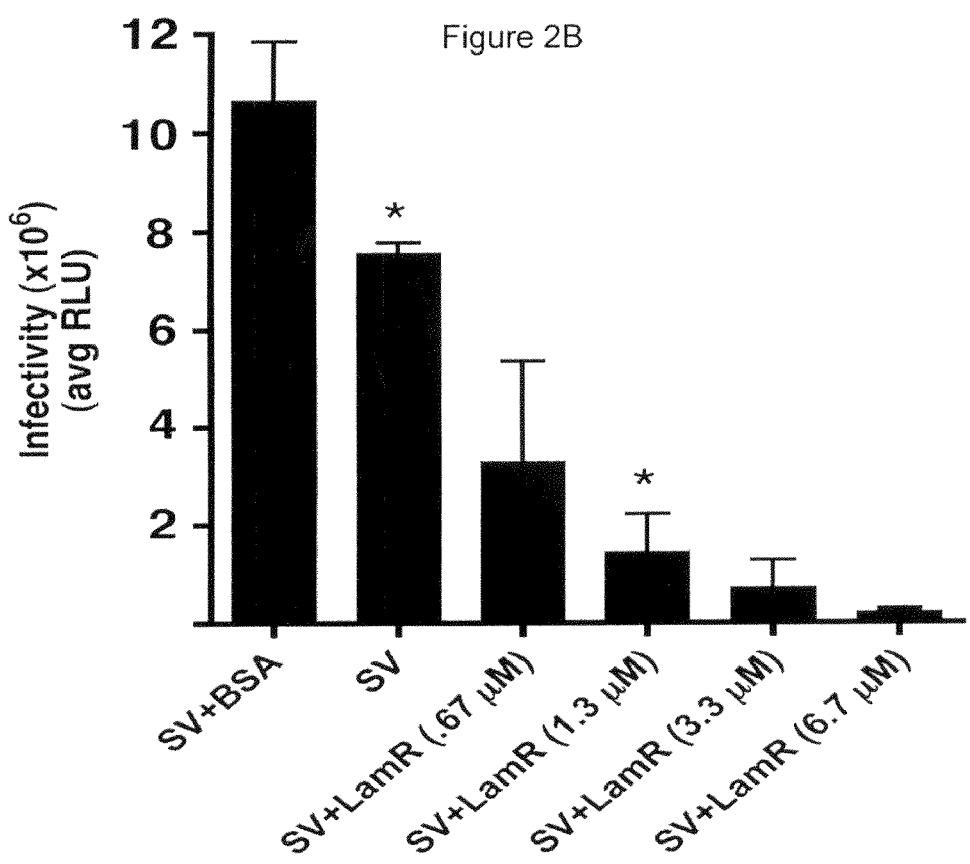

SEQUENCE LISTING

<160> NUMBER OF SEQ ID NOS: 5

<210> SEQ ID NO 1
<211> LENGTH: 220
<212> TYPE: PRT
<213> ORGANISM: Homo sapiens

<400> SEQUENCE: 1

```
Met Ser Gly Ala Leu Asp Val Leu Gln Met Lys Glu Glu Asp Val Leu
 1               5                  10                  15

Lys Phe Leu Ala Ala Gly Thr His Leu Gly Gly Thr Asn Leu Asp Phe
                20                  25                  30

Gln Met Glu Gln Tyr Ile Tyr Lys Arg Lys Ser Asp Gly Ile Tyr Ile
            35                  40                  45

Ile Asn Leu Lys Arg Thr Trp Glu Lys Leu Leu Leu Ala Ala Arg Ala
 50                  55                  60

Ile Val Ala Ile Glu Asn Pro Ala Asp Val Ser Val Ile Ser Ser Arg
 65                  70                  75                  80

Asn Thr Gly Gln Arg Ala Val Leu Lys Phe Ala Ala Ala Thr Gly Ala
                85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
        115                 120                 125

Ala Asp His Gln Pro Leu Thr Glu Ala Ser Tyr Val Asn Leu Pro Thr
130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Glu Lys
    210                 215                 220
```

<210> SEQ ID NO 2
<211> LENGTH: 214
<212> TYPE: PRT
<213> ORGANISM: Caenorhabditis elegans

<400> SEQUENCE: 2

```
Glu Glu Asp Val Met Lys Leu Leu Ala Thr Gln Ala His Leu Gly Ser
 1               5                  10                  15

Thr Asn Leu Asn Phe Gln Met Gln Gln Tyr Val Tyr Lys Arg Arg Phe
```

```
            20                  25                  30
Asp Gly Pro Asn Ile Ile Asn Val Lys Lys Thr Trp Glu Lys Leu Leu
         35                  40                  45

Leu Ala Ala Arg Ala Ile Ala Ala Val Glu Asn Pro Ala Asp Val Val
 50                  55                  60

Val Val Ser Ala Arg Pro Tyr Ala Gln Arg Ala Leu Leu Lys Phe Ala
 65                  70                  75                  80

Ala His Thr Gly Ala Thr Ala Ile Phe Gly Arg Phe Ser Pro Gly Cys
             85                  90                  95

Leu Thr Asn Gln Ile Gln Lys Thr Phe Lys Glu Pro Arg Leu Leu Val
            100                 105                 110

Ile Ser Asp Pro Arg Ile Asp His Gln Ala Val Thr Glu Ala Ser Tyr
            115                 120                 125

Val Gly Val Pro Val Ile Ser Phe Val Asn Thr Glu Ser Pro Leu Lys
            130                 135                 140

Leu Ile Asp Ile Gly Val Pro Cys Asn Asn Lys Gly Glu Arg Ser Ile
145                 150                 155                 160

Gly Leu Met Trp Trp Met Leu Ala Arg Glu Ile Leu Ile Leu Arg Gly
                165                 170                 175

Lys Ile Ser Arg Gln Thr Gly Phe Val Leu Glu Gly Lys Glu Ile Met
            180                 185                 190

Pro Asp Leu Tyr Phe Tyr Arg Asp Pro Thr Glu Thr Lys Glu Glu
            195                 200                 205

Thr Gly Ala His Ala Asp
            210

<210> SEQ ID NO 3
<211> LENGTH: 207
<212> TYPE: PRT
<213> ORGANISM: Saccharomyces cerevisiae

<400> SEQUENCE: 3

Pro Glu Asp Ala Gln Leu Leu Ile Ala Ala Asn Thr His Leu Gly Ala
 1                   5                  10                  15

Arg Asn Val Gln Val His Gln Glu Pro Tyr Val Phe Asn Ala Arg Pro
                 20                  25                  30

Asp Gly Val His Val Ile Asn Val Gly Lys Thr Trp Glu Lys Leu Val
             35                  40                  45

Leu Ala Ala Arg Ile Ile Ala Ala Ile Pro Asn Pro Glu Asp Val Val
 50                  55                  60

Ala Ile Ser Ser Arg Thr Phe Gly Gln Arg Ala Val Leu Lys Phe Ala
 65                  70                  75                  80

Ala His Thr Gly Ala Thr Pro Ile Ala Gly Arg Phe Thr Pro Gly Ser
             85                  90                  95

Phe Thr Asn Tyr Ile Thr Arg Ser Phe Lys Glu Pro Arg Leu Val Ile
            100                 105                 110

Val Thr Asp Pro Arg Ser Asp Ala Gln Ala Ile Lys Glu Ala Ser Tyr
            115                 120                 125

Val Asn Ile Pro Val Ile Ala Leu Thr Asp Leu Asp Ser Pro Ser Glu
            130                 135                 140

Phe Val Asp Val Ala Ile Pro Cys Asn Asn Arg Gly Lys His Ser Ile
145                 150                 155                 160

Gly Leu Ile Trp Tyr Leu Leu Ala Arg Glu Val Leu Arg Leu Arg Gly
                165                 170                 175

Ala Leu Val Asp Arg Thr Gln Pro Trp Ser Ile Met Pro Asp Leu Tyr
```

```
                180                 185                 190
Phe Tyr Arg Asp Pro Glu Glu Val Glu Gln Gln Val Ala Glu Glu
        195                 200                 205

<210> SEQ ID NO 4
<211> LENGTH: 189
<212> TYPE: PRT
<213> ORGANISM: Archaeoglobus fulgidus

<400> SEQUENCE: 4

Leu Val Pro Pro Asp Asp Tyr Leu Ala Ala Gly Val His Ile Gly Thr
 1               5                  10                  15

Gln Ile Lys Thr Gly Asp Met Lys Lys Phe Ile Phe Lys Val Arg Gln
                20                  25                  30

Asp Gly Leu Tyr Val Leu Asp Ile Arg Lys Leu Asp Glu Arg Ile Arg
            35                  40                  45

Val Ala Ala Lys Phe Leu Ser Arg Tyr Glu Pro Ser Lys Ile Leu Leu
        50                  55                  60

Val Ala Ala Arg Gln Tyr Ala His Lys Pro Val Gln Met Phe Ser Lys
 65                 70                  75                  80

Val Val Gly Ser Asp Tyr Ile Val Gly Arg Phe Ile Pro Gly Thr Leu
                85                  90                  95

Thr Asn Pro Met Leu Ser Glu Tyr Arg Glu Pro Glu Val Val Phe Val
            100                 105                 110

Asn Asp Pro Ala Ile Asp Lys Gln Ala Val Ser Glu Ala Thr Ala Val
        115                 120                 125

Gly Ile Pro Val Val Ala Leu Cys Asp Ser Asn Asn Ser Ser Ala Asp
    130                 135                 140

Val Asp Leu Val Ile Pro Thr Asn Asn Lys Gly Arg Arg Ala Leu Ala
145                 150                 155                 160

Ile Val Tyr Trp Leu Leu Ala Arg Glu Ile Ala Lys Ile Arg Gly Gln
                165                 170                 175

Asp Phe Thr Tyr Ser Ile Glu Asp Phe Glu Ala Glu Leu
            180                 185

<210> SEQ ID NO 5
<211> LENGTH: 197
<212> TYPE: PRT
<213> ORGANISM: Homo sapiens

<400> SEQUENCE: 5

Gln Met Lys Glu Glu Asp Val Leu Lys Phe Leu Ala Ala Gly Thr His
 1               5                  10                  15

Leu Gly Gly Thr Asn Leu Asp Phe Gln Met Glu Gln Tyr Ile Tyr Lys
                20                  25                  30

Arg Lys Ser Asp Gly Ile Tyr Ile Ile Asn Leu Lys Arg Thr Trp Glu
            35                  40                  45

Lys Leu Leu Leu Ala Ala Arg Ala Ile Val Ala Ile Glu Asn Pro Ala
        50                  55                  60

Asp Val Ser Val Ile Ser Ser Arg Asn Thr Gly Gln Arg Ala Val Leu
 65                 70                  75                  80

Lys Phe Ala Ala Ala Thr Gly Ala Thr Pro Ile Ala Gly Arg Phe Thr
                85                  90                  95

Pro Gly Thr Phe Thr Asn Gln Ile Gln Ala Ala Phe Arg Glu Pro Arg
            100                 105                 110

Leu Leu Val Val Thr Asp Pro Arg Ala Asp His Gln Pro Leu Thr Glu
        115                 120                 125
```

```
Ala Ser Tyr Val Asn Leu Pro Thr Ile Ala Leu Cys Asn Thr Asp Ser
    130             135             140

Pro Leu Arg Tyr Val Asp Ile Ala Ile Pro Cys Asn Asn Lys Gly Ala
145             150             155             160

His Ser Val Gly Leu Met Trp Trp Met Leu Ala Arg Glu Val Leu Arg
            165             170             175

Met Arg Gly Thr Ile Ser Arg Glu His Pro Trp Glu Val Met Pro Asp
            180             185             190

Leu Tyr Phe Tyr Arg
        195
```

HUMAN LAMININ RECEPTOR CRYSTAL AND USES THEREOF

CROSS-REFERENCE TO RELATED APPLICATION

This application claims the benefit of and priority to U.S. Provisional Application Ser. No. 60/981,583, filed on Oct. 22, 2007, the entirety of this application hereby incorporated by reference.

STATEMENT REGARDING FEDERALLY SUPPORTED RESEARCH OR DEVELOPMENT

This invention was supported, in whole or in part, by U.S. Public Health Service grants CA100687 and CA68498 from the National Cancer Institute, National Institutes of Health, and Department of Health and Human Services. The Government has certain rights in the invention.

FIELD OF THE INVENTION

The present disclosure is directed to the crystal structure of a laminin receptor (hereinafter "LamR"), and furthermore is directed to developing novel therapeutics that block and/or mimic laminin receptor interactions in the setting of, among others, Alzheimer's Disease, other neurological disorders, cancers and viral and bacterial infections.

Throughout this Application, various publications are referenced by the lead author's name and date of publication. Full citations of these publications may be found in the References Cited. The disclosures of these publications are hereby incorporated by reference into this Application in, order to more fully describe the state of the art as of the date of the invention described and claimed herein.

BACKGROUND OF THE INVENTION

The LamR is a nonintegrin cell-surface protein that has been identified as the receptor for, among others, the extracellular matrix molecule laminin-1 (Rao 1983), pathogenic prion protein. (Gauczynski 2001), Sindbis virus (Wang 1992), Venezuelan equine encephalitis virus (VEE) (Ludwig 1996), cytotoxic necrotizing factor type I and II (McNichol 2007), and Adeno-associated virus serotypes 2, 3, 8 and 9 (Akache 2006). LamR binds to laminin with high affinity, mediating interactions between laminin and the extracellular environment that affect cell adhesion, tumor growth and metastasis.

Two types of LamR, the 67 kDa and the 37 kDa, are found on the surface of cells (Gauczynski 2001.). The 67 kDa laminin receptor may be formed by the dimerization of the 37 kDa laminin receptor. Phylogenetic analysis also suggests that the LamR is a ribosomal protein that acquired the additional novel function of the laminin receptor during evolution (Ardini 1998).

Structural characterization of the LamR may permit greater understanding of how the LamR interacts with its binding partners. This in turn may facilitate development of therapeutics that may block and/or mimic LamR interactions in the setting of, among others, AD, other neurological disorders, cancer, and viral and bacterial infections.

In addition, structural analysis of the LamR may provide insight into the development of therapeutics that aid in the prevention of various disease states, including tumor growth and metastasis.

Because of the role of LamR interaction, with laminin in normal and cancerous cells, as well as its role as a receptor for Sindbis virus, adeno-associated virus and pathogenic prion protein, it is desirable to study LamR using crystallographic methods.

SUMMARY OF THE INVENTION

The present disclosure provides a crystalline form of a human LamR, and provides methods for developing novel therapeutics that block and/or mimic LamR interactions in the setting of, among others, AD, other neurological disorders, cancer, and viral and bacterial infections.

According to aspects illustrated herein, a crystal is provided that includes at least a portion of a LamR. The term "at least, a portion" refers to a LamR having some or all residues of a LamR protein. In some aspects, the term "at least a portion" refers to a LamR having residues 1-220 of a full-length LamR.

According to aspects illustrated herein, a method is disclosed for identifying an agent that interacts with a LamR, that includes: providing at least a portion of the LamR as a crystal; and employing computational analysis to design or select an agent that interacts with the crystal.

According to further aspects illustrated herein, a method is disclosed for identifying an agent that interacts with a LamR that includes: providing at least a portion of the LamR as a crystal; generating a three-dimensional model of the crystal using a set of relative structural coordinates according to Appendix 1 with a root mean square deviation from residue backbone atoms being not more than 1.5 Å, the set of relative structural coordinates being based on the crystal; and employing the three-dimensional model to design or select an agent that interacts with the crystal.

According to further aspects illustrated herein, there is disclosed a method for identifying an activator or inhibitor of a molecule or molecular complex having an active binding site that includes: generating a three dimensional representation of the molecule or molecular complex including an active binding site using a set of relative structural coordinates of amino acid residues Leu25, Gly26, Gly27, Ile46, Arg80, Asp126, Arg128, Asn149, Asp151, Ser152, Asp164, Asp165, Lys166, Gln33, Gln35, Tyr36, Lys57, Ala137, Ser138, Asn141, Leu142, Pro143, Thr144, Met10, Leu19, His24, Ile49, Asn50, Leu51, Lys52, Gln9, Lys11, Trp55, Leu59, Glu181, Arg184, Met185 Arg191, Thr28, Ile46, Pro127, Ala129, Val15, Phe18, Leu25, Arg80 and Asn81, or any portion thereof, with a root mean square deviation from residue backbone atoms of the amino acid residues being not more than 1.5 Å; and selecting or designing a candidate activator or inhibitor by performing computer fitting analysis of the candidate activator or inhibitor with the three dimensional representation generated.

According to further aspects illustrated herein, there is disclosed a method for identifying a potential compound able to interact with a LamR family member that includes: selecting or designing the potential compound by performing rational drug design with a computer readable data storage material encoded with computer readable data including structure coordinates as listed in Appendix 1, wherein the selecting or designing is performed in conjunction with computer modeling; contacting the potential compound with at least a portion of a LamR; and detecting an ability of the potential compound to interact with the LamR family member.

According to yet further aspects illustrated herein, methods of identifying an agent that interacts with LamR, and/or identifying an activator or inhibitor of a molecule or molecular complex having an active binding site, and/or identifying a potential compound that is able to interact with a LamR family member may also be performed without the aid of a computer means. Indeed, the present invention includes manual and computational methods of determining and/or deriving the above, in accordance with a crystal of at least a portion of the LamR being provided.

According to even further aspects illustrated herein, there is disclosed a crystal that includes at least a portion of a p40 ribosomal protein, wherein the p40 ribosomal protein is in tetragonal space group P4$_3$2$_1$2 and has unit cell dimensions a=75.7 Å, b=75.7 Å, and c=99 Å.

Applicants have also found that LamR interacts with many ligands including, but not limited to, laminin, prions, Sindbis virus, and EGCG (the major polyphenol in green tea).

LamR may also be implicated in the onset of Alzheimer's Disease (hereinafter "AD") and certain dancers.

With respect to cancer, it has been observed that one of the ways EGCG may mediate anticancer effects is through binding to the LamR. Applicants have found that the Sindbis vector targets overexpressed LamR on tumor cells, resulting in the reduction of tumor load. Thus, targeted therapeutic design with respect to the LamR's interaction with its other binding partners will be efficacious.

For example, Applicants have discovered that blocking the interaction of certain ligands with the LamR will prevent internalization of a pathogen. This blocking prevents the removal of LamR from the cell surface. Together, these actions may very well effect disease progression.

With respect to AD, laminin has been shown to interact with the amyloid beta 1-40 peptide (hereinafter "Aβ"), thus blocking fibril formation and even inducing depolymerization of pre-formed fibrils. LamR may be of therapeutic interest for controlling the amyloidosis that occurs with AD.

Targeted therapeutic design against LamR's interaction with its other binding partners may also be efficacious. Further study of the structure of the LamR crystal provided herein will contribute to an understanding of how LamR interacts with its binding partners and aid in the development of therapeutics that can block and/or mimic LamR interactions in the setting of, among others, AD, other neurological disorders, cancers and viral and bacterial infections.

In addition, study of the LamR crystal structure may also lead to discovery of co-crystals representing the crystal forms and structures of the LamR when interacting with binding partners, which may further aid in the prevention or treatment of the types conditions noted above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The presently disclosed embodiments will be further explained with reference to the attached drawings, wherein like structures are referred to by like numerals throughout the several views. The drawings are not necessarily to scale, the emphasis having instead been generally placed upon illustrating the principles of the presently disclosed embodiments.

FIGS. 2A and 2B show the bioactivity of LamR-220 of the presently disclosed embodiments, in vitro. FIG. 2A shows the in vitro LamR-220 binding affinity for laminin-1. (LamR-220 is illustrated by a solid black line and LamR-295 is illustrated by a dashed black line. n=3±SEM.) LamR-220 K$_d$=1.7 µM. LamR-295 K$_d$=0.7 µM. FIG. 2B shows Sindbis viral vector infection inhibition by LamR-220 in baby hamster kidney (hereinafter "BHK") cells, SV=Sindbis vector (MOI=100), LamR=recombinant LamR-220. n=2±SEM. Statistical significance was calculated by a two-tailed student t-test (P<0.05).

FIGS. 3A, 3B-1, 3B-2 and, 3C show the crystal structure of human LamR-220 of the presently disclosed embodiments. FIG. 3A shows a ribbon diagram of LamR-220 with α helices labeled "A", "B", "C", "D" and "E" and β strands, labeled "1", "2", "3", "4", "5", "6" and "7". FIGS. 3B-1 and 3B-2 show the superimposition of LamR-220 and *A. fulgidus* S2p (1VI6). Regions of divergence between the two structures are at residues 111-118 and 188-196.

Figure 1:
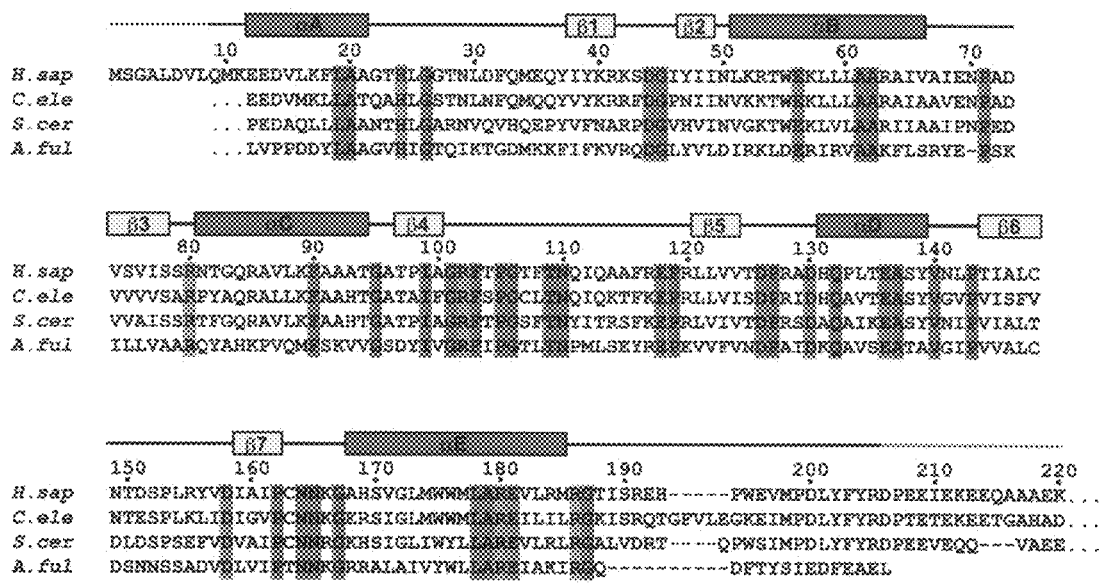
FIG. 1 shows the sequence homology between the 37LRP/p40 orthologs and the *H. sapien* LamR-220 of the presently disclosed embodiments. Orthologs are *C. elegans* SA ribosomal protein (p40), *S. cerevisiae* S2p ribosomal protein, and *A. fulgidus* S2p ribosomal protein. Residue numbering is for human LamR-220.

While the above-identified drawings set forth presently disclosed embodiments, other embodiments are also contemplated, as noted in the discussion.

DETAILED DESCRIPTION OF THE INVENTION

As noted above, the embodiments disclosed herein relate to the three dimensional crystal structure of a LamR and to developing novel therapeutics that may block and/or mimic LamR interactions in the setting of, among others, AD, other neurological disorders, cancer, and viral and bacterial infections.

Atomic structural coordinates for the LamR of the presently disclosed embodiments were derived from the analysis of high resolution X-ray diffraction patterns of crystals of a 220-residue version LamR (hereinafter sometimes referred to as "LamR-220"). These atomic structural coordinates are given in Appendix 1.

Definitions

All scientific terms are given their ordinary meanings as understood by those of skill in the art, unless an alternate meaning is set forth below.

As used herein, the term "LamR" refers to the laminin receptor.

As used herein, the term "p40" refers to the p40 ribosome-associated protein.

As used herein, the term "molecular replacement" means a method of solving crystal structure using a set of atomic coordinates of a structurally related molecule.

As used herein, the term "binding site" or "binding pocket" refers to a region of a protein or protein/RNA complex or RNA that binds or interacts with a particular compound.

As used herein, the term "structural coordinates" refers to mathematical Cartesian coordinates corresponding to an atom's spatial relationship to other atoms in a molecule or molecular complex. Structural coordinates may be obtained using x-ray crystallography techniques or NMR techniques, or may be derived from mathematical equations related to the X-ray diffraction patterns obtained by diffracting X-rays off a crystal. The diffraction data are used to calculate an electron density map of the unit cell comprising the crystal; said maps are used to establish the positions of the atoms (e.g., the structure coordinates) within the unit cell. Various software programs allow for the graphical representation of a set of structural coordinates to obtain a three dimensional representation of a molecule or molecular complex. Those of skill in the art understand that a set of structure coordinates determined by X-ray crystallography contains standard errors.

As used herein, the term "β sheet" refers to two or more polypeptide chains (or beta strands) that run alongside each other and are linked in a regular manner by hydrogen bonds between the main chain C=O and N—H groups. Therefore all hydrogen bonds in a beta-sheet are between different segments of polypeptide. Most β-sheets in proteins are all-parallel (protein interiors) or all-antiparallel (one side facing solvent, the other facing the hydrophobic core). Hydrogen bonds in antiparallel sheets are perpendicular to the chain direction and spaced evenly as pairs between strands. Hydrogen bonds in parallel sheets are slanted with respect to the chains direction and spaced evenly between strands.

As used herein, the term "α helix" refers to the most abundant helical conformation found in globular proteins. The average length of an α helix is 10 residues. In, an α helix, all amide protons point toward the N-terminus and all carbonyl oxygens point toward the C-terminus. The repeating nature of the phi/psi pairs ensure this orientation. Hydrogen bonds within an α helix also display a repeating pattern in which the backbone C=O of residue X (wherein X refers to any amino acid) hydrogen bonds to the backbone HN of residue X+4. The α helix is a coiled structure characterized by 3.6. residues per turn, and translating along, its axis 1.5 Å per amino acid. Thus the pitch is 3.6×1.5 or 5.4 Å. The screw sense of alpha helices is always right-handed.

As used herein, the term "loop" refers to any other conformation of amino acids (i.e. not a helix, strand or sheet). Additionally, a loop may contain bond interactions between amino acid side chains, but not in a repetitive, regular fashion.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

As used herein, the term "root mean square deviation" is the square root of the arithmetic mean of the squares of the deviations from the mean, and is a way of expressing deviation or variation from the structural coordinates described herein. The present disclosure includes all embodiments comprising conservative substitutions of the noted amino acid residues resulting in same structural coordinates within the stated root mean square deviation.

As used herein, an "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound or drug) via various covalent and/or non-covalent binding forces. An active site in accordance with the present disclosure may include, for example, the actual site of substrate binding with laminin receptor, as well as accessory binding sites adjacent or proximal to the actual binding site of substrate binding that nonetheless may affect laminin receptor activity upon interaction or association with a particular agent, either by direct interference with the actual site of substrate binding or by indirectly affecting the steric conformation or charge potential of the laminin receptor and thereby preventing or reducing binding of substrate to the laminin receptor at the actual site of substrate binding.

As used herein, an "agent" includes a protein, polypeptide, peptide, nucleic acid (including DNA or RNA), molecule, compound or drug.

As used herein, the terms "a target structural motif" or "target motif" refer to any rationally selected sequence or combination of sequences in which the sequence(s) are chosen based on a three-dimensional configuration or electron density map which is formed upon the folding of the target motif. There are a variety of target motifs known in the art. Protein target motifs include, but are not limited to, enzymatic active sites, structural subdomains, epitopes, functional domains and signal sequences.

Structural similarity may be inferred from, e.g., sequence similarity, which can be determined by one of ordinary skill through visual inspection and comparison of the sequences, or through the use of well-known alignment software programs such as CLUSTAL (Wilbur, W. J. and Lipman, D. J. Proc. Natl. Acad. Sci. USA, 80, 726 730 (1983)) or CLUSTAL W (Thompson, J. D., Higgins, D. G. and Gibson, T. J., CLUSTAL W: improving the sensitivity of progressive multiple sequence alignment through sequence weighting, positions-specific gap penalties and weight matrix choice, Nucleic Acids Research, 22:4.673 4680 (1994)) or BLAST® (Altschul S F, Gish W, et al., J. Mol. Biol., October 5; 215(3): 403 10 (1990)), a set of similarity search programs designed to explore all of the available sequence databases regardless of whether the query is protein or DNA. A residue within a first protein or nucleic acid sequence corresponds to a residue within a second protein, or nucleic acid sequence if the two residues occupy the same position when the first and second sequences are aligned.

LamR Binding Domains and Experimental Details

The region of LamR responsible for binding laminin-1 is between amino acid residues 161 and 180, and was found using a synthetic peptide called peptide G which corresponds to those amino acids. Specifically, the domain within laminin-1, the Tyr-Ile-Gly-Ser-Arg (YIGSR) peptide, is responsible for binding with LamR. In additions peptide G treatment of cells has been shown to increase and stabilize laminin binding on tumor cells. Peptide. G has also been shown to bind heparin sulfate proteoglycans (hereinafter "HSPG") and it has been suggested that laminin-1 interactions with LamR may also be mediated by HSPG binding.

Another synthetic peptide comprised of corresponding amino acid residues 205-229 of the LamR, has been shown to interact with both laminin-1 and heparin sulfate. This indicates that two sites play a role in LamR interactions with laminin. The interaction domains between LamR and prion protein have also been characterized. Yeast two-hybrid system and cell-binding assays suggest that LamR, contains a primary prion protein-binding region between amino acids 144 and 179 and a secondary indirect binding site that is HSPG-dependent between amino acids 161 and 179.

A potential region for interaction between LamR and Sindbis virus E2 has been identified to lie within the C-terminus of LamR. In fact, Wang et al. determined that binding of monoclonal antibody 1C3 (MAb 1C3) to LamR in culture cells blocked Sindbis virus attachment (Wang 1992). MAb1C3 is a monoclonal antibody that is reactive with an epitope within the C-terminal 48 amino acids (residues 248 to 295) of the LamR. This indicates that Sindbis virus also binds somewhere in this C-terminal domain of LamR.

According to Applicants and others, these data also implicate LamR as the major cell-surface receptor for Sindbis virus in vertebrate cells, but the specific interaction domain between Sindbis virus E2 was heretofore unclear. Thus, X-ray crystallographic studies of the LamR are critical to understanding the precise structure of the LamR and to characterizing the LamR binding interaction with Sindbis virus, as well and other key binding partners and agents.

Discussion

In accordance with the present disclosure, a crystal form of the LamR has been produced. The LamR crystal has structure: and properties described in further detail below.

Thus, the presently disclosed embodiments describe the resolution of a three dimensional crystal structure of a 220-residue version of human LamR precursor protein (hereinafter "LamR-220"). LamR-220 binds laminin-1 in vitro, as shown in FIG. 2A, and inhibits Sindbis virus vector infection of BHK cells, as shown in FIG. 2B. These data demonstrate that the first 220 residues of LamR are sufficient for interacting with key binding partners, including Sindbis virus.

Crystals of LamR-220 were obtained at a pH 6.0 and belong to the tetragonal space group $P4_32_12$ with one monomer in the asymmetric unit. The crystal structure of LamR-220 was determined by molecular replacement, using the crystal structure of the 30S ribosomal protein. S2p from *Archaeoglobus fulgidus* (PDB code 1VI6) (Badger 2005). Data collection and refinement statistics at 2.15 Å resolution are given in Appendix 1 and Table 1 below.

TABLE 1

| | LamR220 |
|---|---|
| Data collection | |
| | |
| Space group | $P4_32_12$ |
| Cell dimensions | |
| | |
| a, b, c (Å) | 75.66, 75.66, 98.965 |
| a, b, g (°) | 90.00, 90.00, 90.00 |
| Resolution (Å) | 50.0 (2.15)* |
| $R_{sym}$ or $R_{merge}$ (%) | 14.4 (47.7) |
| I/sI | 5.0 (4.0) |
| Completeness (%) | 100 (100) |
| Redundancy | 9.4 (9.7) |
| Refinement | |
| | |
| Resolution (Å) | 30.0-2.15 |
| No. reflections | 14762 |
| $R_{work}/R_{free}$ (%) | 18.8/24.1 |
| No. atoms | 1727 |
| Protein | 1563 |
| Ligand/ion | 0 |
| Water | 164 |
| Average B-factor | 22.0 |
| R.m.s. deviations | |
| | |
| Bond lengths (Å) | 0.009 |
| Bond angles (°) | 1.17 |

*Values in parentheses are for highest-resolution shell (2.25-2.15 Å). One crystal was used for data collection.

Figure 3A:
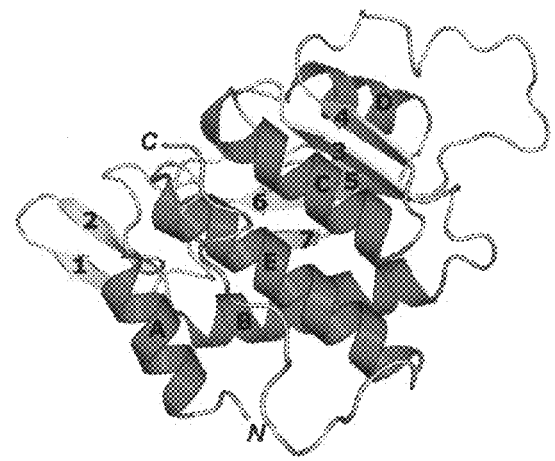

Consistent with a sequence identity of 32% between the LamR and *A. fulgidus* S2p (residues 15-183 of FIG. 1), the two proteins share a similar overall architecture, classified (SCOP) as an α/β protein with a flavodoxin-like fold (see FIG. 3A). A central β sheet composed of five parallel β strands (β3-β7) is flanked by three α helices on one side (αB, αC and αE) and a single α helix (αD) on the other side. An N-terminal α helix (αA) and two anti-parallel β strands (β1-β2) pack against the α/β core of the protein. Residues 1-8 and 206-220 of LamR-220 are disordered in the structure.

Figures 1, 3B:
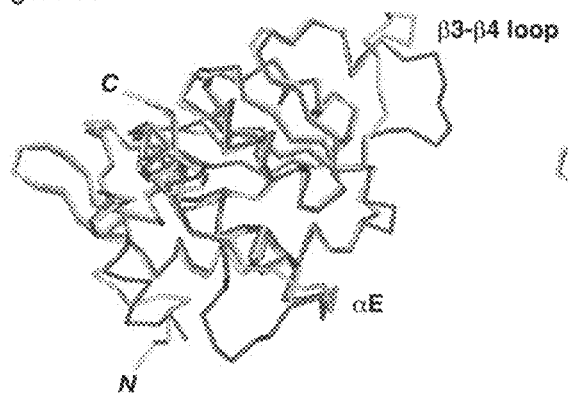
Figures 2, 3B:
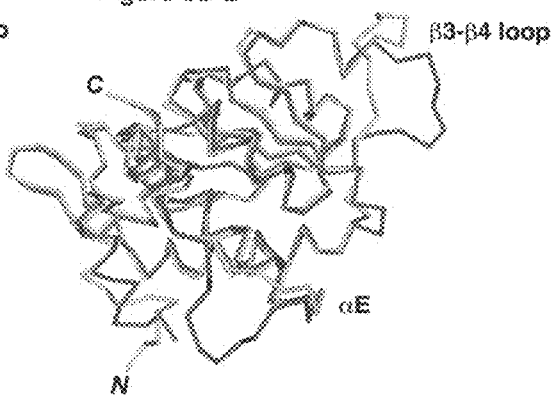
Figure 3C:
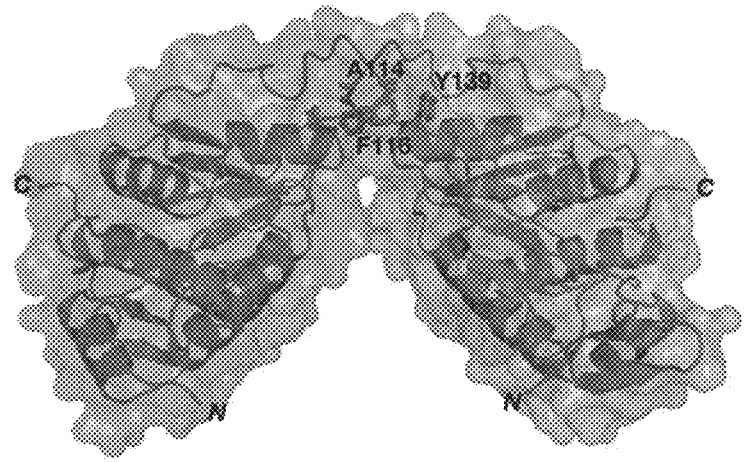
FIG. 3C shows a LamR-220 dimer. Residues in the dimer interface are labeled. The crystallographic two-fold axis is vertical.

FIGS. 3B-1 and 3B-2 show that the superimposition of the structures of LamR-220 and *A. fulgidus* S2p yields a root-mean-square deviation in Cα positions of just 0.9 Å (174 atoms) and reveals two areas in which the structures are divergent. The structures diverge at a segment between β4 and β5 (residues 111-118 in LamR) and a segment after the last α helix (αE) (residues 188-196 in LamR) in which LamR contains a five-residue insertion relative to *A. fulgidis* S2p. The segment between β4 and β5, contains an equal number of residues, in the two proteins. In *A. fulgidis* S2p, the segment is stabilized in a folded-back conformation via a salt bridge between Arg113 in this segment (Arg117 in LamR) and Asp93 (β4), the latter of which is not conserved in LamR, (Thr97). As shown in FIG. 3C, in the LamR-220 structure, this segment instead projects away from, the domain and packs against the same segment in a symmetry-related (two-fold) molecule. In this crystallographic dimer, Ala114 packs into a tight pocket in the symmetry related molecule formed by the β4-β5 segment and the end of αD, and Phe116 is in van der Waals contact with Tyr139 (αD). While Phe116 is generally conserved from *S. cerevisiae* through vertebrate species, Ala114 is conserved only in vertebrates. The total surface area buried in this interface is a modest 832 Å$^2$ and LamR-220 runs as a monomer in solution but, in the context of a membrane attachment and a possible covalent dimerization linkage (Landowski 1995), this crystallographic dimer could be functionally significant.

The structural differences noted between LamR-220 and *A. fulgidis* S2p could be important for ribosomal protein function or the acquired function as the receptor for laminin. Analysis of the 3.0 Å-resolution structure of the 30S ribosomal subunit from *Thermus thermophilus* (PDB code 1J5E) (Wimberly 2000) indicates that the two major structural deviations between human LamR-220 and *A. fulgidis* S2p (between β4 and β5 and after αE) would not appear to affect ribosomal function, since no RNA or protein contacts are present in these regions. This suggests that the structural differences in human LamR versus *A. fulgidis* S2p are important for laminin binding.

Previously, peptide segments of LamR, utilized in binding assays implicated a segment, residues 161-180, known as peptide G, as a binding epitope for laminin. (Castronovo 1991). In the LamR-220 crystal structure of the presently disclosed embodiments, this stretch of residues comprises the linker between β7 and most of αE. The only portion of this sequence that, is solvent accessible are residues 165-169 in the β7-αE linker. Without being limited to any particular theory, it is conceivable that the C-terminal tail of LamR-220 undergoes a conformational change, exposing residues within this segment. It is desirable to determine if other peptide segments of LamR are possible for use in binding assays as a binding epitope for laminin. Previously, a short putative transmembrane segment, residues 86-102 was suggested as a binding epitope for laminin (Castronovo 1991). However, analysis of the LamR-220 of the presently disclosed embodiments shows that this segment, encompassing β4 and most of αC, is an integral part of the protein fold and is unlikely to serve as a transmembrane helix.

In addition, the presently disclosed embodiments permit the use of molecular design techniques (whether utilizing a computer or not) to design, identify and synthesize chemical entities and compounds, including inhibitory compounds, capable of binding anywhere on the LamR and/or LamR-related proteins. As such, the structure of the disclosed LamR crystal may be used to identify potential LamR ligands.

Appendix 1 shows the atomic coordinates/x-ray diffraction data of the LamR-220 of the presently disclosed embodiments. The atomic coordinates/x-ray diffraction data may be used to create a physical three-dimensional model which can then be used to design molecular models of compounds that interact and/or bind with LamR.

Alternatively, the atomic coordinates/x-ray diffraction data may be represented as atomic model output data on computer readable media which is then used in a computer modeling system to calculate different molecules expected to interact and/or bind with the LamR. For example, computer analysis of the data permits calculation of the three-dimensional interaction of the LamR and a ligand to confirm that the ligand binds to, or changes the conformation of, particular domain(s) or subdomain(s) of the LamR. Ligands identified from the analysis of the physical or computer model are then synthesized and tested for biological activity with an appropriate screen.

Although various computer programs are described herein which may be used in conjunction with the present invention, one of skill in the art could of course perform all of the analysis described herein using manual computational methods after having been provided the crystal structure of the LamR. Thus, the practice of the present invention is not limited to using only computer means, but includes and encompasses all forms of computational methods (computers or otherwise).

When using a computer means, however, the atomic coordinates/x-ray diffraction data of the presently disclosed embodiments are generally provided on computer readable media. A skilled artisan is able to access the data and analyze it for structure determination and/or rational ligand (e.g., inhibitor) design using a computer based system.

A typical computer system includes hardware means, software means, and data storage means. The hardware means typically includes a central processing unit (CPU), input means, output means and data storage means. One skilled in the art will readily appreciate which of the currently available computer-based systems are suitable for use in the practice of the presently disclosed embodiments.

As has been disclosed in U.S. patent application Ser. No. 10/885,190, a variety of commercially available software programs are available for conducting the analysis and comparison of data in the computer-based system. One skilled in the art will readily recognize which of the available algorithms or implementing software packages for conducting computer analyses can be utilized or adapted for use in the computer-based system. A variety of structural formats for the input and output means can be used to input and output the information in the computer-based systems of the presently disclosed embodiments.

As has also been disclosed, in U.S. patent application Ser. No. 10/885,190, a variety of comparing means can be used to compare a target sequence or target motif with the data storage means to identify structural motifs or interpret electron density maps derived in part from the atomic coordinates/x-ray diffraction data. One skilled in the art can readily recognize any one of the publicly available computer modeling programs that can be used.

As has been further disclosed in U.S. patent application Ser. No. 10/885,190, suitable software that can be used to view, analyze, design, and/or model a protein include Alchemy™, LabVision™, Sybyl™, Molcadd™, Leapfrog™, Matchmaker™, Genefold™ and Sitel™ (available from Tripos Inc., St. Louis, Mo.); Quanta™, Cerius2™, X-Plor™, CNS™, Catalyst™, Modeller™, ChemX™, Ludi™, Insight™, Discover™, Cameleon™ and Iditis™ (available from Accelrys Inc., Princeton, N.J.); Rasmol™ (available from Glaxo Research and Development; Greenford, Middlesex, U.K.); MOE™ (available from Chemical Computing Group, Montreal, Quebec, Canada); Maestro™ (available from Schrodinger Inc.); Midas/MidasPlus™ (available from UCSF, San Francisco, Calif.); VRML (web-viewer—freeware on, the internet); Chime (MDL—freeware on the internet); MOIL, (available from University of Illinois, Urbana-Champaign, Ill.); MacroModel™ and GRASP™ (available: from Columbia University, New York, N.Y.); Ribbon™ (available from University of Alabama, Tuscaloosa, Ala.); NAOMI™ (available from Oxford University, Oxford, UK); Explorer Eyechem™ (available from Silicon Graphics Inc., Mountain View, Calif.); Univision™ (available from Cray Research Inc., Seattle Wash.); Molscript™ and O (available from Uppsala University, Uppsala, Sweden); Chem 3D™ and Protein Expert™ (available from Cambridge Scientific); Chain™ (available from Baylor College of Medicine, Houston, Tex.); Spartan™, MacSpartan™ and Titan™ (available from Wavefunction Inc., Irvine, Calif.); VMD™ (available from U. Illinois/Beckman Institute); Sculpt™ (available from Interactive Simulations, Inc., Portland, Oreg.); Procheck™ (available from Brookhaven National Laboratory, Upton, N.Y.); DGEOM (available from QCPE—Quantum Chemistry Program Exchange, Indiana University Bloomington, Ind.); RE_VIEW (available from Brunel University, London, UK); Xmol (available from Minnesota Supercomputing Center, University of Minnesota, Minneapolis, Minn.); Hyperchem™ (Available from Hypercube, Inc., Gainesville, Fla.); MDM Display (available from University of Washington, Seattle, Wash.); PKB (available from National Center for Biotechnblogy Information, NIH, Bethesda, Md.); Molecular Discovery Programmes (available from Molecular Discovery Limited, Mayfair, London); Grownol™ (available from Thistlesoft, Morris Township, N.J.); MICE (available from the San Diego Supercomputer Center, La Jolla, Calif.); Yummie and MCPro (available from Yale University, New Haven, Conn.); and upgraded versions thereof.

Another example of the type of software that a skilled artisan may use with the crystal structure of the LamR is software developed by Molsoft Technologies. Specifically, ICM Pro, ICM Browser Pro, ICM Homology and ICM VLS (hereinafter, collectively, "ICM") together provide a solution for the viewing, analysis, modeling, design, and bonding simulation of proteins. ICM enables the analysis of a protein structure including, but not limited to, flagging problem regions, superimposing multiple structures, drug binding pocket and protein-protein interaction prediction, analysis of protein-ligand interactions, protein flexibility, distances and electrostatic properties. ICM also allows the full evaluation of the underlying crystallographic information contained within a Protein Databank file. One such function exhibits the full bio-molecular unit to see if crystal-crystal contacts have influenced the crystal structure. ICM's crystallographic capabilities include, but are not limited to: displaying the crystallographic cell, generating crystallographic neighbors, constructing biological units and applying transformations, and contouring and converting the electron density map to a grid energy map. ICM provides access to the chemical information and tools for accurate individual ligand-protein docking, peptide-protein docking and protein-protein docking, enabling rapid and accurate docking simulations. These tools provide scripting for small scale flexible ligand docking, procedures for protein-protein, and flexible peptide-receptor docking, and refinement of docking solutions in full atom representation. It also allows for the browsing of docking solutions, binding site analysis, visualization of grid potentials, adjustment of grid potential areas, and configurable preferences for ligand size and score thresholds. In application, ICM indexes and converts any chemical database to 3D, then docks and scores all molecules by estimated binding affinity. It separates binders and non-binders, and eliminates at least 99% of compounds that do not fit the protein or ligand pocket, and do not require experimental testing. One skilled in the art will appreciate that ICM (or similar software) may be used in order to determine what compounds can readily interact with the LamR.

Although the present invention is not limited to solely utilizing computers, computer simulation techniques may be advantageously used in connection with the. LamR crystal structure. In particular, the crystal structure of the LamR provides a means of discovering the characteristics and affinities of individual binding sites on the LamR. For example, EGCG is one such high-affinity compound whose specific binding sites with the LamR may be determined. Thus, the presently disclosed embodiments provide a means of accurately testing the effects of many molecular compounds on a given binding site which, in turn, may be used for the discovery and development of therapies for, but not limited to, cancer and AD. In addition, computer and/or other computational models may also be used for the discovery of inhibitors of LamR activity identified or designed by the methods of the presently disclosed embodiments. Once a potential ligand is identified from the analysis described above, the ligand can then be synthesized and tested for biological activity using an appropriate screening method discussed above and claimed below.

Analysis of the LamR crystal structure may also provide insights that aid in the development of novel therapeutics. In cancer, for example, the specific inhibition of the LamR function at the cell surface of tumor cells—either by binding of the catechin EGCG, which most likely competes with endogenous laminin, or by infection with Sindbis virus vector, which is internalized by receptor-mediated endocytosis—has been associated with anti-tumor effects (Tanaka 2000; Tachibana 2004; Tseng 2004; Cao 1999). Thus, both EGCG and Sindbis virus vectors, through two different mechanisms, reduce the ability of the LamR at the surface to interact with laminin.

Cancer cells invade the basement membranes through a process involving the binding of cell surface receptors like the LamR to laminin. While the presence of cancer invariably yields the overexpression of LamR, the expression of LamR has been particularly identified as correlating directly with increased invasiveness and the metastatic potential of tumors (Menard 1998). However, peptide G, for instance, has been identified as interfering with the binding of the LamR to laminin and therefore as effective in inhibiting tumor cell invasion. Similarly, as noted above, EGCG is well known to bind with the LamR, thereby precluding other binding from occurring. Study of the crystal structure of the LamR may permit precise determination of how these bindings occur.

Likewise, the crystal LamR may be used to further understand the role of the LamR in AD. With respect to AD, as previously noted, laminin has been shown to interact with the Aβ, thus blocking fibril formation and even inducing depolymerization of pre-formed fibrils. LamR may also be of therapeutic interest for controlling the amyloidosis that occurs with AD.

By way of a further background, AD is a progressive neurodegenerative disease, characterized by an early loss of memory as well as impairment of other intellectual functions, eventually resulting in the onset of dementia. The LamR may play a role in the progression of AD. Accordingly, study of the LamR crystal may play a role in treating and preventing AD.

The brains of humans afflicted with AD experience extensive neuronal loss in the hipocampus, neocortex, and other areas of the brain. Such brains have been found to be histopathologically characterized by numerous extracellular deposits, or lesions, comprising senile plaques and neurofibrillary tangles.

The interaction between laminin and the amyloid precursor protein (hereinafter "APP")—which yields Aβ as a proteolytic fragment of APP—is, generally linked to the progressive development of the senile plaques (also known as amyloid plaques) which appear to disrupt the extracellular matrix when APP is overproduced. Aβ polymerizes into amyloid fibrils and is the major component of the plaques. These lesions have neurotoxic effects and are one of the causes, if not the primary cause, of neurodegeneration. AD brain tissue also has elevated expression of laminin compared to normal brain tissue.

Nonetheless, laminin has been found to be a potent inhibitor of the Aβ fibril formation responsible for the development of the plaques, as laminin has been shown to attenuate the neurotoxicity of amyloid. A chain containing the sequence IKVAV (a laminin-derived peptide), for example, has been found to inhibit amyloidogenesis by depolymerizing Aβ. This inhibition appears to be due to laminin's particular interaction with Aβ which results in the inducement of depolymerization of Aβ fibrils that are so instrumental in the onset and generation of AD and that are present in its telltale lesions. Laminin has also been shown to modulate the biogenesis of APP. Such interactions have also inhibited the toxic effects on rat primary hippocampal neurons.

Screening mechanisms as disclosed herein may also be used for the discovery and design of specific therapeutic drugs which treat various disease states by targeting the LamR. Once a drug is selected, the drug may then be produced through ordinary chemical synthesis. In addition, a pharmaceutically acceptable carrier may then be added thereto.

Accordingly, a method for producing a pharmaceutical composition which comprises a step of producing the drug obtainable by the above mentioned screening methods is within the scope of the presently disclosed embodiments.

As further disclosure of the presently disclosed embodiments, the, following Preparations and Examples are provided to illustrate specific embodiments and aspects of the presently disclosed embodiments. The illustration of specific embodiments and aspects, however, is not intended to limit the scope of this disclosure.

Materials And Methods (i) Recombinant LamR Expression and Purification

Full-length human laminin receptor having residues 1-295 (LamR-295) was cloned into an *E. coli* expression vector that includes a TEV-cleavable, N-terminal 6×His-tag. The vector encoding LamR-295 was transformed into *E. coli* strain BL21 (DE3*) and cultures were grown in Luria broth media at 37° C. to an $OD_{600}$ of 0.6. Protein expression was induced by the addition of isopropyl-thiogalactopyranoside (IPTG, 0.1 mM) for 12 hours at 20° C. Cells were harvested, resuspended in lysis buffer (50 mM Tris (pH 8.0), 300 mM NaCl, 0.1% Triton X-100, 10% glycerol, EDTA-free protease inhibitor tablet (Roche)) and lysed by French press. The lysate was centrifuged at 16,000 RPM for 30 minutes and the supernatant was collected. The soluble fraction was purified by Ni-NTA chromatography (Qiagen), followed by gel filtration chromatography (Superdex 75, Amersham). Protein was concentrated in spin concentrators (Amicon, Millipore).

Expression and purification of LamR-295 was verified by coomassie staining and Western blot using both anti-His and anti-LamR antibodies. Purification of LamR-295 resulted in an impure protein product which was evident by multiple bands in both the coomassie stain and Western blot. In order to crystallize a protein, an extremely high level of purity is necessary. Thus, various shorter-length LamRs were subcloned from the full-length human LamR-295 cDNA and expression and purification was tested.

Next, the following LamR constructs were tested for expression and purification for crystallography purposes: residues 1-198, 12-198, 1-220, 12-220, and 1-206. Constructs comprising residues 12-198 and 1-198 were tested due to a sequence alignment between T. thermophilus 40S ribosomal protein S0-A, which was solved by CryoEM structure. Residues 12-220 and 1-220 were tested because trypsin digestion of the full-length LamR construct corresponded to a stable protein of 25 kDa, which approximately corresponds to amino acids 1-220. In addition, N-terminal sequencing of LamR-295 confirmed that the full-length construct was not being degraded from the N-terminus.

Due to the highly pure protein product (>95%) obtained from the LamR-220 construct, to the LamR-220 construct was chosen for pursuing crystallization screenings Residues 1-220 of human 37 kDa LamR protein (LamR-220,) were subcloned from a full-length LamR cDNA into an E. coli expression vector that includes a TEV-cleavable, N-terminal 6×His-tag. The construct was verified by automated DNA sequencing. The vector encoding LamR-220 was transformed into E. coli strain BL21 (DE3*), and cultures were grown in Luria broth media at 37° C. to an $OD_{600}$ of 0.6. Protein expression was induced by the addition of isopropyl-thiogalactopyranoside (IPTG, 0.1 mM) for 12 hours at 20° C. Cells were harvested, resuspended in lysis buffer (50 mM Tris (pH 8.0), 300 mM NaCl, 0.1% Triton X-100, 10% glycerol, EDTA-free protease inhibitor tablet (Roche)) and lysed by French press. The lysate was centrifuged at 16,000 RPM for 30 minutes and the supernatant was collected. The soluble fraction was purified by Ni-NTA chromatography (Qiagen), followed by gel filtration chromatography (Superdex 75, Amersham). Protein was concentrated in spin concentrators (Amicon, Millipore).

(ii) Crystallization and Data Collection

The most frequently used crystallization method is a vapor diffusion technique in which a 1 µl droplet of recombinant purified protein is mixed with an equal volume of the crystallizing solution that contains buffer, salt and precipitant. This droplet is placed on a siliconized glass cover slip which is inverted and sealed into place over a reservoir of 500 µl of the crystallization solution. The concentration difference between the drop and the reservoir drives the system to equilibrium by diffusion through the vapor phase.

Crystals of LamR-220 were grown at 17° C. by the hanging-drop vapor diffusion method in drops containing a 1:1 (v/v) ratio of protein solution at 10 mg/ml and reservoir solution containing 17% (w/v) PEG, 10 K, 120 mM sodium citrate, 100 mM MES [pH 6.0], and 5% (w/v) PEG 1.5 K. Crystals belong to the tetragonal space group $P4_32_12$ with unit cell dimensions of a=75.666 Å, b=75.666 Å, and c=98.965 Å. Crystals were soaked briefly in crystallization buffer with 20% glycerol (v/v) and then flash frozen in liquid nitrogen. There is one LamR-220 molecule in the asymmetric unit with a solvent content of 56%. Diffraction data were collected to a resolution of 2.15 Å at X29 at the National Synchrotron Light Source at Brookhaven National Laboratory. Data were processed with the HKL2000 (Otwinowski 1997). A molecular replacement solution was found with AMoRE (Navaza 1994) using as a search model the structure of the A. fulgidus 30s ribosomal protein S2p [PDB code 1VI6, chain A] (Badger 2005). Rigid-body refinement, simulated annealing and positional and B-factor refinement were performed with CNS (Brunger 1998) and Refmac (Mushudov 1997). Coot was used for model building (Emsley 2004). According to PROCHECK (Laskowski 1993), 94.8% of the residues have backbone torsion angles in most favored regions and 5.2% in additional allowed regions.

(iii) In vitro Binding Affinity for Laminin-1

LamR-220 and LamR-295 were tested in vitro for their ability to bind with laminin-1. White polystyrene ELISA 96-well microplates, precoated with murine laminin-1 (NEBiolabs), were blocked O/N at 4° C. with blocking buffer (3.0% BSA, 0.1% sodium azide in PBS). Wells were incubated with increasing concentrations of LamR-220 or LamR-295, which was Ni-affinity purified as described, above for 1 hour at 37° C. Each well was washed three times with blocking buffer. Penta-His HRP conjugate (1:500) (Qiagen) was incubated for 2 hours at RT and wells were washed three times with blocking buffer. Substrate solution was added and incubated for approximately 15 minutes before reading fluorescent absorbance was detected at 490 nm on an ELISA plate reader ($EL_x800$, Biotek Instruments, Inc.). Controls for buffer alone and nonspecific protein, BSA (NEBiolabs), were also tested. Experiments were performed in triplicate. A binding curve and $K_d$ was generated for LamR-220 and LamR-295. The $K_d$ was calculated using a one-site binding hyperbola and the equation $Y=B_{max} \times X/(k_d+X)$. Each group was tested in triplicate and binding affinity was determined by normalizing to background fluorescence. Results are shown in FIG. 2A.

(iv) Protocol for Protein Purification

A protocol for protein purification includes, but is not limited to, the following:

Expression:
1. inoculate 100 ml LB+30 µg/ml Kanymycin O/N at 37° C.
2. increase volume to 800-1000 mL LB+Kan in 2 L flask
3. grow at 37° C. until $OD_{600}$=0.4 to 0.6
4. induce with 1 mM IPTG O/N at 20° C.
5. spin down at 10,000 rpm for about 30 minutes and store pellets at −80° C. or Ni-purify Nickel-Affinity Purification:
1. resuspend 1 L pellet in 30 mL of lysis buffer with 1 tablet EDTA-free protease inhibitor (do this in ice bucket)
   a. dissolve protease tablet in lysis buffer before adding to protein pellet
2. sonicate for about 20 minutes (3 seconds on, 12 seconds off, at level 3)
   a. in ice bucket
   b. OR French press two times
3. spin down at 16,000 rpm for 30-45 minutes
4. filter supernatant in 0.45 µm Millipore 150 ml sterile filters
5. add 1 mL Ni-agarose beads/1 L original inoculation culture to large 20 mL disposable column
   a. add stop cock to control flow
6. add 10 mL lysis buffer over beads and let flow through to wash
7. add protein supernatant, collect flow through (FT)
   a. control flow so that it is fairly slow
8. add 20 mL wash buffer and collect (W1)
9. add another 20 mL wash buffer and collect (W2)
10. add 5 mL elution buffer and, collect five 1 mL fractions (E1-5)
11. run 10 µL of PC, FT, W1, W2, E1-5 in 15% SDS-PAGE
12. stain with 0.025% coomassie stain for 15-30 minutes, destain Size Exclusion Chromatography:
1. collect fractions with most protein and concentrate to 2 mL, filter
2. wash Superdex-75 column with S75 buffer
3. run protein on Superdex-75 column and collect fractions
4. run fractions in 15% SDS-PAGE
5. concentrate to desired concentration (v) In vitro Sindbis Virus Vector Inhibition Three million (3×10⁶) BHK-55 cells were plated in a 12-well plate for 24 hours in αMEM (Cellgro) supplemented with 10% FBS. Sindbis virus vector that expressed a luciferin reporter upon replication (multiplicity of infection (MOI)= 100) was incubated with control protein (BSA, NEBiolabs), LamR-220, or alone and rotated at room temperature for 1 hour. Cells were washed with Optimem (Gibco) and 300 μl of sample was added. Samples were incubated rotating gently for 1 hour at room temperature to allow Sindbis viral vector attachment. The supernatant was aspirated, cells were washed with PBS, and 1 ml of media was added. The cells were incubated O/N at 37° C. and media was aspirated the next day. 200 μl of unsupplemented media and 200 μl of luciferin substrate (SteadyGlo Luciferase Assay, Promega) was added. The cells were shaken vigorously for 15 minutes. The relative luciferase units (RLU), which correspond to infectivity of Sindbis virus vector, of each sample were read using a luminometer (Glomax 20/20, Promega). Experiments were performed in triplicate. A two-tailed student t-test was performed, (P<0.05) to determine statistical significance. Results are shown in FIG. 2B.

All patents, patent applications, and published references cited herein are hereby incorporated by reference in their, entirety. This disclosure presents illustrative embodiments by way of representation and not limitation. Numerous other modifications and embodiments may be devised by those skilled in the art which fall within the scope and spirit of the principles of the presently disclosed embodiments and the following claims.

REFERENCES CITED

1. Jackers, P., Minoletti, F., Belotti, D., Clausse, N., Sozzi, G., Sobel, M. E., and Castronovo, V. (1996) *Oncogene* 13(3), 495-503;
2. Ardini, E., Pesole, G., Tagliabue, E., Magnifico, A., Castronovo, V. Sobel, M. E., Colnaghi, M. I., and Menard, S. (1998) *Mol Biol Evol* 15 (8), 1017-1025;
3. Rao, N. C., Barsky, S. H., Terranova, V. P., and Liotta, L. A., (,1983) *Biochemical and biophysical research communications* 111(3), 804-808;
4. Gauczynski, S., Peyrin, J. M., Haik, S., Leucht, C., Hundt, C., Rieger, R., Krasemann, S., Deslys, J. P., Dormont, D., Lasmezas, C. I., and Weiss, S. (2001) *Embo J* 20(21), 5863-5875;
5. Wang, K. S., Kuhn, R. J., Strauss, E. G., Ou, S., and Strauss, J. H. (1992) *J Virol* 66(8), 4992-5001;
6. Ludwig, G. V., Kondig, J. P., and Smith, J. F. (1996) *J Virol* 70(8) 5592-5599;
7. McNichol, B. A., Rasmussen, S. B., Carvalho, H. M., Meysick, K. C., and O'Brien A, D. (2007) *Infect Immun;*
8. Akache, B., Grimm, D., Pandey, K., Yant., S. R., Xu, H., and Kay, M. A. (2006) *J Virol* 80(19), 9831-9836;
9. Landowski, T. H., Dratz, E. A., and Starkey, J. R. (1995) *Biochemistry* 34(35), 11276-11287;
10. Menard, S., Tagliabue, E., and Colnaghi, M. I. (1998) *Breast Cancer Res Treat* 52(1-3), 137-145;
11. Auth, D., and Brawerman, G. (1992) *Proceedings of the National Academy of Sciences of the United States of America* 89(10), 4368-4372;
12. Sato, M., Kinoshita, K., Kaneda, U., Saeki, Y., Iwamatsu, A., and Tanaka, K. (1996) *Biochemical and biophysical research communications* 229(3), 896-901;
13. Ford, C. L., Randal-Whitis, L., and Ellis, S. R. (1999) *Cancer research* 59(3), 704-710;
14. Otwinowski, Z., and Minor, W. (19.97) *Methods Enzymol.* 276, 307-326;
15. Navaza, J. (1994) *Acta Crystallogr.* A 50, 157-163;
16. Badger, J., Sauder, J. M., Adams, J. M., Antonysamy, S., Bain, K., Bergseid, M. G., Buchanan, S. G., Buchanan, M. D., Batiyenko, Y., Christopher, J. A., Emtage, S., Eroshkina, A., Feil, I., Furlong, E. B., Gajiwala, K. S., Gao, X., He, D., Hendle, J., Huber, A., Hoda, K., Kearins, P., Kissinger, C., Laubert, B., Lewis, H. A., Lin, J., Loomis, K., Lorimer, D., Louie, G., Maletic, M., Marsh, C. D., Miller, I., Molinari, J., Muller-Dieckmann, H. J., Newman, J. M., Noland, B. W., Pagarigan, B., Park, F., Peat, T. S., Post, K. W., Radojicic, S., Ramos, A., Romero, R., Rutter, M. E., Sanderson, W. E., Schwinn, K. D., Tresser, J., Winhoven, J., Wright, T. A., Wu, L., Xu, J., and Harris, T. J. (,2005) *Proteins* 60(4), 787-796;
17. Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson T., and Warren, G. L. (1998) *Acta crystallographica* 54(Pt 5), 905-921;
18. Murshudov, G. N., Vagin, A. A., and Dodson, E. J. (1997) *Acta crystallographica* 53(Pt 3), 240-255;
19. Emsley, P., and Cowtan, K. (2004) *Acta crystallographica* 60(Pt 12 Pt 1), 2126-2132;
20. Laskowski, R., MacArthur, M. W., Moss, D. S., and Thornton, J. M. (1993) PROCHECK: a program to check the stereochemical quality of protein structures. *J. Appl. Cryst.,* 26, 283-291;
21. Wimberly, B. T., Brodersen, D. E., Clemons, W. M., Jr., Morgan-Warren, R. J., Carter, A. P., Vonrhein, C., Hartsch, T., and Ramakrishnan, V. (2000) *Nature* 407(6802), 327-339;
22. Castronovo, V., Taraboletti, G., and Sobel, M. E. (1991) *J Biol Chem* 266 (30), 20440-20446;
23. Tanaka, M., Narumi, K., Isemura, M., Abe, M., Sato, Y., Abe, T., Saijo, Y., Nukiwa, T., and Satoh, K. (2000) *Cancer Lett* 153 (1-2), 161-168;
24. Tachibana, H., Koga, K., Fujimura, Y., and Yamada, K. (2004) *Nat Struct Mol Biol* 11(4), 380-381;
25. Tseng, J C., Levin, B., Hurtado, A., Yee, H., Perez de Castro, I., Jimenez, M., Shamamian, P., Jin R., Novick, R. P., Pellicer, A., and Meruelo, D. (2004) *Nat Biotechnol* 22(1), 70-77; and
26. Cao, Y., and Cao, R. (1999) *Nature* 398(6726), 381.

APPENDIX 1

X-RAY DATA COORDINATES FOR LRP-220 (SEQ ID NO: 5)

| Unit cell: | | 75.666 | | 75.666 | | 98.965 | 90.00 | 90.00 | 90.00 | | |
|---|---|---|---|---|---|---|---|---|---|---|---|
| Space Group: | | P4₃2₁2 | | | | | | | | | |
| ATOM | 1 | N | GLN | X | 9 | 32.089 | 42.564 | 44.187 | 1.00 | 39.73 | N |
| ATOM | 2 | CA | GLN | X | 9 | 32.301 | 44.031 | 44.338 | 1.00 | 39.55 | C |
| ATOM | 3 | CB | GLN | X | 9 | 32.131 | 44.729 | 42.990 | 1.00 | 39.97 | C |
| ATOM | 4 | CG | GLN | X | 9 | 32.703 | 46.131 | 42.948 | 1.00 | 41.74 | C |
| ATOM | 5 | CD | GLN | X | 9 | 31.798 | 47.087 | 42.215 | 1.00 | 43.97 | C |

APPENDIX 1-continued

X-RAY DATA COORDINATES FOR LRP-220 (SEQ ID NO: 5)

| ATOM | 6 | OE1 | GLN | X | 9 | 30.698 | 46.713 | 41.797 | 1.00 | 45.56 | O |
|---|---|---|---|---|---|---|---|---|---|---|---|
| ATOM | 7 | NE2 | GLN | X | 9 | 32.244 | 48.335 | 42.062 | 1.00 | 44.38 | N |
| ATOM | 8 | C | GLN | X | 9 | 31.341 | 44.621 | 45.376 | 1.00 | 38.74 | C |
| ATOM | 9 | O | GLN | X | 9 | 31.550 | 45.728 | 45.883 | 1.00 | 38.77 | O |
| ATOM | 10 | N | MET | X | 10 | 30.285 | 43.872 | 45.679 | 1.00 | 37.79 | N |
| ATOM | 11 | CA | MET | X | 10 | 29.419 | 44.176 | 46.807 | 1.00 | 36.89 | C |
| ATOM | 12 | CB | MET | X | 10 | 28.177 | 43.277 | 46.769 | 1.00 | 37.05 | C |
| ATOM | 13 | CG | MET | X | 10 | 27.190 | 43.495 | 47.905 | 1.00 | 36.49 | C |
| ATOM | 14 | SD | MET | X | 10 | 25.593 | 42.715 | 47.601 | 1.00 | 37.00 | S |
| ATOM | 15 | CE | MET | X | 10 | 26.002 | 40.969 | 47.535 | 1.00 | 36.22 | C |
| ATOM | 16 | C | MET | X | 10 | 30.222 | 43.953 | 48.090 | 1.00 | 36.08 | C |
| ATOM | 17 | O | MET | X | 10 | 30.799 | 42.881 | 48.285 | 1.00 | 35.72 | O |
| ATOM | 18 | N | LYS | X | 11 | 30.270 | 44.968 | 48.947 | 1.00 | 35.03 | N |
| ATOM | 19 | CA | LYS | X | 11 | 31.070 | 44.896 | 50.163 | 1.00 | 34.37 | C |
| ATOM | 20 | CB | LYS | X | 11 | 31.573 | 46.284 | 50.571 | 1.00 | 34.63 | C |
| ATOM | 21 | CG | LYS | X | 11 | 32.737 | 46.797 | 49.708 | 1.00 | 34.83 | C |
| ATOM | 22 | CD | LYS | X | 11 | 33.164 | 48.201 | 50.118 | 1.00 | 35.43 | C |
| ATOM | 23 | CE | LYS | X | 11 | 34.298 | 48.740 | 49.230 | 1.00 | 37.13 | C |
| ATOM | 24 | NZ | LYS | X | 11 | 34.377 | 50.245 | 49.264 | 1.00 | 38.00 | N |
| ATOM | 25 | C | LYS | X | 11 | 30.334 | 44.201 | 51.310 | 1.00 | 33.41 | C |
| ATOM | 26 | O | LYS | X | 11 | 29.103 | 44.242 | 51.386 | 1.00 | 33.19 | O |
| ATOM | 27 | N | GLU | X | 12 | 31.112 | 43.560 | 52.185 | 1.00 | 32.40 | N |
| ATOM | 28 | CA | GLU | X | 12 | 30.603 | 42.748 | 53.296 | 1.00 | 31.60 | C |
| ATOM | 29 | CB | GLU | X | 12 | 31.765 | 42.159 | 54.113 | 1.00 | 31.72 | C |
| ATOM | 30 | CG | GLU | X | 12 | 32.593 | 41.085 | 53.398 | 1.00 | 32.86 | C |
| ATOM | 31 | CD | GLU | X | 12 | 33.959 | 40.834 | 54.062 | 1.00 | 33.84 | C |
| ATOM | 32 | OE1 | GLU | X | 12 | 34.513 | 41.763 | 54.708 | 1.00 | 35.58 | O |
| ATOM | 33 | OE2 | GLU | X | 12 | 34.482 | 39.698 | 53.936 | 1.00 | 36.48 | O |
| ATOM | 34 | C | GLU | X | 12 | 29.695 | 43.552 | 54.215 | 1.00 | 30.09 | C |
| ATOM | 35 | O | GLU | X | 12 | 28.652 | 43.063 | 54.652 | 1.00 | 29.50 | O |
| ATOM | 36 | N | GLU | X | 13 | 30.110 | 44.786 | 54.497 | 1.00 | 28.75 | N |
| ATOM | 37 | CA | GLU | X | 13 | 29.368 | 45.693 | 55.363 | 1.00 | 27.76 | C |
| ATOM | 38 | CB | GLU | X | 13 | 30.201 | 46.943 | 55.688 | 1.00 | 28.33 | C |
| ATOM | 39 | CG | GLU | X | 13 | 31.614 | 46.666 | 56.196 | 1.00 | 31.49 | C |
| ATOM | 40 | CD | GLU | X | 13 | 32.670 | 46.790 | 55.104 | 1.00 | 34.76 | C |
| ATOM | 41 | OE1 | GLU | X | 13 | 32.827 | 45.844 | 54.295 | 1.00 | 35.71 | O |
| ATOM | 42 | OE2 | GLU | X | 13 | 33.353 | 47.840 | 55.066 | 1.00 | 36.51 | O |
| ATOM | 43 | C | GLU | X | 13 | 28.034 | 46.111 | 54.742 | 1.00 | 25.85 | C |
| ATOM | 44 | O | GLU | X | 13 | 27.083 | 46.394 | 55.461 | 1.00 | 25.59 | O |
| ATOM | 45 | N | ASP | X | 14 | 27.976 | 46.155 | 53.411 | 1.00 | 24.16 | N |
| ATOM | 46 | CA | ASP | X | 14 | 26.740 | 46.506 | 52.703 | 1.00 | 22.20 | C |
| ATOM | 47 | CB | ASP | X | 14 | 27.023 | 46.949 | 51.268 | 1.00 | 22.02 | C |
| ATOM | 48 | CG | ASP | X | 14 | 27.631 | 48.353 | 51.193 | 1.00 | 21.77 | C |
| ATOM | 49 | OD1 | ASP | X | 14 | 27.367 | 49.190 | 52.084 | 1.00 | 21.02 | O |
| ATOM | 50 | OD2 | ASP | X | 14 | 28.369 | 48.623 | 50.230 | 1.00 | 20.85 | O |
| ATOM | 51 | C | ASP | X | 14 | 25.770 | 45.334 | 52.733 | 1.00 | 21.02 | C |
| ATOM | 52 | O | ASP | X | 14 | 24.564 | 45.525 | 52.896 | 1.00 | 20.55 | O |
| ATOM | 53 | N | VAL | X | 15 | 26.308 | 44.125 | 52.600 | 1.00 | 19.77 | N |
| ATOM | 54 | CA | VAL | X | 15 | 25.510 | 42.910 | 52.751 | 1.00 | 19.38 | C |
| ATOM | 55 | CB | VAL | X | 15 | 26.347 | 41.624 | 52.543 | 1.00 | 19.36 | C |
| ATOM | 56 | CG1 | VAL | X | 15 | 25.496 | 40.377 | 52.830 | 1.00 | 19.68 | C |
| ATOM | 57 | CG2 | VAL | X | 15 | 26.907 | 41.570 | 51.119 | 1.00 | 19.73 | C |
| ATOM | 58 | C | VAL | X | 15 | 24.831 | 42.888 | 54.124 | 1.00 | 18.45 | C |
| ATOM | 59 | O | VAL | X | 15 | 23.650 | 42.595 | 54.224 | 1.00 | 18.63 | O |
| ATOM | 60 | N | LEU | X | 16 | 25.577 | 43.230 | 55.172 | 1.00 | 17.93 | N |
| ATOM | 61 | CA | LEU | X | 16 | 25.030 | 43.237 | 56.534 | 1.00 | 17.17 | C |
| ATOM | 62 | CB | LEU | X | 16 | 26.152 | 43.372 | 57.569 | 1.00 | 17.29 | C |
| ATOM | 63 | CG | LEU | X | 16 | 27.107 | 42.181 | 57.710 | 1.00 | 17.24 | C |
| ATOM | 64 | CD1 | LEU | X | 16 | 28.212 | 42.527 | 58.702 | 1.00 | 18.83 | C |
| ATOM | 65 | CD2 | LEU | X | 16 | 26.363 | 40.935 | 58.147 | 1.00 | 17.49 | C |
| ATOM | 66 | C | LEU | X | 16 | 23.966 | 44.311 | 56.746 | 1.00 | 16.62 | C |
| ATOM | 67 | O | LEU | X | 16 | 23.010 | 44.097 | 57.488 | 1.00 | 16.22 | O |
| ATOM | 68 | N | LYS | X | 17 | 24.148 | 45.465 | 56.102 | 1.00 | 16.26 | N |
| ATOM | 69 | CA | LYS | X | 17 | 23.145 | 46.536 | 56.085 | 1.00 | 15.87 | C |
| ATOM | 70 | CB | LYS | X | 17 | 23.700 | 47.779 | 55.381 | 1.00 | 15.92 | C |
| ATOM | 71 | CG | LYS | X | 17 | 24.573 | 48.661 | 56.265 | 1.00 | 16.73 | C |
| ATOM | 72 | CD | LYS | X | 17 | 24.935 | 49.962 | 55.557 | 1.00 | 16.22 | C |
| ATOM | 73 | CE | LYS | X | 17 | 25.643 | 50.911 | 56.513 | 1.00 | 19.22 | C |
| ATOM | 74 | NZ | LYS | X | 17 | 26.950 | 50.349 | 56.984 | 1.00 | 19.58 | N |
| ATOM | 75 | C | LYS | X | 17 | 21.862 | 46.086 | 55.390 | 1.00 | 15.47 | C |
| ATOM | 76 | O | LYS | X | 17 | 20.762 | 46.266 | 55.921 | 1.00 | 15.51 | O |
| ATOM | 77 | N | PHE | X | 18 | 22.016 | 45.508 | 54.199 | 1.00 | 15.19 | N |
| ATOM | 78 | CA | PHE | X | 18 | 20.905 | 44.929 | 53.450 | 1.00 | 15.34 | C |
| ATOM | 79 | CB | PHE | X | 18 | 21.428 | 44.207 | 52.203 | 1.00 | 15.08 | C |
| ATOM | 80 | CG | PHE | X | 18 | 21.768 | 45.112 | 51.036 | 1.00 | 15.12 | C |
| ATOM | 81 | CD1 | PHE | X | 18 | 20.991 | 46.227 | 50.727 | 1.00 | 14.63 | C |
| ATOM | 82 | CE1 | PHE | X | 18 | 21.296 | 47.039 | 49.623 | 1.00 | 14.97 | C |
| ATOM | 83 | CZ | PHE | X | 18 | 22.386 | 46.729 | 48.817 | 1.00 | 15.27 | C |

APPENDIX 1-continued

X-RAY DATA COORDINATES FOR LRP-220 (SEQ ID NO: 5)

| ATOM | 84  | CE2 | PHE | X | 18 | 23.165 | 45.610 | 49.108 | 1.00 | 16.09 | C |
|------|-----|-----|-----|---|----|--------|--------|--------|------|-------|---|
| ATOM | 85  | CD2 | PHE | X | 18 | 22.847 | 44.805 | 50.214 | 1.00 | 15.18 | C |
| ATOM | 86  | C   | PHE | X | 18 | 20.130 | 43.926 | 54.316 | 1.00 | 15.81 | C |
| ATOM | 87  | O   | PHE | X | 18 | 18.894 | 43.961 | 54.385 | 1.00 | 15.46 | O |
| ATOM | 88  | N   | LEU | X | 19 | 20.868 | 43.027 | 54.965 | 1.00 | 16.26 | N |
| ATOM | 89  | CA  | LEU | X | 19 | 20.259 | 42.005 | 55.827 | 1.00 | 16.69 | C |
| ATOM | 90  | CB  | LEU | X | 19 | 21.319 | 40.977 | 56.266 | 1.00 | 16.82 | C |
| ATOM | 91  | CG  | LEU | X | 19 | 21.353 | 40.022 | 57.478 | 1.00 | 17.48 | C |
| ATOM | 92  | CD1 | LEU | X | 19 | 20.113 | 39.951 | 58.393 | 1.00 | 17.46 | C |
| ATOM | 93  | CD2 | LEU | X | 19 | 21.775 | 38.645 | 56.993 | 1.00 | 16.57 | C |
| ATOM | 94  | C   | LEU | X | 19 | 19.468 | 42.588 | 56.994 | 1.00 | 16.54 | C |
| ATOM | 95  | O   | LEU | X | 19 | 18.319 | 42.200 | 57.209 | 1.00 | 16.87 | O |
| ATOM | 96  | N   | ALA | X | 20 | 20.068 | 43.533 | 57.717 | 1.00 | 16.46 | N |
| ATOM | 97  | CA  | ALA | X | 20 | 19.408 | 44.199 | 58.849 | 1.00 | 16.22 | C |
| ATOM | 98  | CB  | ALA | X | 20 | 20.374 | 45.177 | 59.541 | 1.00 | 16.21 | C |
| ATOM | 99  | C   | ALA | X | 20 | 18.118 | 44.914 | 58.440 | 1.00 | 16.31 | C |
| ATOM | 100 | O   | ALA | X | 20 | 17.133 | 44.907 | 59.191 | 1.00 | 16.26 | O |
| ATOM | 101 | N   | ALA | X | 21 | 18.125 | 45.513 | 57.246 | 1.00 | 15.98 | N |
| ATOM | 102 | CA  | ALA | X | 21 | 16.961 | 46.240 | 56.726 | 1.00 | 15.51 | C |
| ATOM | 103 | CB  | ALA | X | 21 | 17.404 | 47.320 | 55.750 | 1.00 | 15.57 | C |
| ATOM | 104 | C   | ALA | X | 21 | 15.923 | 45.336 | 56.070 | 1.00 | 15.27 | C |
| ATOM | 105 | O   | ALA | X | 21 | 14.822 | 45.787 | 55.762 | 1.00 | 15.73 | O |
| ATOM | 106 | N   | GLY | X | 22 | 16.273 | 44.068 | 55.855 | 1.00 | 14.77 | N |
| ATOM | 107 | CA  | GLY | X | 22 | 15.408 | 43.130 | 55.144 | 1.00 | 14.09 | C |
| ATOM | 108 | C   | GLY | X | 22 | 15.254 | 43.441 | 53.662 | 1.00 | 13.92 | C |
| ATOM | 109 | O   | GLY | X | 22 | 14.189 | 43.241 | 53.093 | 1.00 | 13.77 | O |
| ATOM | 110 | N   | THR | X | 23 | 16.323 | 43.915 | 53.029 | 1.00 | 13.85 | N |
| ATOM | 111 | CA  | THR | X | 23 | 16.268 | 44.338 | 51.618 | 1.00 | 13.68 | C |
| ATOM | 112 | CB  | THR | X | 23 | 17.522 | 45.161 | 51.240 | 1.00 | 13.54 | C |
| ATOM | 113 | OG1 | THR | X | 23 | 17.609 | 46.295 | 52.118 | 1.00 | 12.71 | O |
| ATOM | 114 | CG2 | THR | X | 23 | 17.464 | 45.654 | 49.782 | 1.00 | 13.41 | C |
| ATOM | 115 | C   | THR | X | 23 | 15.994 | 43.164 | 50.649 | 1.00 | 13.97 | C |
| ATOM | 116 | O   | THR | X | 23 | 15.357 | 43.337 | 49.593 | 1.00 | 13.34 | O |
| ATOM | 117 | N   | HIS | X | 24 | 16.425 | 41.971 | 51.058 | 1.00 | 13.71 | N |
| ATOM | 118 | CA  | HIS | X | 24 | 16.247 | 40.734 | 50.289 | 1.00 | 14.30 | C |
| ATOM | 119 | CB  | HIS | X | 24 | 17.132 | 39.631 | 50.892 | 1.00 | 14.16 | C |
| ATOM | 120 | CG  | HIS | X | 24 | 16.844 | 39.364 | 52.335 | 1.00 | 14.97 | C |
| ATOM | 121 | ND1 | HIS | X | 24 | 16.114 | 38.273 | 52.761 | 1.00 | 16.93 | N |
| ATOM | 122 | CE1 | HIS | X | 24 | 16.007 | 38.304 | 54.077 | 1.00 | 15.26 | C |
| ATOM | 123 | NE2 | HIS | X | 24 | 16.627 | 39.382 | 54.520 | 1.00 | 15.35 | N |
| ATOM | 124 | CD2 | HIS | X | 24 | 17.157 | 40.064 | 53.451 | 1.00 | 14.02 | C |
| ATOM | 125 | C   | HIS | X | 24 | 14.806 | 40.226 | 50.268 | 1.00 | 14.30 | C |
| ATOM | 126 | O   | HIS | X | 24 | 14.491 | 39.283 | 49.543 | 1.00 | 13.87 | O |
| ATOM | 127 | N   | LEU | X | 25 | 13.943 | 40.834 | 51.078 | 1.00 | 14.73 | N |
| ATOM | 128 | CA  | LEU | X | 25 | 12.592 | 40.330 | 51.264 | 1.00 | 15.36 | C |
| ATOM | 129 | CB  | LEU | X | 25 | 12.061 | 40.685 | 52.661 | 1.00 | 15.55 | C |
| ATOM | 130 | CG  | LEU | X | 25 | 12.652 | 39.923 | 53.848 | 1.00 | 16.91 | C |
| ATOM | 131 | CD1 | LEU | X | 25 | 12.091 | 40.470 | 55.160 | 1.00 | 19.07 | C |
| ATOM | 132 | CD2 | LEU | X | 25 | 12.398 | 38.410 | 53.737 | 1.00 | 18.51 | C |
| ATOM | 133 | C   | LEU | X | 25 | 11.638 | 40.823 | 50.185 | 1.00 | 15.63 | C |
| ATOM | 134 | O   | LEU | X | 25 | 11.312 | 42.004 | 50.121 | 1.00 | 15.72 | O |
| ATOM | 135 | N   | GLY | X | 26 | 11.209 | 39.907 | 49.326 | 1.00 | 16.10 | N |
| ATOM | 136 | CA  | GLY | X | 26 | 10.210 | 40.217 | 48.319 | 1.00 | 16.93 | C |
| ATOM | 137 | C   | GLY | X | 26 | 8.854  | 39.855 | 48.874 | 1.00 | 17.73 | C |
| ATOM | 138 | O   | GLY | X | 26 | 8.695  | 39.668 | 50.093 | 1.00 | 17.81 | O |
| ATOM | 139 | N   | GLY | X | 27 | 7.877  | 39.722 | 47.983 | 1.00 | 18.17 | N |
| ATOM | 140 | CA  | GLY | X | 27 | 6.539  | 39.289 | 48.374 | 1.00 | 18.99 | C |
| ATOM | 141 | C   | GLY | X | 27 | 6.245  | 37.900 | 47.842 | 1.00 | 19.48 | C |
| ATOM | 142 | O   | GLY | X | 27 | 7.140  | 37.213 | 47.359 | 1.00 | 19.37 | O |
| ATOM | 143 | N   | THR | X | 28 | 4.987  | 37.489 | 47.933 | 1.00 | 19.94 | N |
| ATOM | 144 | CA  | THR | X | 28 | 4.594  | 36.158 | 47.481 | 1.00 | 20.79 | C |
| ATOM | 145 | CB  | THR | X | 28 | 3.406  | 35.610 | 48.309 | 1.00 | 20.95 | C |
| ATOM | 146 | OG1 | THR | X | 28 | 2.292  | 36.498 | 48.182 | 1.00 | 21.19 | O |
| ATOM | 147 | CG2 | THR | X | 28 | 3.791  | 35.506 | 49.778 | 1.00 | 21.28 | C |
| ATOM | 148 | C   | THR | X | 28 | 4.278  | 36.106 | 45.983 | 1.00 | 20.78 | C |
| ATOM | 149 | O   | THR | X | 28 | 4.208  | 35.024 | 45.400 | 1.00 | 21.53 | O |
| ATOM | 150 | N   | ASN | X | 29 | 4.096  | 37.268 | 45.360 | 1.00 | 20.74 | N |
| ATOM | 151 | CA  | ASN | X | 29 | 3.851  | 37.336 | 43.915 | 1.00 | 20.58 | C |
| ATOM | 152 | CB  | ASN | X | 29 | 2.637  | 38.220 | 43.600 | 1.00 | 20.72 | C |
| ATOM | 153 | CG  | ASN | X | 29 | 1.342  | 37.667 | 44.182 | 1.00 | 21.81 | C |
| ATOM | 154 | OD1 | ASN | X | 29 | 0.556  | 38.399 | 44.769 | 1.00 | 23.20 | O |
| ATOM | 155 | ND2 | ASN | X | 29 | 1.129  | 36.368 | 44.035 | 1.00 | 22.09 | N |
| ATOM | 156 | C   | ASN | X | 29 | 5.067  | 37.807 | 43.123 | 1.00 | 20.50 | C |
| ATOM | 157 | O   | ASN | X | 29 | 5.863  | 38.625 | 43.605 | 1.00 | 20.32 | O |
| ATOM | 158 | N   | LEU | X | 30 | 5.195  | 37.287 | 41.904 | 1.00 | 20.02 | N |
| ATOM | 159 | CA  | LEU | X | 30 | 6.341  | 37.562 | 41.064 | 1.00 | 20.09 | C |
| ATOM | 160 | CB  | LEU | X | 30 | 7.237  | 36.322 | 40.962 | 1.00 | 19.88 | C |
| ATOM | 161 | CG  | LEU | X | 30 | 8.521  | 36.381 | 40.122 | 1.00 | 19.08 | C |

APPENDIX 1-continued

X-RAY DATA COORDINATES FOR LRP-220 (SEQ ID NO: 5)

| ATOM | 162 | CD1 | LEU | X | 30 | 9.545 | 37.339 | 40.725 | 1.00 | 16.09 | C |
|---|---|---|---|---|---|---|---|---|---|---|---|
| ATOM | 163 | CD2 | LEU | X | 30 | 9.115 | 34.973 | 39.968 | 1.00 | 19.47 | C |
| ATOM | 164 | C | LEU | X | 30 | 5.923 | 38.034 | 39.674 | 1.00 | 20.50 | C |
| ATOM | 165 | O | LEU | X | 30 | 5.246 | 37.310 | 38.932 | 1.00 | 20.79 | O |
| ATOM | 166 | N | ASP | X | 31 | 6.324 | 39.256 | 39.341 | 1.00 | 20.38 | N |
| ATOM | 167 | CA | ASP | X | 31 | 6.194 | 39.779 | 37.991 | 1.00 | 20.64 | C |
| ATOM | 168 | CB | ASP | X | 31 | 6.471 | 41.285 | 37.985 | 1.00 | 20.84 | C |
| ATOM | 169 | CG | ASP | X | 31 | 6.192 | 41.916 | 36.639 | 1.00 | 21.00 | C |
| ATOM | 170 | OD1 | ASP | X | 31 | 7.080 | 41.876 | 35.763 | 1.00 | 20.07 | O |
| ATOM | 171 | OD2 | ASP | X | 31 | 5.070 | 42.435 | 36.463 | 1.00 | 22.23 | O |
| ATOM | 172 | C | ASP | X | 31 | 7.195 | 39.056 | 37.096 | 1.00 | 20.79 | C |
| ATOM | 173 | O | ASP | X | 31 | 8.330 | 38.805 | 37.511 | 1.00 | 20.52 | O |
| ATOM | 174 | N | PHE | X | 32 | 6.785 | 38.717 | 35.874 | 1.00 | 21.02 | N |
| ATOM | 175 | CA | PHE | X | 32 | 7.645 | 37.926 | 34.984 | 1.00 | 21.44 | C |
| ATOM | 176 | CB | PHE | X | 32 | 6.906 | 37.497 | 33.695 | 1.00 | 22.33 | C |
| ATOM | 177 | CG | PHE | X | 32 | 6.743 | 38.594 | 32.666 | 1.00 | 24.17 | C |
| ATOM | 178 | CD1 | PHE | X | 32 | 7.513 | 38.594 | 31.506 | 1.00 | 25.79 | C |
| ATOM | 179 | CE1 | PHE | X | 32 | 7.358 | 39.601 | 30.538 | 1.00 | 25.74 | C |
| ATOM | 180 | CZ | PHE | X | 32 | 6.424 | 40.610 | 30.729 | 1.00 | 24.87 | C |
| ATOM | 181 | CE2 | PHE | X | 32 | 5.637 | 40.619 | 31.880 | 1.00 | 25.78 | C |
| ATOM | 182 | CD2 | PHE | X | 32 | 5.796 | 39.610 | 32.838 | 1.00 | 26.21 | C |
| ATOM | 183 | C | PHE | X | 32 | 8.992 | 38.603 | 34.693 | 1.00 | 20.92 | C |
| ATOM | 184 | O | PHE | X | 32 | 10.004 | 37.932 | 34.499 | 1.00 | 20.47 | O |
| ATOM | 185 | N | GLN | X | 33 | 9.003 | 39.933 | 34.695 | 1.00 | 20.63 | N |
| ATOM | 186 | CA | GLN | X | 33 | 10.237 | 40.676 | 34.471 | 1.00 | 20.36 | C |
| ATOM | 187 | CB | GLN | X | 33 | 9.944 | 42.054 | 33.877 | 1.00 | 20.69 | C |
| ATOM | 188 | CG | GLN | X | 33 | 9.423 | 42.010 | 32.436 | 1.00 | 20.63 | C |
| ATOM | 189 | CD | GLN | X | 33 | 9.380 | 43.389 | 31.796 | 1.00 | 20.80 | C |
| ATOM | 190 | OE1 | GLN | X | 33 | 8.513 | 44.204 | 32.106 | 1.00 | 21.44 | O |
| ATOM | 191 | NE2 | GLN | X | 33 | 10.330 | 43.658 | 30.909 | 1.00 | 20.99 | N |
| ATOM | 192 | C | GLN | X | 33 | 11.117 | 40.781 | 35.723 | 1.00 | 19.86 | C |
| ATOM | 193 | O | GLN | X | 33 | 12.277 | 41.182 | 35.631 | 1.00 | 20.34 | O |
| ATOM | 194 | N | MET | X | 34 | 10.579 | 40.393 | 36.878 | 1.00 | 19.10 | N |
| ATOM | 195 | CA | MET | X | 34 | 11.354 | 40.381 | 38.127 | 1.00 | 18.63 | C |
| ATOM | 196 | CB | MET | X | 34 | 10.488 | 40.816 | 39.310 | 1.00 | 18.41 | C |
| ATOM | 197 | CG | MET | X | 34 | 10.126 | 42.316 | 39.316 | 1.00 | 19.19 | C |
| ATOM | 198 | SD | MET | X | 34 | 11.552 | 43.413 | 39.463 | 1.00 | 20.47 | S |
| ATOM | 199 | CE | MET | X | 34 | 12.166 | 42.944 | 41.084 | 1.00 | 17.02 | C |
| ATOM | 200 | C | MET | X | 34 | 12.022 | 39.030 | 38.421 | 1.00 | 18.36 | C |
| ATOM | 201 | O | MET | X | 34 | 12.887 | 38.937 | 39.298 | 1.00 | 18.26 | O |
| ATOM | 202 | N | GLU | X | 35 | 11.618 | 37.994 | 37.685 | 1.00 | 17.82 | N |
| ATOM | 203 | CA | GLU | X | 35 | 12.170 | 36.642 | 37.836 | 1.00 | 17.39 | C |
| ATOM | 204 | CB | GLU | X | 35 | 11.550 | 35.704 | 36.795 | 1.00 | 17.70 | C |
| ATOM | 205 | CG | GLU | X | 35 | 12.027 | 34.254 | 36.892 | 1.00 | 17.81 | C |
| ATOM | 206 | CD | GLU | X | 35 | 11.389 | 33.378 | 35.829 | 1.00 | 17.94 | C |
| ATOM | 207 | OE1 | GLU | X | 35 | 10.451 | 32.639 | 36.179 | 1.00 | 21.18 | O |
| ATOM | 208 | OE2 | GLU | X | 35 | 11.800 | 33.454 | 34.647 | 1.00 | 17.38 | O |
| ATOM | 209 | C | GLU | X | 35 | 13.696 | 36.618 | 37.723 | 1.00 | 16.83 | C |
| ATOM | 210 | O | GLU | X | 35 | 14.371 | 35.920 | 38.479 | 1.00 | 16.31 | O |
| ATOM | 211 | N | GLN | X | 36 | 14.236 | 37.409 | 36.796 | 1.00 | 16.08 | N |
| ATOM | 212 | CA | GLN | X | 36 | 15.683 | 37.514 | 36.610 | 1.00 | 15.59 | C |
| ATOM | 213 | CB | GLN | X | 36 | 15.991 | 38.389 | 35.391 | 1.00 | 16.04 | C |
| ATOM | 214 | CG | GLN | X | 36 | 15.618 | 39.873 | 35.563 | 1.00 | 15.36 | C |
| ATOM | 215 | CD | GLN | X | 36 | 15.634 | 40.641 | 34.251 | 1.00 | 16.46 | C |
| ATOM | 216 | OE1 | GLN | X | 36 | 14.598 | 41.159 | 33.810 | 1.00 | 19.47 | O |
| ATOM | 217 | NE2 | GLN | X | 36 | 16.796 | 40.710 | 33.618 | 1.00 | 14.17 | N |
| ATOM | 218 | C | GLN | X | 36 | 16.440 | 38.053 | 37.836 | 1.00 | 15.31 | C |
| ATOM | 219 | O | GLN | X | 36 | 17.664 | 37.941 | 37.897 | 1.00 | 15.21 | O |
| ATOM | 220 | N | TYR | X | 37 | 15.718 | 38.622 | 38.802 | 1.00 | 15.03 | N |
| ATOM | 221 | CA | TYR | X | 37 | 16.348 | 39.258 | 39.966 | 1.00 | 15.39 | C |
| ATOM | 222 | CB | TYR | X | 37 | 15.865 | 40.705 | 40.128 | 1.00 | 15.46 | C |
| ATOM | 223 | CG | TYR | X | 37 | 16.080 | 41.585 | 38.917 | 1.00 | 15.82 | C |
| ATOM | 224 | CD1 | TYR | X | 37 | 17.351 | 41.750 | 38.370 | 1.00 | 16.70 | C |
| ATOM | 225 | CE1 | TYR | X | 37 | 17.555 | 42.558 | 37.262 | 1.00 | 16.54 | C |
| ATOM | 226 | CZ | TYR | X | 37 | 16.485 | 43.223 | 36.694 | 1.00 | 16.10 | C |
| ATOM | 227 | OH | TYR | X | 37 | 16.707 | 44.023 | 35.596 | 1.00 | 17.59 | O |
| ATOM | 228 | CE2 | TYR | X | 37 | 15.213 | 43.085 | 37.213 | 1.00 | 15.68 | C |
| ATOM | 229 | CD2 | TYR | X | 37 | 15.017 | 42.265 | 38.328 | 1.00 | 15.46 | C |
| ATOM | 230 | C | TYR | X | 37 | 16.137 | 38.515 | 41.290 | 1.00 | 15.38 | C |
| ATOM | 231 | O | TYR | X | 37 | 16.695 | 38.904 | 42.309 | 1.00 | 15.60 | O |
| ATOM | 232 | N | ILE | X | 38 | 15.317 | 37.471 | 41.287 | 1.00 | 15.50 | N |
| ATOM | 233 | CA | ILE | X | 38 | 15.089 | 36.707 | 42.514 | 1.00 | 15.21 | C |
| ATOM | 234 | CB | ILE | X | 38 | 13.597 | 36.289 | 42.698 | 1.00 | 15.28 | C |
| ATOM | 235 | CG1 | ILE | X | 38 | 13.089 | 35.425 | 41.538 | 1.00 | 14.69 | C |
| ATOM | 236 | CD1 | ILE | X | 38 | 13.431 | 33.960 | 41.673 | 1.00 | 14.29 | C |
| ATOM | 237 | CG2 | ILE | X | 38 | 12.714 | 37.517 | 42.868 | 1.00 | 14.60 | C |
| ATOM | 238 | C | ILE | X | 38 | 16.072 | 35.529 | 42.607 | 1.00 | 15.56 | C |
| ATOM | 239 | O | ILE | X | 38 | 16.654 | 35.113 | 41.605 | 1.00 | 15.11 | O |

APPENDIX 1-continued

X-RAY DATA COORDINATES FOR LRP-220 (SEQ ID NO: 5)

| ATOM | 240 | N   | TYR | X | 39 | 16.279 | 35.028 | 43.818 | 1.00 | 15.67 | N |
|------|-----|-----|-----|---|----|--------|--------|--------|------|-------|---|
| ATOM | 241 | CA  | TYR | X | 39 | 17.228 | 33.950 | 44.042 | 1.00 | 15.96 | C |
| ATOM | 242 | CB  | TYR | X | 39 | 18.187 | 34.303 | 45.189 | 1.00 | 16.07 | C |
| ATOM | 243 | CG  | TYR | X | 39 | 19.314 | 33.315 | 45.370 | 1.00 | 16.45 | C |
| ATOM | 244 | CD1 | TYR | X | 39 | 20.390 | 33.287 | 44.493 | 1.00 | 15.53 | C |
| ATOM | 245 | CE1 | TYR | X | 39 | 21.435 | 32.370 | 44.652 | 1.00 | 16.33 | C |
| ATOM | 246 | CZ  | TYR | X | 39 | 21.406 | 31.467 | 45.709 | 1.00 | 16.89 | C |
| ATOM | 247 | OH  | TYR | X | 39 | 22.434 | 30.559 | 45.882 | 1.00 | 17.23 | O |
| ATOM | 248 | CE2 | TYR | X | 39 | 20.346 | 31.474 | 46.598 | 1.00 | 18.39 | C |
| ATOM | 249 | CD2 | TYR | X | 39 | 19.299 | 32.400 | 46.423 | 1.00 | 17.79 | C |
| ATOM | 250 | C   | TYR | X | 39 | 16.486 | 32.656 | 44.326 | 1.00 | 16.39 | C |
| ATOM | 251 | O   | TYR | X | 39 | 16.754 | 31.635 | 43.698 | 1.00 | 16.56 | O |
| ATOM | 252 | N   | LYS | X | 40 | 15.538 | 32.709 | 45.255 | 1.00 | 16.77 | N |
| ATOM | 253 | CA  | LYS | X | 40 | 14.749 | 31.542 | 45.619 | 1.00 | 18.18 | C |
| ATOM | 254 | CB  | LYS | X | 40 | 15.553 | 30.572 | 46.508 | 1.00 | 17.81 | C |
| ATOM | 255 | CG  | LYS | X | 40 | 16.002 | 31.115 | 47.861 | 1.00 | 19.20 | C |
| ATOM | 256 | CD  | LYS | X | 40 | 16.748 | 30.032 | 48.639 | 1.00 | 20.03 | C |
| ATOM | 257 | CE  | LYS | X | 40 | 17.819 | 30.608 | 49.544 | 1.00 | 23.88 | C |
| ATOM | 258 | NZ  | LYS | X | 40 | 17.274 | 31.054 | 50.853 | 1.00 | 27.30 | N |
| ATOM | 259 | C   | LYS | X | 40 | 13.452 | 31.939 | 46.301 | 1.00 | 18.48 | C |
| ATOM | 260 | O   | LYS | X | 40 | 13.217 | 33.116 | 46.591 | 1.00 | 18.10 | O |
| ATOM | 261 | N   | ARG | X | 41 | 12.614 | 30.941 | 46.545 | 1.00 | 19.31 | N |
| ATOM | 262 | CA  | ARG | X | 41 | 11.348 | 31.141 | 47.209 | 1.00 | 20.40 | C |
| ATOM | 263 | CB  | ARG | X | 41 | 10.195 | 30.819 | 46.255 | 1.00 | 20.38 | C |
| ATOM | 264 | CG  | ARG | X | 41 | 8.848  | 31.278 | 46.746 | 1.00 | 20.74 | C |
| ATOM | 265 | CD  | ARG | X | 41 | 7.710  | 30.805 | 45.855 | 1.00 | 21.62 | C |
| ATOM | 266 | NE  | ARG | X | 41 | 6.526  | 31.626 | 46.106 | 1.00 | 22.97 | N |
| ATOM | 267 | CZ  | ARG | X | 41 | 5.346  | 31.478 | 45.506 | 1.00 | 24.70 | C |
| ATOM | 268 | NH1 | ARG | X | 41 | 5.158  | 30.515 | 44.604 | 1.00 | 24.36 | N |
| ATOM | 269 | NH2 | ARG | X | 41 | 4.347  | 32.301 | 45.816 | 1.00 | 23.10 | N |
| ATOM | 270 | C   | ARG | X | 41 | 11.316 | 30.246 | 48.441 | 1.00 | 21.24 | C |
| ATOM | 271 | O   | ARG | X | 41 | 11.756 | 29.100 | 48.394 | 1.00 | 21.61 | O |
| ATOM | 272 | N   | LYS | X | 42 | 10.826 | 30.794 | 49.545 | 1.00 | 22.35 | N |
| ATOM | 273 | CA  | LYS | X | 42 | 10.681 | 30.067 | 50.802 | 1.00 | 23.26 | C |
| ATOM | 274 | CB  | LYS | X | 42 | 10.827 | 31.052 | 51.971 | 1.00 | 23.59 | C |
| ATOM | 275 | CG  | LYS | X | 42 | 12.228 | 31.651 | 52.133 | 1.00 | 25.84 | C |
| ATOM | 276 | CD  | LYS | X | 42 | 13.248 | 30.571 | 52.524 | 1.00 | 27.90 | C |
| ATOM | 277 | CE  | LYS | X | 42 | 14.568 | 31.194 | 52.942 | 1.00 | 30.69 | C |
| ATOM | 278 | NZ  | LYS | X | 42 | 15.575 | 30.186 | 53.410 | 1.00 | 30.76 | N |
| ATOM | 279 | C   | LYS | X | 42 | 9.318  | 29.365 | 50.872 | 1.00 | 23.30 | C |
| ATOM | 280 | O   | LYS | X | 42 | 8.410  | 29.685 | 50.095 | 1.00 | 23.09 | O |
| ATOM | 281 | N   | SER | X | 43 | 9.169  | 28.428 | 51.814 | 1.00 | 23.50 | N |
| ATOM | 282 | CA  | SER | X | 43 | 7.908  | 27.695 | 51.989 | 1.00 | 23.42 | C |
| ATOM | 283 | CB  | SER | X | 43 | 8.049  | 26.560 | 53.010 | 1.00 | 23.74 | C |
| ATOM | 284 | OG  | SER | X | 43 | 8.248  | 27.068 | 54.317 | 1.00 | 23.90 | O |
| ATOM | 285 | C   | SER | X | 43 | 6.737  | 28.609 | 52.357 | 1.00 | 23.27 | C |
| ATOM | 286 | O   | SER | X | 43 | 5.589  | 28.311 | 52.011 | 1.00 | 23.41 | O |
| ATOM | 287 | N   | ASP | X | 44 | 7.020  | 29.730 | 53.028 | 1.00 | 22.61 | N |
| ATOM | 288 | CA  | ASP | X | 44 | 5.976  | 30.734 | 53.285 | 1.00 | 22.23 | C |
| ATOM | 289 | CB  | ASP | X | 44 | 6.345  | 31.679 | 54.445 | 1.00 | 22.20 | C |
| ATOM | 290 | CG  | ASP | X | 44 | 7.537  | 32.597 | 54.136 | 1.00 | 22.55 | C |
| ATOM | 291 | OD1 | ASP | X | 44 | 8.189  | 32.457 | 53.077 | 1.00 | 22.52 | O |
| ATOM | 292 | OD2 | ASP | X | 44 | 7.825  | 33.472 | 54.982 | 1.00 | 22.35 | O |
| ATOM | 293 | C   | ASP | X | 44 | 5.568  | 31.518 | 52.033 | 1.00 | 22.07 | C |
| ATOM | 294 | O   | ASP | X | 44 | 4.736  | 32.426 | 52.108 | 1.00 | 22.37 | O |
| ATOM | 295 | N   | GLY | X | 45 | 6.153  | 31.164 | 50.890 | 1.00 | 21.50 | N |
| ATOM | 296 | CA  | GLY | X | 45 | 5.794  | 31.773 | 49.609 | 1.00 | 21.11 | C |
| ATOM | 297 | C   | GLY | X | 45 | 6.583  | 33.021 | 49.241 | 1.00 | 20.57 | C |
| ATOM | 298 | O   | GLY | X | 45 | 6.484  | 33.503 | 48.117 | 1.00 | 20.80 | O |
| ATOM | 299 | N   | ILE | X | 46 | 7.371  | 33.533 | 50.184 | 1.00 | 20.14 | N |
| ATOM | 300 | CA  | ILE | X | 46 | 8.111  | 34.777 | 50.001 | 1.00 | 19.66 | C |
| ATOM | 301 | CB  | ILE | X | 46 | 8.604  | 35.356 | 51.371 | 1.00 | 19.98 | C |
| ATOM | 302 | CG1 | ILE | X | 46 | 7.420  | 35.761 | 52.259 | 1.00 | 20.97 | C |
| ATOM | 303 | CD1 | ILE | X | 46 | 6.553  | 36.913 | 51.710 | 1.00 | 23.35 | C |
| ATOM | 304 | CG2 | ILE | X | 46 | 9.539  | 36.547 | 51.184 | 1.00 | 20.10 | C |
| ATOM | 305 | C   | ILE | X | 46 | 9.286  | 34.561 | 49.048 | 1.00 | 19.00 | C |
| ATOM | 306 | O   | ILE | X | 46 | 10.089 | 33.643 | 49.238 | 1.00 | 18.99 | O |
| ATOM | 307 | N   | TYR | X | 47 | 9.364  | 35.392 | 48.010 | 1.00 | 18.11 | N |
| ATOM | 308 | CA  | TYR | X | 47 | 10.515 | 35.391 | 47.103 | 1.00 | 17.53 | C |
| ATOM | 309 | CB  | TYR | X | 47 | 10.138 | 36.007 | 45.748 | 1.00 | 17.56 | C |
| ATOM | 310 | CG  | TYR | X | 47 | 9.407  | 35.050 | 44.833 | 1.00 | 17.37 | C |
| ATOM | 311 | CD1 | TYR | X | 47 | 10.105 | 34.085 | 44.108 | 1.00 | 16.49 | C |
| ATOM | 312 | CE1 | TYR | X | 47 | 9.450  | 33.203 | 43.273 | 1.00 | 17.17 | C |
| ATOM | 313 | CZ  | TYR | X | 47 | 8.072  | 33.270 | 43.148 | 1.00 | 17.59 | C |
| ATOM | 314 | OH  | TYR | X | 47 | 7.432  | 32.389 | 42.310 | 1.00 | 18.79 | O |
| ATOM | 315 | CE2 | TYR | X | 47 | 7.347  | 34.211 | 43.854 | 1.00 | 17.39 | C |
| ATOM | 316 | CD2 | TYR | X | 47 | 8.023  | 35.101 | 44.698 | 1.00 | 17.42 | C |
| ATOM | 317 | C   | TYR | X | 47 | 11.696 | 36.139 | 47.715 | 1.00 | 16.85 | C |

APPENDIX 1-continued

X-RAY DATA COORDINATES FOR LRP-220 (SEQ ID NO: 5)

| ATOM | 318 | O | TYR | X | 47 | 11.536 | 37.249 | 48.223 | 1.00 | 17.33 | O |
|---|---|---|---|---|---|---|---|---|---|---|---|
| ATOM | 319 | N | ILE | X | 48 | 12.874 | 35.523 | 47.673 | 1.00 | 16.11 | N |
| ATOM | 320 | CA | ILE | X | 48 | 14.098 | 36.150 | 48.153 | 1.00 | 15.38 | C |
| ATOM | 321 | CB | ILE | X | 48 | 15.071 | 35.132 | 48.821 | 1.00 | 15.62 | C |
| ATOM | 322 | CG1 | ILE | X | 48 | 14.403 | 34.388 | 49.998 | 1.00 | 15.96 | C |
| ATOM | 323 | CD1 | ILE | X | 48 | 13.777 | 35.287 | 51.092 | 1.00 | 16.52 | C |
| ATOM | 324 | CG2 | ILE | X | 48 | 16.367 | 35.813 | 49.263 | 1.00 | 14.67 | C |
| ATOM | 325 | C | ILE | X | 48 | 14.791 | 36.835 | 46.977 | 1.00 | 14.88 | C |
| ATOM | 326 | O | ILE | X | 48 | 15.053 | 36.204 | 45.954 | 1.00 | 14.80 | O |
| ATOM | 327 | N | ILE | X | 49 | 15.088 | 38.121 | 47.141 | 1.00 | 13.89 | N |
| ATOM | 328 | CA | ILE | X | 49 | 15.728 | 38.929 | 46.097 | 1.00 | 13.24 | C |
| ATOM | 329 | CB | ILE | X | 49 | 15.343 | 40.451 | 46.230 | 1.00 | 12.69 | C |
| ATOM | 330 | CG1 | ILE | X | 49 | 13.830 | 40.614 | 46.035 | 1.00 | 13.47 | C |
| ATOM | 331 | CD1 | ILE | X | 49 | 13.267 | 41.935 | 46.489 | 1.00 | 13.63 | C |
| ATOM | 332 | CG2 | ILE | X | 49 | 16.090 | 41.313 | 45.203 | 1.00 | 12.29 | C |
| ATOM | 333 | C | ILE | X | 49 | 17.242 | 38.727 | 46.109 | 1.00 | 12.73 | C |
| ATOM | 334 | O | ILE | X | 49 | 17.871 | 38.772 | 47.163 | 1.00 | 12.68 | O |
| ATOM | 335 | N | ASN | X | 50 | 17.818 | 38.504 | 44.930 | 1.00 | 12.16 | N |
| ATOM | 336 | CA | ASN | X | 50 | 19.262 | 38.393 | 44.785 | 1.00 | 12.01 | C |
| ATOM | 337 | CB | ASN | X | 50 | 19.611 | 37.753 | 43.432 | 1.00 | 11.98 | C |
| ATOM | 338 | CG | ASN | X | 50 | 21.079 | 37.331 | 43.320 | 1.00 | 11.89 | C |
| ATOM | 339 | OD1 | ASN | X | 50 | 21.404 | 36.384 | 42.600 | 1.00 | 15.09 | O |
| ATOM | 340 | ND2 | ASN | X | 50 | 21.960 | 38.018 | 44.025 | 1.00 | 9.56 | N |
| ATOM | 341 | C | ASN | X | 50 | 19.918 | 39.780 | 44.929 | 1.00 | 12.37 | C |
| ATOM | 342 | O | ASN | X | 50 | 19.870 | 40.605 | 44.004 | 1.00 | 11.20 | O |
| ATOM | 343 | N | LEU | X | 51 | 20.538 | 40.004 | 46.090 | 1.00 | 12.23 | N |
| ATOM | 344 | CA | LEU | X | 51 | 21.182 | 41.277 | 46.440 | 1.00 | 13.15 | C |
| ATOM | 345 | CB | LEU | X | 51 | 21.624 | 41.252 | 47.902 | 1.00 | 13.20 | C |
| ATOM | 346 | CG | LEU | X | 51 | 20.766 | 41.890 | 49.001 | 1.00 | 15.03 | C |
| ATOM | 347 | CD1 | LEU | X | 51 | 19.297 | 42.120 | 48.658 | 1.00 | 14.89 | C |
| ATOM | 348 | CD2 | LEU | X | 51 | 20.920 | 41.148 | 50.315 | 1.00 | 15.20 | C |
| ATOM | 349 | C | LEU | X | 51 | 22.360 | 41.684 | 45.555 | 1.00 | 13.09 | C |
| ATOM | 350 | O | LEU | X | 51 | 22.717 | 42.860 | 45.495 | 1.00 | 13.04 | O |
| ATOM | 351 | N | LYS | X | 52 | 22.975 | 40.721 | 44.882 | 1.00 | 13.36 | N |
| ATOM | 352 | CA | LYS | X | 52 | 23.986 | 41.046 | 43.876 | 1.00 | 14.10 | C |
| ATOM | 353 | CB | LYS | X | 52 | 24.653 | 39.779 | 43.329 | 1.00 | 14.53 | C |
| ATOM | 354 | CG | LYS | X | 52 | 25.619 | 39.113 | 44.309 | 1.00 | 16.50 | C |
| ATOM | 355 | CD | LYS | X | 52 | 25.517 | 37.577 | 44.252 | 1.00 | 20.60 | C |
| ATOM | 356 | CE | LYS | X | 52 | 26.405 | 36.971 | 43.201 | 1.00 | 22.69 | C |
| ATOM | 357 | NZ | LYS | X | 52 | 26.297 | 35.476 | 43.131 | 1.00 | 23.72 | N |
| ATOM | 358 | C | LYS | X | 52 | 23.349 | 41.867 | 42.745 | 1.00 | 13.64 | C |
| ATOM | 359 | O | LYS | X | 52 | 23.946 | 42.828 | 42.260 | 1.00 | 13.63 | O |
| ATOM | 360 | N | ARG | X | 53 | 22.130 | 41.497 | 42.353 | 1.00 | 13.36 | N |
| ATOM | 361 | CA | ARG | X | 53 | 21.369 | 42.255 | 41.355 | 1.00 | 13.56 | C |
| ATOM | 362 | CB | ARG | X | 53 | 20.117 | 41.489 | 40.896 | 1.00 | 13.45 | C |
| ATOM | 363 | CG | ARG | X | 53 | 20.372 | 40.050 | 40.410 | 1.00 | 14.27 | C |
| ATOM | 364 | CD | ARG | X | 53 | 21.123 | 40.001 | 39.089 | 1.00 | 16.18 | C |
| ATOM | 365 | NE | ARG | X | 53 | 22.574 | 40.044 | 39.260 | 1.00 | 18.49 | N |
| ATOM | 366 | CZ | ARG | X | 53 | 23.343 | 38.984 | 39.506 | 1.00 | 20.09 | C |
| ATOM | 367 | NH1 | ARG | X | 53 | 22.810 | 37.774 | 39.625 | 1.00 | 21.57 | N |
| ATOM | 368 | NH2 | ARG | X | 53 | 24.657 | 39.135 | 39.639 | 1.00 | 21.70 | N |
| ATOM | 369 | C | ARG | X | 53 | 20.980 | 43.631 | 41.891 | 1.00 | 13.43 | C |
| ATOM | 370 | O | ARG | X | 53 | 21.130 | 44.629 | 41.187 | 1.00 | 14.11 | O |
| ATOM | 371 | N | THR | X | 54 | 20.478 | 43.677 | 43.125 | 1.00 | 13.10 | N |
| ATOM | 372 | CA | THR | X | 54 | 20.211 | 44.945 | 43.823 | 1.00 | 12.92 | C |
| ATOM | 373 | CB | THR | X | 54 | 19.922 | 44.718 | 45.334 | 1.00 | 12.81 | C |
| ATOM | 374 | OG1 | THR | X | 54 | 18.834 | 43.803 | 45.479 | 1.00 | 11.60 | O |
| ATOM | 375 | CG2 | THR | X | 54 | 19.571 | 46.037 | 46.059 | 1.00 | 12.38 | C |
| ATOM | 376 | C | THR | X | 54 | 21.408 | 45.885 | 43.660 | 1.00 | 13.18 | C |
| ATOM | 377 | O | THR | X | 54 | 21.251 | 47.019 | 43.188 | 1.00 | 13.06 | O |
| ATOM | 378 | N | TRP | X | 55 | 22.597 | 45.386 | 44.007 | 1.00 | 13.14 | N |
| ATOM | 379 | CA | TRP | X | 55 | 23.834 | 46.177 | 43.975 | 1.00 | 13.60 | C |
| ATOM | 380 | CB | TRP | X | 55 | 24.991 | 45.418 | 44.642 | 1.00 | 14.08 | C |
| ATOM | 381 | CG | TRP | X | 55 | 26.302 | 46.143 | 44.585 | 1.00 | 14.58 | C |
| ATOM | 382 | CD1 | TRP | X | 55 | 27.410 | 45.786 | 43.866 | 1.00 | 15.56 | C |
| ATOM | 383 | NE1 | TRP | X | 55 | 28.417 | 46.699 | 44.063 | 1.00 | 15.28 | N |
| ATOM | 384 | CE2 | TRP | X | 55 | 27.976 | 47.669 | 44.925 | 1.00 | 15.31 | C |
| ATOM | 385 | CD2 | TRP | X | 55 | 26.643 | 47.351 | 45.276 | 1.00 | 15.17 | C |
| ATOM | 386 | CE3 | TRP | X | 55 | 25.948 | 48.199 | 46.155 | 1.00 | 15.54 | C |
| ATOM | 387 | CZ3 | TRP | X | 55 | 26.600 | 49.324 | 46.650 | 1.00 | 15.72 | C |
| ATOM | 388 | CH2 | TRP | X | 55 | 27.932 | 49.617 | 46.275 | 1.00 | 15.84 | C |
| ATOM | 389 | CZ2 | TRP | X | 55 | 28.631 | 48.803 | 45.416 | 1.00 | 15.28 | C |
| ATOM | 390 | C | TRP | X | 55 | 24.232 | 46.637 | 42.572 | 1.00 | 13.85 | C |
| ATOM | 391 | O | TRP | X | 55 | 24.554 | 47.807 | 42.382 | 1.00 | 13.66 | O |
| ATOM | 392 | N | GLU | X | 56 | 24.210 | 45.717 | 41.606 | 1.00 | 14.15 | N |
| ATOM | 393 | CA | GLU | X | 56 | 24.508 | 46.040 | 40.204 | 1.00 | 15.20 | C |
| ATOM | 394 | CB | GLU | X | 56 | 24.413 | 44.790 | 39.326 | 1.00 | 15.32 | C |
| ATOM | 395 | CG | GLU | X | 56 | 25.568 | 43.814 | 39.528 | 1.00 | 18.48 | C |

APPENDIX 1-continued

X-RAY DATA COORDINATES FOR LRP-220 (SEQ ID NO: 5)

| ATOM | 396 | CD | GLU | X | 56 | 25.240 | 42.386 | 39.086 | 1.00 | 22.64 | C |
|------|-----|-----|-----|---|----|--------|--------|--------|------|-------|---|
| ATOM | 397 | OE1 | GLU | X | 56 | 24.247 | 42.186 | 38.337 | 1.00 | 22.16 | O |
| ATOM | 398 | OE2 | GLU | X | 56 | 25.995 | 41.466 | 39.485 | 1.00 | 23.38 | O |
| ATOM | 399 | C | GLU | X | 56 | 23.595 | 47.133 | 39.641 | 1.00 | 15.01 | C |
| ATOM | 400 | O | GLU | X | 56 | 24.061 | 48.052 | 38.966 | 1.00 | 15.02 | O |
| ATOM | 401 | N | LYS | X | 57 | 22.300 | 47.024 | 39.929 | 1.00 | 15.07 | N |
| ATOM | 402 | CA | LYS | X | 57 | 21.301 | 47.966 | 39.421 | 1.00 | 15.43 | C |
| ATOM | 403 | CB | LYS | X | 57 | 19.895 | 47.381 | 39.561 | 1.00 | 15.35 | C |
| ATOM | 404 | CG | LYS | X | 57 | 19.644 | 46.192 | 38.645 | 1.00 | 16.72 | C |
| ATOM | 405 | CD | LYS | X | 57 | 20.010 | 46.521 | 37.202 | 1.00 | 17.47 | C |
| ATOM | 406 | CE | LYS | X | 57 | 19.612 | 45.391 | 36.285 | 1.00 | 19.69 | C |
| ATOM | 407 | NZ | LYS | X | 57 | 20.159 | 45.554 | 34.911 | 1.00 | 21.09 | N |
| ATOM | 408 | C | LYS | X | 57 | 21.389 | 49.322 | 40.110 | 1.00 | 15.45 | C |
| ATOM | 409 | O | LYS | X | 57 | 21.097 | 50.357 | 39.513 | 1.00 | 15.28 | O |
| ATOM | 410 | N | LEU | X | 58 | 21.802 | 49.304 | 41.370 | 1.00 | 15.48 | N |
| ATOM | 411 | CA | LEU | X | 58 | 22.019 | 50.522 | 42.121 | 1.00 | 16.23 | C |
| ATOM | 412 | CB | LEU | X | 58 | 22.405 | 50.146 | 43.543 | 1.00 | 17.25 | C |
| ATOM | 413 | CG | LEU | X | 58 | 21.910 | 50.978 | 44.706 | 1.00 | 19.86 | C |
| ATOM | 414 | CD1 | LEU | X | 58 | 21.822 | 50.054 | 45.930 | 1.00 | 21.77 | C |
| ATOM | 415 | CD2 | LEU | X | 58 | 22.918 | 52.098 | 44.920 | 1.00 | 23.61 | C |
| ATOM | 416 | C | LEU | X | 58 | 23.135 | 51.343 | 41.465 | 1.00 | 15.84 | C |
| ATOM | 417 | O | LEU | X | 58 | 23.023 | 52.564 | 41.329 | 1.00 | 15.44 | O |
| ATOM | 418 | N | LEU | X | 59 | 24.197 | 50.650 | 41.050 | 1.00 | 15.30 | N |
| ATOM | 419 | CA | LEU | X | 59 | 25.343 | 51.274 | 40.381 | 1.00 | 15.32 | C |
| ATOM | 420 | CB | LEU | X | 59 | 26.525 | 50.298 | 40.299 | 1.00 | 15.39 | C |
| ATOM | 421 | CG | LEU | X | 59 | 27.225 | 49.909 | 41.609 | 1.00 | 16.30 | C |
| ATOM | 422 | CD1 | LEU | X | 59 | 28.361 | 48.954 | 41.304 | 1.00 | 17.87 | C |
| ATOM | 423 | CD2 | LEU | X | 59 | 27.759 | 51.147 | 42.346 | 1.00 | 17.69 | C |
| ATOM | 424 | C | LEU | X | 59 | 24.984 | 51.781 | 38.990 | 1.00 | 14.82 | C |
| ATOM | 425 | O | LEU | X | 59 | 25.414 | 52.862 | 38.596 | 1.00 | 14.71 | O |
| ATOM | 426 | N | LEU | X | 60 | 24.200 | 50.990 | 38.258 | 1.00 | 14.35 | N |
| ATOM | 427 | CA | LEU | X | 60 | 23.679 | 51.394 | 36.956 | 1.00 | 14.01 | C |
| ATOM | 428 | CB | LEU | X | 60 | 22.914 | 50.241 | 36.303 | 1.00 | 14.39 | C |
| ATOM | 429 | CG | LEU | X | 60 | 22.455 | 50.460 | 34.858 | 1.00 | 16.16 | C |
| ATOM | 430 | CD1 | LEU | X | 60 | 23.637 | 50.340 | 33.877 | 1.00 | 18.26 | C |
| ATOM | 431 | CD2 | LEU | X | 60 | 21.356 | 49.482 | 34.489 | 1.00 | 18.54 | C |
| ATOM | 432 | C | LEU | X | 60 | 22.786 | 52.642 | 37.079 | 1.00 | 13.61 | C |
| ATOM | 433 | O | LEU | X | 60 | 22.914 | 53.578 | 36.287 | 1.00 | 13.71 | O |
| ATOM | 434 | N | ALA | X | 61 | 21.897 | 52.655 | 38.073 | 1.00 | 12.97 | N |
| ATOM | 435 | CA | ALA | X | 61 | 21.060 | 53.822 | 38.350 | 1.00 | 13.04 | C |
| ATOM | 436 | CB | ALA | X | 61 | 20.036 | 53.513 | 39.434 | 1.00 | 12.61 | C |
| ATOM | 437 | C | ALA | X | 61 | 21.877 | 55.066 | 38.719 | 1.00 | 13.02 | C |
| ATOM | 438 | O | ALA | X | 61 | 21.594 | 56.151 | 38.222 | 1.00 | 13.00 | O |
| ATOM | 439 | N | ALA | X | 62 | 22.885 | 54.898 | 39.578 | 1.00 | 13.18 | N |
| ATOM | 440 | CA | ALA | X | 62 | 23.757 | 56.007 | 40.009 | 1.00 | 13.51 | C |
| ATOM | 441 | CB | ALA | X | 62 | 24.732 | 55.538 | 41.105 | 1.00 | 12.76 | C |
| ATOM | 442 | C | ALA | X | 62 | 24.520 | 56.616 | 38.831 | 1.00 | 13.73 | C |
| ATOM | 443 | O | ALA | X | 62 | 24.645 | 57.834 | 38.728 | 1.00 | 14.07 | O |
| ATOM | 444 | N | ARG | X | 63 | 25.010 | 55.752 | 37.946 | 1.00 | 14.22 | N |
| ATOM | 445 | CA | ARG | X | 63 | 25.668 | 56.151 | 36.709 | 1.00 | 15.34 | C |
| ATOM | 446 | CB | ARG | X | 63 | 26.095 | 54.903 | 35.946 | 1.00 | 15.87 | C |
| ATOM | 447 | CG | ARG | X | 63 | 27.355 | 55.055 | 35.133 | 1.00 | 20.75 | C |
| ATOM | 448 | CD | ARG | X | 63 | 27.822 | 53.685 | 34.630 | 1.00 | 27.61 | C |
| ATOM | 449 | NE | ARG | X | 63 | 28.044 | 52.743 | 35.733 | 1.00 | 31.32 | N |
| ATOM | 450 | CZ | ARG | X | 63 | 27.836 | 51.430 | 35.658 | 1.00 | 33.90 | C |
| ATOM | 451 | NH1 | ARG | X | 63 | 27.385 | 50.879 | 34.533 | 1.00 | 35.78 | N |
| ATOM | 452 | NH2 | ARG | X | 63 | 28.070 | 50.662 | 36.714 | 1.00 | 34.66 | N |
| ATOM | 453 | C | ARG | X | 63 | 24.760 | 57.011 | 35.836 | 1.00 | 14.90 | C |
| ATOM | 454 | O | ARG | X | 63 | 25.177 | 58.068 | 35.357 | 1.00 | 15.56 | O |
| ATOM | 455 | N | ALA | X | 64 | 23.520 | 56.561 | 35.647 | 1.00 | 14.15 | N |
| ATOM | 456 | CA | ALA | X | 64 | 22.511 | 57.289 | 34.861 | 1.00 | 13.71 | C |
| ATOM | 457 | CB | ALA | X | 64 | 21.251 | 56.435 | 34.699 | 1.00 | 13.54 | C |
| ATOM | 458 | C | ALA | X | 64 | 22.148 | 58.638 | 35.478 | 1.00 | 13.18 | C |
| ATOM | 459 | O | ALA | X | 64 | 21.916 | 59.619 | 34.766 | 1.00 | 12.87 | O |
| ATOM | 460 | N | ILE | X | 65 | 22.079 | 58.668 | 36.804 | 1.00 | 12.69 | N |
| ATOM | 461 | CA | ILE | X | 65 | 21.784 | 59.892 | 37.550 | 1.00 | 12.18 | C |
| ATOM | 462 | CB | ILE | X | 65 | 21.468 | 59.566 | 39.040 | 1.00 | 12.27 | C |
| ATOM | 463 | CG1 | ILE | X | 65 | 20.078 | 58.909 | 39.159 | 1.00 | 11.23 | C |
| ATOM | 464 | CD1 | ILE | X | 65 | 19.843 | 58.174 | 40.493 | 1.00 | 11.69 | C |
| ATOM | 465 | CG2 | ILE | X | 65 | 21.583 | 60.823 | 39.921 | 1.00 | 10.47 | C |
| ATOM | 466 | C | ILE | X | 65 | 22.939 | 60.897 | 37.416 | 1.00 | 12.50 | C |
| ATOM | 467 | O | ILE | X | 65 | 22.713 | 62.084 | 37.162 | 1.00 | 12.85 | O |
| ATOM | 468 | N | VAL | X | 66 | 24.166 | 60.401 | 37.544 | 1.00 | 12.58 | N |
| ATOM | 469 | CA | VAL | X | 66 | 25.378 | 61.223 | 37.451 | 1.00 | 12.76 | C |
| ATOM | 470 | CB | VAL | X | 66 | 26.639 | 60.425 | 37.937 | 1.00 | 12.82 | C |
| ATOM | 471 | CG1 | VAL | X | 66 | 27.954 | 61.116 | 37.565 | 1.00 | 14.01 | C |
| ATOM | 472 | CG2 | VAL | X | 66 | 26.581 | 60.210 | 39.452 | 1.00 | 12.58 | C |
| ATOM | 473 | C | VAL | X | 66 | 25.555 | 61.847 | 36.047 | 1.00 | 13.21 | C |

APPENDIX 1-continued

X-RAY DATA COORDINATES FOR LRP-220 (SEQ ID NO: 5)

| ATOM | 474 | O | VAL | X | 66 | 26.067 | 62.965 | 35.925 | 1.00 | 13.31 | O |
|------|-----|-----|-----|---|----|--------|--------|--------|------|-------|---|
| ATOM | 475 | N | ALA | X | 67 | 25.104 | 61.139 | 35.007 | 1.00 | 13.01 | N |
| ATOM | 476 | CA | ALA | X | 67 | 25.190 | 61.637 | 33.630 | 1.00 | 13.38 | C |
| ATOM | 477 | CB | ALA | X | 67 | 24.905 | 60.515 | 32.623 | 1.00 | 12.82 | C |
| ATOM | 478 | C | ALA | X | 67 | 24.307 | 62.863 | 33.336 | 1.00 | 13.48 | C |
| ATOM | 479 | O | ALA | X | 67 | 24.474 | 63.505 | 32.300 | 1.00 | 14.15 | O |
| ATOM | 480 | N | ILE | X | 68 | 23.368 | 63.168 | 34.225 | 1.00 | 13.54 | N |
| ATOM | 481 | CA | ILE | X | 68 | 22.514 | 64.349 | 34.071 | 1.00 | 13.57 | C |
| ATOM | 482 | CB | ILE | X | 68 | 21.162 | 64.209 | 34.824 | 1.00 | 13.49 | C |
| ATOM | 483 | CG1 | ILE | X | 68 | 20.448 | 62.901 | 34.446 | 1.00 | 12.37 | C |
| ATOM | 484 | CD1 | ILE | X | 68 | 20.133 | 62.737 | 32.955 | 1.00 | 11.55 | C |
| ATOM | 485 | CG2 | ILE | X | 68 | 20.266 | 65.423 | 34.558 | 1.00 | 13.63 | C |
| ATOM | 486 | C | ILE | X | 68 | 23.281 | 65.566 | 34.573 | 1.00 | 13.94 | C |
| ATOM | 487 | O | ILE | X | 68 | 23.572 | 65.677 | 35.769 | 1.00 | 13.16 | O |
| ATOM | 488 | N | GLU | X | 69 | 23.595 | 66.466 | 33.639 | 1.00 | 14.41 | N |
| ATOM | 489 | CA | GLU | X | 69 | 24.566 | 67.544 | 33.850 | 1.00 | 15.27 | C |
| ATOM | 490 | CB | GLU | X | 69 | 24.909 | 68.221 | 32.518 | 1.00 | 15.50 | C |
| ATOM | 491 | CG | GLU | X | 69 | 25.639 | 67.334 | 31.504 | 1.00 | 16.60 | C |
| ATOM | 492 | CD | GLU | X | 69 | 24.703 | 66.604 | 30.543 | 1.00 | 17.99 | C |
| ATOM | 493 | OE1 | GLU | X | 69 | 23.567 | 66.236 | 30.933 | 1.00 | 19.61 | O |
| ATOM | 494 | OE2 | GLU | X | 69 | 25.109 | 66.388 | 29.384 | 1.00 | 18.22 | O |
| ATOM | 495 | C | GLU | X | 69 | 24.121 | 68.584 | 34.886 | 1.00 | 15.47 | C |
| ATOM | 496 | O | GLU | X | 69 | 24.940 | 69.068 | 35.672 | 1.00 | 15.95 | O |
| ATOM | 497 | N | ASN | X | 70 | 22.836 | 68.933 | 34.882 | 1.00 | 15.17 | N |
| ATOM | 498 | CA | ASN | X | 70 | 22.275 | 69.751 | 35.949 | 1.00 | 15.17 | C |
| ATOM | 499 | CB | ASN | X | 70 | 21.362 | 70.836 | 35.367 | 1.00 | 15.33 | C |
| ATOM | 500 | CG | ASN | X | 70 | 20.632 | 71.646 | 36.432 | 1.00 | 15.56 | C |
| ATOM | 501 | OD1 | ASN | X | 70 | 20.926 | 71.565 | 37.620 | 1.00 | 15.17 | O |
| ATOM | 502 | ND2 | ASN | X | 70 | 19.676 | 72.446 | 35.993 | 1.00 | 17.62 | N |
| ATOM | 503 | C | ASN | X | 70 | 21.544 | 68.860 | 36.967 | 1.00 | 14.90 | C |
| ATOM | 504 | O | ASN | X | 70 | 20.503 | 68.285 | 36.650 | 1.00 | 14.79 | O |
| ATOM | 505 | N | PRO | X | 71 | 22.089 | 68.753 | 38.198 | 1.00 | 14.79 | N |
| ATOM | 506 | CA | PRO | X | 71 | 21.547 | 67.844 | 39.229 | 1.00 | 14.65 | C |
| ATOM | 507 | CB | PRO | X | 71 | 22.345 | 68.215 | 40.485 | 1.00 | 14.84 | C |
| ATOM | 508 | CG | PRO | X | 71 | 23.598 | 68.814 | 39.977 | 1.00 | 15.24 | C |
| ATOM | 509 | CD | PRO | X | 71 | 23.256 | 69.508 | 38.692 | 1.00 | 14.41 | C |
| ATOM | 510 | C | PRO | X | 71 | 20.048 | 68.032 | 39.488 | 1.00 | 14.30 | C |
| ATOM | 511 | O | PRO | X | 71 | 19.350 | 67.070 | 39.814 | 1.00 | 13.78 | O |
| ATOM | 512 | N | ALA | X | 72 | 19.561 | 69.261 | 39.327 | 1.00 | 14.03 | N |
| ATOM | 513 | CA | ALA | X | 72 | 18.148 | 69.576 | 39.557 | 1.00 | 13.57 | C |
| ATOM | 514 | CB | ALA | X | 72 | 17.938 | 71.093 | 39.614 | 1.00 | 13.64 | C |
| ATOM | 515 | C | ALA | X | 72 | 17.210 | 68.940 | 38.529 | 1.00 | 13.40 | C |
| ATOM | 516 | O | ALA | X | 72 | 16.008 | 68.825 | 38.781 | 1.00 | 13.23 | O |
| ATOM | 517 | N | ASP | X | 73 | 17.762 | 68.539 | 37.379 | 1.00 | 13.19 | N |
| ATOM | 518 | CA | ASP | X | 73 | 16.992 | 67.870 | 36.320 | 1.00 | 13.44 | C |
| ATOM | 519 | CB | ASP | X | 73 | 17.671 | 68.055 | 34.960 | 1.00 | 13.55 | C |
| ATOM | 520 | CG | ASP | X | 73 | 17.528 | 69.477 | 34.437 | 1.00 | 14.70 | C |
| ATOM | 521 | OD1 | ASP | X | 73 | 16.559 | 70.147 | 34.841 | 1.00 | 16.45 | O |
| ATOM | 522 | OD2 | ASP | X | 73 | 18.368 | 69.922 | 33.628 | 1.00 | 15.65 | O |
| ATOM | 523 | C | ASP | X | 73 | 16.697 | 66.387 | 36.591 | 1.00 | 13.25 | C |
| ATOM | 524 | O | ASP | X | 73 | 16.021 | 65.727 | 35.797 | 1.00 | 13.01 | O |
| ATOM | 525 | N | VAL | X | 74 | 17.209 | 65.880 | 37.711 | 1.00 | 12.99 | N |
| ATOM | 526 | CA | VAL | X | 74 | 16.795 | 64.586 | 38.237 | 1.00 | 12.95 | C |
| ATOM | 527 | CB | VAL | X | 74 | 17.971 | 63.819 | 38.895 | 1.00 | 13.13 | C |
| ATOM | 528 | CG1 | VAL | X | 74 | 17.539 | 62.414 | 39.346 | 1.00 | 12.75 | C |
| ATOM | 529 | CG2 | VAL | X | 74 | 19.169 | 63.731 | 37.938 | 1.00 | 12.47 | C |
| ATOM | 530 | C | VAL | X | 74 | 15.671 | 64.841 | 39.251 | 1.00 | 13.27 | C |
| ATOM | 531 | O | VAL | X | 74 | 15.836 | 65.580 | 40.226 | 1.00 | 13.05 | O |
| ATOM | 532 | N | SER | X | 75 | 14.517 | 64.245 | 38.997 | 1.00 | 13.48 | N |
| ATOM | 533 | CA | SER | X | 75 | 13.410 | 64.310 | 39.943 | 1.00 | 14.21 | C |
| ATOM | 534 | CB | SER | X | 75 | 12.126 | 64.728 | 39.231 | 1.00 | 13.94 | C |
| ATOM | 535 | OG | SER | X | 75 | 10.986 | 64.155 | 39.843 | 1.00 | 17.96 | O |
| ATOM | 536 | C | SER | X | 75 | 13.266 | 62.989 | 40.705 | 1.00 | 13.94 | C |
| ATOM | 537 | O | SER | X | 75 | 13.394 | 61.896 | 40.128 | 1.00 | 13.38 | O |
| ATOM | 538 | N | VAL | X | 76 | 13.060 | 63.104 | 42.015 | 1.00 | 14.01 | N |
| ATOM | 539 | CA | VAL | X | 76 | 13.006 | 61.945 | 42.903 | 1.00 | 14.17 | C |
| ATOM | 540 | CB | VAL | X | 76 | 14.258 | 61.840 | 43.833 | 1.00 | 14.24 | C |
| ATOM | 541 | CG1 | VAL | X | 76 | 15.510 | 61.544 | 43.024 | 1.00 | 13.27 | C |
| ATOM | 542 | CG2 | VAL | X | 76 | 14.470 | 63.113 | 44.659 | 1.00 | 14.71 | C |
| ATOM | 543 | C | VAL | X | 76 | 11.697 | 61.946 | 43.688 | 1.00 | 14.94 | C |
| ATOM | 544 | O | VAL | X | 76 | 11.314 | 62.960 | 44.290 | 1.00 | 15.09 | O |
| ATOM | 545 | N | ILE | X | 77 | 11.014 | 60.806 | 43.674 | 1.00 | 15.08 | N |
| ATOM | 546 | CA | ILE | X | 77 | 9.609 | 60.757 | 44.050 | 1.00 | 16.01 | C |
| ATOM | 547 | CB | ILE | X | 77 | 8.717 | 60.627 | 42.769 | 1.00 | 16.14 | C |
| ATOM | 548 | CG1 | ILE | X | 77 | 8.608 | 61.995 | 42.082 | 1.00 | 16.19 | C |
| ATOM | 549 | CD1 | ILE | X | 77 | 7.766 | 62.027 | 40.836 | 1.00 | 16.94 | C |
| ATOM | 550 | CG2 | ILE | X | 77 | 7.342 | 60.053 | 43.094 | 1.00 | 16.76 | C |
| ATOM | 551 | C | ILE | X | 77 | 9.261 | 59.679 | 45.088 | 1.00 | 16.04 | C |

APPENDIX 1-continued

X-RAY DATA COORDINATES FOR LRP-220 (SEQ ID NO: 5)

| ATOM | 552 | O | ILE | X | 77 | 9.762 | 58.556 | 45.028 | 1.00 | 15.42 | O |
|---|---|---|---|---|---|---|---|---|---|---|---|
| ATOM | 553 | N | SER | X | 78 | 8.418 | 60.062 | 46.051 | 1.00 | 16.33 | N |
| ATOM | 554 | CA | SER | X | 78 | 7.701 | 59.114 | 46.899 | 1.00 | 16.87 | C |
| ATOM | 555 | CB | SER | X | 78 | 8.521 | 58.707 | 48.128 | 1.00 | 16.62 | C |
| ATOM | 556 | OG | SER | X | 78 | 7.830 | 57.701 | 48.858 | 1.00 | 16.57 | O |
| ATOM | 557 | C | SER | X | 78 | 6.358 | 59.684 | 47.346 | 1.00 | 17.55 | C |
| ATOM | 558 | O | SER | X | 78 | 6.314 | 60.640 | 48.124 | 1.00 | 17.61 | O |
| ATOM | 559 | N | SER | X | 79 | 5.267 | 59.096 | 46.858 | 1.00 | 18.08 | N |
| ATOM | 560 | CA | SER | X | 79 | 3.942 | 59.458 | 47.347 | 1.00 | 19.01 | C |
| ATOM | 561 | CB | SER | X | 79 | 2.848 | 58.949 | 46.405 | 1.00 | 18.84 | C |
| ATOM | 562 | OG | SER | X | 79 | 2.953 | 57.547 | 46.234 | 1.00 | 19.69 | O |
| ATOM | 563 | C | SER | X | 79 | 3.743 | 58.903 | 48.759 | 1.00 | 19.52 | C |
| ATOM | 564 | O | SER | X | 79 | 3.237 | 59.598 | 49.640 | 1.00 | 19.93 | O |
| ATOM | 565 | N | ARG | X | 80 | 4.157 | 57.651 | 48.964 | 1.00 | 19.99 | N |
| ATOM | 566 | CA | ARG | X | 80 | 4.089 | 57.001 | 50.271 | 1.00 | 20.49 | C |
| ATOM | 567 | CB | ARG | X | 80 | 4.571 | 55.554 | 50.179 | 1.00 | 20.42 | C |
| ATOM | 568 | CG | ARG | X | 80 | 3.621 | 54.609 | 49.468 | 1.00 | 21.68 | C |
| ATOM | 569 | CD | ARG | X | 80 | 4.310 | 53.283 | 49.195 | 1.00 | 22.90 | C |
| ATOM | 570 | NE | ARG | X | 80 | 4.730 | 52.633 | 50.438 | 1.00 | 23.52 | N |
| ATOM | 571 | CZ | ARG | X | 80 | 5.811 | 51.863 | 50.565 | 1.00 | 23.95 | C |
| ATOM | 572 | NH1 | ARG | X | 80 | 6.602 | 51.639 | 49.520 | 1.00 | 23.31 | N |
| ATOM | 573 | NH2 | ARG | X | 80 | 6.101 | 51.320 | 51.743 | 1.00 | 22.97 | N |
| ATOM | 574 | C | ARG | X | 80 | 4.940 | 57.717 | 51.299 | 1.00 | 20.48 | C |
| ATOM | 575 | O | ARG | X | 80 | 6.076 | 58.110 | 51.005 | 1.00 | 20.45 | O |
| ATOM | 576 | N | ASN | X | 81 | 4.396 | 57.853 | 52.507 | 1.00 | 20.64 | N |
| ATOM | 577 | CA | ASN | X | 81 | 5.142 | 58.389 | 53.654 | 1.00 | 21.24 | C |
| ATOM | 578 | CB | ASN | X | 81 | 4.277 | 58.390 | 54.934 | 1.00 | 21.91 | C |
| ATOM | 579 | CG | ASN | X | 81 | 3.675 | 57.020 | 55.258 | 1.00 | 24.36 | C |
| ATOM | 580 | OD1 | ASN | X | 81 | 3.899 | 56.027 | 54.548 | 1.00 | 26.64 | O |
| ATOM | 581 | ND2 | ASN | X | 81 | 2.888 | 56.964 | 56.344 | 1.00 | 27.50 | N |
| ATOM | 582 | C | ASN | X | 81 | 6.472 | 57.678 | 53.901 | 1.00 | 20.73 | C |
| ATOM | 583 | O | ASN | X | 81 | 7.453 | 58.306 | 54.297 | 1.00 | 20.84 | O |
| ATOM | 584 | N | THR | X | 82 | 6.485 | 56.371 | 53.637 | 1.00 | 20.42 | N |
| ATOM | 585 | CA | THR | X | 82 | 7.645 | 55.499 | 53.820 | 1.00 | 20.15 | C |
| ATOM | 586 | CB | THR | X | 82 | 7.341 | 54.095 | 53.257 | 1.00 | 20.31 | C |
| ATOM | 587 | OG1 | THR | X | 82 | 6.038 | 53.671 | 53.690 | 1.00 | 20.62 | O |
| ATOM | 588 | CG2 | THR | X | 82 | 8.378 | 53.085 | 53.707 | 1.00 | 20.00 | C |
| ATOM | 589 | C | THR | X | 82 | 8.927 | 56.034 | 53.165 | 1.00 | 19.82 | C |
| ATOM | 590 | O | THR | X | 82 | 10.017 | 55.909 | 53.730 | 1.00 | 20.22 | O |
| ATOM | 591 | N | GLY | X | 83 | 8.799 | 56.636 | 51.984 | 1.00 | 19.24 | N |
| ATOM | 592 | CA | GLY | X | 83 | 9.968 | 57.147 | 51.264 | 1.00 | 18.71 | C |
| ATOM | 593 | C | GLY | X | 83 | 10.131 | 58.655 | 51.220 | 1.00 | 18.35 | C |
| ATOM | 594 | O | GLY | X | 83 | 11.050 | 59.160 | 50.577 | 1.00 | 18.24 | O |
| ATOM | 595 | N | GLN | X | 84 | 9.248 | 59.385 | 51.901 | 1.00 | 18.52 | N |
| ATOM | 596 | CA | GLN | X | 84 | 9.240 | 60.849 | 51.791 | 1.00 | 18.57 | C |
| ATOM | 597 | CB | GLN | X | 84 | 7.937 | 61.456 | 52.333 | 1.00 | 18.49 | C |
| ATOM | 598 | CG | GLN | X | 84 | 6.709 | 61.203 | 51.438 | 1.00 | 18.33 | C |
| ATOM | 599 | CD | GLN | X | 84 | 5.432 | 61.846 | 51.970 | 1.00 | 19.54 | C |
| ATOM | 600 | OE1 | GLN | X | 84 | 5.485 | 62.836 | 52.698 | 1.00 | 22.21 | O |
| ATOM | 601 | NE2 | GLN | X | 84 | 4.277 | 61.289 | 51.603 | 1.00 | 19.68 | N |
| ATOM | 602 | C | GLN | X | 84 | 10.487 | 61.486 | 52.413 | 1.00 | 18.38 | C |
| ATOM | 603 | O | GLN | X | 84 | 11.149 | 62.299 | 51.774 | 1.00 | 18.47 | O |
| ATOM | 604 | N | ARG | X | 85 | 10.827 | 61.097 | 53.639 | 1.00 | 18.38 | N |
| ATOM | 605 | CA | ARG | X | 85 | 12.042 | 61.608 | 54.287 | 1.00 | 18.16 | C |
| ATOM | 606 | CB | ARG | X | 85 | 12.153 | 61.069 | 55.714 | 1.00 | 18.58 | C |
| ATOM | 607 | CG | ARG | X | 85 | 13.389 | 61.544 | 56.468 | 1.00 | 21.55 | C |
| ATOM | 608 | CD | ARG | X | 85 | 13.255 | 61.267 | 57.955 | 1.00 | 26.37 | C |
| ATOM | 609 | NE | ARG | X | 85 | 14.539 | 61.396 | 58.636 | 1.00 | 30.42 | N |
| ATOM | 610 | CZ | ARG | X | 85 | 15.000 | 62.517 | 59.181 | 1.00 | 33.44 | C |
| ATOM | 611 | NH1 | ARG | X | 85 | 14.275 | 63.637 | 59.144 | 1.00 | 34.31 | N |
| ATOM | 612 | NH2 | ARG | X | 85 | 16.194 | 62.514 | 59.771 | 1.00 | 34.23 | N |
| ATOM | 613 | C | ARG | X | 85 | 13.289 | 61.250 | 53.474 | 1.00 | 17.61 | C |
| ATOM | 614 | O | ARG | X | 85 | 14.173 | 62.093 | 53.271 | 1.00 | 17.47 | O |
| ATOM | 615 | N | ALA | X | 86 | 13.336 | 60.001 | 53.006 | 1.00 | 16.99 | N |
| ATOM | 616 | CA | ALA | X | 86 | 14.429 | 59.496 | 52.176 | 1.00 | 16.60 | C |
| ATOM | 617 | CB | ALA | X | 86 | 14.199 | 58.028 | 51.844 | 1.00 | 16.58 | C |
| ATOM | 618 | C | ALA | X | 86 | 14.646 | 60.312 | 50.896 | 1.00 | 16.51 | C |
| ATOM | 619 | O | ALA | X | 86 | 15.781 | 60.671 | 50.588 | 1.00 | 16.15 | O |
| ATOM | 620 | N | VAL | X | 87 | 13.577 | 60.603 | 50.147 | 1.00 | 16.60 | N |
| ATOM | 621 | CA | VAL | X | 87 | 13.745 | 61.381 | 48.899 | 1.00 | 16.58 | C |
| ATOM | 622 | CB | VAL | X | 87 | 12.530 | 61.292 | 47.907 | 1.00 | 16.59 | C |
| ATOM | 623 | CG1 | VAL | X | 87 | 12.280 | 59.849 | 47.481 | 1.00 | 16.75 | C |
| ATOM | 624 | CG2 | VAL | X | 87 | 11.262 | 61.918 | 48.475 | 1.00 | 17.46 | C |
| ATOM | 625 | C | VAL | X | 87 | 14.157 | 62.833 | 49.178 | 1.00 | 16.27 | C |
| ATOM | 626 | O | VAL | X | 87 | 14.949 | 63.404 | 48.442 | 1.00 | 15.37 | O |
| ATOM | 627 | N | LEU | X | 88 | 13.633 | 63.401 | 50.264 | 1.00 | 16.52 | N |
| ATOM | 628 | CA | LEU | X | 88 | 14.032 | 64.735 | 50.720 | 1.00 | 16.66 | C |
| ATOM | 629 | CB | LEU | X | 88 | 13.129 | 65.222 | 51.870 | 1.00 | 16.75 | C |

APPENDIX 1-continued

X-RAY DATA COORDINATES FOR LRP-220 (SEQ ID NO: 5)

| ATOM | 630 | CG | LEU | X | 88 | 11.665 | 65.514 | 51.490 | 1.00 | 17.60 | C |
|---|---|---|---|---|---|---|---|---|---|---|---|
| ATOM | 631 | CD1 | LEU | X | 88 | 10.788 | 65.714 | 52.728 | 1.00 | 18.52 | C |
| ATOM | 632 | CD2 | LEU | X | 88 | 11.546 | 66.726 | 50.558 | 1.00 | 17.78 | C |
| ATOM | 633 | C | LEU | X | 88 | 15.511 | 64.790 | 51.099 | 1.00 | 16.61 | C |
| ATOM | 634 | O | LEU | X | 88 | 16.208 | 65.740 | 50.731 | 1.00 | 16.55 | O |
| ATOM | 635 | N | LYS | X | 89 | 15.990 | 63.761 | 51.802 | 1.00 | 16.68 | N |
| ATOM | 636 | CA | LYS | X | 89 | 17.409 | 63.653 | 52.162 | 1.00 | 17.00 | C |
| ATOM | 637 | CB | LYS | X | 89 | 17.630 | 62.549 | 53.213 | 1.00 | 17.52 | C |
| ATOM | 638 | CG | LYS | X | 89 | 17.007 | 62.819 | 54.594 | 1.00 | 19.55 | C |
| ATOM | 639 | CD | LYS | X | 89 | 17.681 | 63.987 | 55.327 | 1.00 | 24.32 | C |
| ATOM | 640 | CE | LYS | X | 89 | 18.978 | 63.552 | 56.009 | 1.00 | 27.24 | C |
| ATOM | 641 | NZ | LYS | X | 89 | 19.928 | 64.695 | 56.235 | 1.00 | 29.88 | N |
| ATOM | 642 | C | LYS | X | 89 | 18.293 | 63.398 | 50.929 | 1.00 | 16.68 | C |
| ATOM | 643 | O | LYS | X | 89 | 19.349 | 64.012 | 50.782 | 1.00 | 16.41 | O |
| ATOM | 644 | N | PHE | X | 90 | 17.853 | 62.501 | 50.044 | 1.00 | 16.21 | N |
| ATOM | 645 | CA | PHE | X | 90 | 18.581 | 62.222 | 48.796 | 1.00 | 15.79 | C |
| ATOM | 646 | CB | PHE | X | 90 | 17.848 | 61.167 | 47.950 | 1.00 | 14.97 | C |
| ATOM | 647 | CG | PHE | X | 90 | 18.538 | 60.845 | 46.644 | 1.00 | 14.54 | C |
| ATOM | 648 | CD1 | PHE | X | 90 | 18.347 | 61.648 | 45.518 | 1.00 | 13.59 | C |
| ATOM | 649 | CE1 | PHE | X | 90 | 18.988 | 61.358 | 44.308 | 1.00 | 13.40 | C |
| ATOM | 650 | CZ | PHE | X | 90 | 19.825 | 60.253 | 44.211 | 1.00 | 13.33 | C |
| ATOM | 651 | CE2 | PHE | X | 90 | 20.027 | 59.442 | 45.326 | 1.00 | 13.79 | C |
| ATOM | 652 | CD2 | PHE | X | 90 | 19.377 | 59.735 | 46.537 | 1.00 | 13.59 | C |
| ATOM | 653 | C | PHE | X | 90 | 18.750 | 63.513 | 47.997 | 1.00 | 15.78 | C |
| ATOM | 654 | O | PHE | X | 90 | 19.836 | 63.799 | 47.489 | 1.00 | 15.87 | O |
| ATOM | 655 | N | ALA | X | 91 | 17.671 | 64.284 | 47.893 | 1.00 | 15.93 | N |
| ATOM | 656 | CA | ALA | X | 91 | 17.677 | 65.534 | 47.133 | 1.00 | 16.60 | C |
| ATOM | 657 | CB | ALA | X | 91 | 16.265 | 66.091 | 47.005 | 1.00 | 16.62 | C |
| ATOM | 658 | C | ALA | X | 91 | 18.623 | 66.575 | 47.729 | 1.00 | 16.94 | C |
| ATOM | 659 | O | ALA | X | 91 | 19.407 | 67.184 | 47.001 | 1.00 | 17.28 | O |
| ATOM | 660 | N | ALA | X | 92 | 18.564 | 66.759 | 49.048 | 1.00 | 17.44 | N |
| ATOM | 661 | CA | ALA | X | 92 | 19.494 | 67.657 | 49.754 | 1.00 | 17.93 | C |
| ATOM | 662 | CB | ALA | X | 92 | 19.179 | 67.698 | 51.252 | 1.00 | 18.27 | C |
| ATOM | 663 | C | ALA | X | 92 | 20.946 | 67.254 | 49.529 | 1.00 | 18.02 | C |
| ATOM | 664 | O | ALA | X | 92 | 21.815 | 68.112 | 49.327 | 1.00 | 18.62 | O |
| ATOM | 665 | N | ALA | X | 93 | 21.200 | 65.947 | 49.534 | 1.00 | 17.75 | N |
| ATOM | 666 | CA | ALA | X | 93 | 22.553 | 65.420 | 49.377 | 1.00 | 17.34 | C |
| ATOM | 667 | CB | ALA | X | 93 | 22.613 | 63.982 | 49.878 | 1.00 | 17.36 | C |
| ATOM | 668 | C | ALA | X | 93 | 23.115 | 65.516 | 47.957 | 1.00 | 17.08 | C |
| ATOM | 669 | O | ALA | X | 93 | 24.318 | 65.681 | 47.773 | 1.00 | 17.15 | O |
| ATOM | 670 | N | THR | X | 94 | 22.249 | 65.406 | 46.954 | 1.00 | 17.27 | N |
| ATOM | 671 | CA | THR | X | 94 | 22.704 | 65.254 | 45.565 | 1.00 | 16.60 | C |
| ATOM | 672 | CB | THR | X | 94 | 22.144 | 63.967 | 44.917 | 1.00 | 16.86 | C |
| ATOM | 673 | OG1 | THR | X | 94 | 20.719 | 64.076 | 44.788 | 1.00 | 14.77 | O |
| ATOM | 674 | CG2 | THR | X | 94 | 22.513 | 62.729 | 45.739 | 1.00 | 16.99 | C |
| ATOM | 675 | C | THR | X | 94 | 22.361 | 66.424 | 44.643 | 1.00 | 16.72 | C |
| ATOM | 676 | O | THR | X | 94 | 22.928 | 66.536 | 43.556 | 1.00 | 16.53 | O |
| ATOM | 677 | N | GLY | X | 95 | 21.428 | 67.272 | 45.070 | 1.00 | 16.73 | N |
| ATOM | 678 | CA | GLY | X | 95 | 20.979 | 68.408 | 44.262 | 1.00 | 16.94 | C |
| ATOM | 679 | C | GLY | X | 95 | 19.783 | 68.106 | 43.369 | 1.00 | 17.04 | C |
| ATOM | 680 | O | GLY | X | 95 | 19.370 | 68.953 | 42.570 | 1.00 | 16.56 | O |
| ATOM | 681 | N | ALA | X | 96 | 19.230 | 66.898 | 43.505 | 1.00 | 16.94 | N |
| ATOM | 682 | CA | ALA | X | 96 | 18.031 | 66.484 | 42.766 | 1.00 | 16.84 | C |
| ATOM | 683 | CB | ALA | X | 96 | 17.851 | 64.970 | 42.864 | 1.00 | 16.42 | C |
| ATOM | 684 | C | ALA | X | 96 | 16.775 | 67.207 | 43.278 | 1.00 | 16.99 | C |
| ATOM | 685 | O | ALA | X | 96 | 16.772 | 67.750 | 44.382 | 1.00 | 16.89 | O |
| ATOM | 686 | N | THR | X | 97 | 15.712 | 67.203 | 42.476 | 1.00 | 16.97 | N |
| ATOM | 687 | CA | THR | X | 97 | 14.460 | 67.872 | 42.839 | 1.00 | 17.29 | C |
| ATOM | 688 | CB | THR | X | 97 | 13.852 | 68.646 | 41.629 | 1.00 | 17.32 | C |
| ATOM | 689 | OG1 | THR | X | 97 | 14.832 | 69.545 | 41.097 | 1.00 | 16.92 | O |
| ATOM | 690 | CG2 | THR | X | 97 | 12.619 | 69.448 | 42.043 | 1.00 | 17.35 | C |
| ATOM | 691 | C | THR | X | 97 | 13.457 | 66.857 | 43.380 | 1.00 | 17.63 | C |
| ATOM | 692 | O | THR | X | 97 | 13.065 | 65.942 | 42.657 | 1.00 | 17.32 | O |
| ATOM | 693 | N | PRO | X | 98 | 13.041 | 67.010 | 44.657 | 1.00 | 17.99 | N |
| ATOM | 694 | CA | PRO | X | 98 | 12.136 | 66.017 | 45.229 | 1.00 | 18.76 | C |
| ATOM | 695 | CB | PRO | X | 98 | 12.488 | 66.052 | 46.719 | 1.00 | 18.80 | C |
| ATOM | 696 | CG | PRO | X | 98 | 12.880 | 67.521 | 46.972 | 1.00 | 18.29 | C |
| ATOM | 697 | CD | PRO | X | 98 | 13.380 | 68.074 | 45.631 | 1.00 | 18.26 | C |
| ATOM | 698 | C | PRO | X | 98 | 10.658 | 66.350 | 45.042 | 1.00 | 19.44 | C |
| ATOM | 699 | O | PRO | X | 98 | 10.273 | 67.522 | 45.071 | 1.00 | 19.77 | O |
| ATOM | 700 | N | ILE | X | 99 | 9.843 | 65.317 | 44.846 | 1.00 | 19.98 | N |
| ATOM | 701 | CA | ILE | X | 99 | 8.400 | 65.440 | 45.017 | 1.00 | 20.65 | C |
| ATOM | 702 | CB | ILE | X | 99 | 7.605 | 65.276 | 43.696 | 1.00 | 20.55 | C |
| ATOM | 703 | CG1 | ILE | X | 99 | 8.132 | 66.222 | 42.608 | 1.00 | 20.58 | C |
| ATOM | 704 | CD1 | ILE | X | 99 | 7.378 | 66.115 | 41.267 | 1.00 | 21.08 | C |
| ATOM | 705 | CG2 | ILE | X | 99 | 6.112 | 65.513 | 43.949 | 1.00 | 20.67 | C |
| ATOM | 706 | C | ILE | X | 99 | 7.949 | 64.406 | 46.042 | 1.00 | 20.95 | C |
| ATOM | 707 | O | ILE | X | 99 | 7.700 | 63.239 | 45.710 | 1.00 | 21.31 | O |

APPENDIX 1-continued

X-RAY DATA COORDINATES FOR LRP-220 (SEQ ID NO: 5)

| ATOM | 708 | N | ALA | X | 100 | 7.869 | 64.844 | 47.295 | 1.00 | 21.40 | N |
|---|---|---|---|---|---|---|---|---|---|---|---|
| ATOM | 709 | CA | ALA | X | 100 | 7.403 | 64.010 | 48.397 | 1.00 | 21.67 | C |
| ATOM | 710 | CB | ALA | X | 100 | 8.216 | 64.307 | 49.662 | 1.00 | 21.55 | C |
| ATOM | 711 | C | ALA | X | 100 | 5.925 | 64.281 | 48.640 | 1.00 | 21.93 | C |
| ATOM | 712 | O | ALA | X | 100 | 5.504 | 65.439 | 48.737 | 1.00 | 22.20 | O |
| ATOM | 713 | N | GLY | X | 101 | 5.140 | 63.216 | 48.738 | 1.00 | 22.03 | N |
| ATOM | 714 | CA | GLY | X | 101 | 3.711 | 63.346 | 48.965 | 1.00 | 22.51 | C |
| ATOM | 715 | C | GLY | X | 101 | 2.942 | 63.342 | 47.658 | 1.00 | 22.75 | C |
| ATOM | 716 | O | GLY | X | 101 | 3.298 | 62.620 | 46.724 | 1.00 | 22.69 | O |
| ATOM | 717 | N | ARG | X | 102 | 1.894 | 64.160 | 47.588 | 1.00 | 22.86 | N |
| ATOM | 718 | CA | ARG | X | 102 | 0.992 | 64.146 | 46.437 | 1.00 | 23.05 | C |
| ATOM | 719 | CB | ARG | X | 102 | −0.275 | 64.963 | 46.702 | 1.00 | 23.67 | C |
| ATOM | 720 | CG | ARG | X | 102 | −1.432 | 64.587 | 45.760 | 1.00 | 27.17 | C |
| ATOM | 721 | CD | ARG | X | 102 | −2.557 | 65.621 | 45.778 | 1.00 | 33.00 | C |
| ATOM | 722 | NE | ARG | X | 102 | −3.551 | 65.360 | 44.731 | 1.00 | 36.11 | N |
| ATOM | 723 | CZ | ARG | X | 102 | −3.790 | 66.168 | 43.700 | 1.00 | 37.86 | C |
| ATOM | 724 | NH1 | ARG | X | 102 | −3.115 | 67.310 | 43.565 | 1.00 | 38.62 | N |
| ATOM | 725 | NH2 | ARG | X | 102 | −4.714 | 65.835 | 42.804 | 1.00 | 38.84 | N |
| ATOM | 726 | C | ARG | X | 102 | 1.663 | 64.616 | 45.156 | 1.00 | 22.14 | C |
| ATOM | 727 | O | ARG | X | 102 | 2.343 | 65.634 | 45.128 | 1.00 | 22.60 | O |
| ATOM | 728 | N | PHE | X | 103 | 1.474 | 63.843 | 44.100 | 1.00 | 21.51 | N |
| ATOM | 729 | CA | PHE | X | 103 | 1.874 | 64.238 | 42.764 | 1.00 | 20.69 | C |
| ATOM | 730 | CB | PHE | X | 103 | 2.571 | 63.064 | 42.064 | 1.00 | 20.07 | C |
| ATOM | 731 | CG | PHE | X | 103 | 3.002 | 63.348 | 40.647 | 1.00 | 19.32 | C |
| ATOM | 732 | CD1 | PHE | X | 103 | 2.163 | 63.055 | 39.575 | 1.00 | 17.50 | C |
| ATOM | 733 | CE1 | PHE | X | 103 | 2.565 | 63.302 | 38.269 | 1.00 | 17.80 | C |
| ATOM | 734 | CZ | PHE | X | 103 | 3.819 | 63.844 | 38.021 | 1.00 | 18.07 | C |
| ATOM | 735 | CE2 | PHE | X | 103 | 4.662 | 64.143 | 39.085 | 1.00 | 17.29 | C |
| ATOM | 736 | CD2 | PHE | X | 103 | 4.256 | 63.889 | 40.384 | 1.00 | 17.28 | C |
| ATOM | 737 | C | PHE | X | 103 | 0.579 | 64.626 | 42.058 | 1.00 | 20.64 | C |
| ATOM | 738 | O | PHE | X | 103 | −0.308 | 63.794 | 41.874 | 1.00 | 20.75 | O |
| ATOM | 739 | N | THR | X | 104 | 0.464 | 65.901 | 41.700 | 1.00 | 20.41 | N |
| ATOM | 740 | CA | THR | X | 104 | −0.708 | 66.402 | 40.982 | 1.00 | 20.68 | C |
| ATOM | 741 | CB | THR | X | 104 | −0.745 | 67.951 | 40.979 | 1.00 | 20.76 | C |
| ATOM | 742 | OG1 | THR | X | 104 | −0.695 | 68.425 | 42.328 | 1.00 | 21.58 | O |
| ATOM | 743 | CG2 | THR | X | 104 | −2.018 | 68.469 | 40.306 | 1.00 | 21.15 | C |
| ATOM | 744 | C | THR | X | 104 | −0.710 | 65.882 | 39.547 | 1.00 | 20.16 | C |
| ATOM | 745 | O | THR | X | 104 | 0.244 | 66.108 | 38.813 | 1.00 | 20.15 | O |
| ATOM | 746 | N | PRO | X | 105 | −1.781 | 65.175 | 39.147 | 1.00 | 20.15 | N |
| ATOM | 747 | CA | PRO | X | 105 | −1.871 | 64.682 | 37.768 | 1.00 | 20.04 | C |
| ATOM | 748 | CB | PRO | X | 105 | −3.275 | 64.069 | 37.707 | 1.00 | 19.98 | C |
| ATOM | 749 | CG | PRO | X | 105 | −3.564 | 63.675 | 39.143 | 1.00 | 20.49 | C |
| ATOM | 750 | CD | PRO | X | 105 | −2.953 | 64.781 | 39.952 | 1.00 | 20.10 | C |
| ATOM | 751 | C | PRO | X | 105 | −1.719 | 65.825 | 36.758 | 1.00 | 20.02 | C |
| ATOM | 752 | O | PRO | X | 105 | −2.322 | 66.879 | 36.934 | 1.00 | 19.57 | O |
| ATOM | 753 | N | GLY | X | 106 | −0.896 | 65.616 | 35.732 | 1.00 | 20.06 | N |
| ATOM | 754 | CA | GLY | X | 106 | −0.598 | 66.658 | 34.752 | 1.00 | 20.30 | C |
| ATOM | 755 | C | GLY | X | 106 | 0.703 | 67.406 | 35.013 | 1.00 | 20.84 | C |
| ATOM | 756 | O | GLY | X | 106 | 1.119 | 68.225 | 34.198 | 1.00 | 20.54 | O |
| ATOM | 757 | N | THR | X | 107 | 1.349 | 67.140 | 36.145 | 1.00 | 21.12 | N |
| ATOM | 758 | CA | THR | X | 107 | 2.638 | 67.778 | 36.462 | 1.00 | 21.98 | C |
| ATOM | 759 | CB | THR | X | 107 | 3.228 | 67.252 | 37.797 | 1.00 | 21.60 | C |
| ATOM | 760 | OG1 | THR | X | 107 | 2.318 | 67.541 | 38.861 | 1.00 | 21.06 | O |
| ATOM | 761 | CG2 | THR | X | 107 | 4.575 | 67.899 | 38.116 | 1.00 | 22.08 | C |
| ATOM | 762 | C | THR | X | 107 | 3.637 | 67.606 | 35.313 | 1.00 | 22.66 | C |
| ATOM | 763 | O | THR | X | 107 | 4.340 | 68.558 | 34.951 | 1.00 | 22.79 | O |
| ATOM | 764 | N | PHE | X | 108 | 3.678 | 66.405 | 34.735 | 1.00 | 23.33 | N |
| ATOM | 765 | CA | PHE | X | 108 | 4.544 | 66.128 | 33.597 | 1.00 | 24.37 | C |
| ATOM | 766 | CB | PHE | X | 108 | 5.146 | 64.712 | 33.669 | 1.00 | 23.71 | C |
| ATOM | 767 | CG | PHE | X | 108 | 6.058 | 64.479 | 34.856 | 1.00 | 22.65 | C |
| ATOM | 768 | CD1 | PHE | X | 108 | 6.694 | 65.540 | 35.501 | 1.00 | 20.74 | C |
| ATOM | 769 | CE1 | PHE | X | 108 | 7.542 | 65.317 | 36.583 | 1.00 | 21.37 | C |
| ATOM | 770 | CZ | PHE | X | 108 | 7.771 | 64.016 | 37.029 | 1.00 | 22.32 | C |
| ATOM | 771 | CE2 | PHE | X | 108 | 7.151 | 62.946 | 36.384 | 1.00 | 21.63 | C |
| ATOM | 772 | CD2 | PHE | X | 108 | 6.305 | 63.184 | 35.302 | 1.00 | 21.95 | C |
| ATOM | 773 | C | PHE | X | 108 | 3.849 | 66.360 | 32.247 | 1.00 | 25.79 | C |
| ATOM | 774 | O | PHE | X | 108 | 4.422 | 67.003 | 31.374 | 1.00 | 26.35 | O |
| ATOM | 775 | N | THR | X | 109 | 2.628 | 65.849 | 32.077 | 1.00 | 27.27 | N |
| ATOM | 776 | CA | THR | X | 109 | 1.922 | 65.940 | 30.780 | 1.00 | 28.86 | C |
| ATOM | 777 | CB | THR | X | 109 | 0.732 | 64.950 | 30.677 | 1.00 | 28.57 | C |
| ATOM | 778 | OG1 | THR | X | 109 | −0.196 | 65.190 | 31.740 | 1.00 | 28.28 | O |
| ATOM | 779 | CG2 | THR | X | 109 | 1.209 | 63.498 | 30.739 | 1.00 | 28.18 | C |
| ATOM | 780 | C | THR | X | 109 | 1.433 | 67.356 | 30.412 | 1.00 | 30.37 | C |
| ATOM | 781 | O | THR | X | 109 | 1.350 | 67.698 | 29.232 | 1.00 | 30.35 | O |
| ATOM | 782 | N | ASN | X | 110 | 1.098 | 68.162 | 31.417 | 1.00 | 32.08 | N |
| ATOM | 783 | CA | ASN | X | 110 | 0.687 | 69.553 | 31.201 | 1.00 | 34.07 | C |
| ATOM | 784 | CB | ASN | X | 110 | −0.083 | 70.068 | 32.419 | 1.00 | 34.27 | C |
| ATOM | 785 | CG | ASN | X | 110 | −1.571 | 69.980 | 32.252 | 1.00 | 35.53 | C |

APPENDIX 1-continued

X-RAY DATA COORDINATES FOR LRP-220 (SEQ ID NO: 5)

| ATOM | 786 | OD1 | ASN | X | 110 | −2.180 | 70.876 | 31.681 | 1.00 | 38.58 | O |
|---|---|---|---|---|---|---|---|---|---|---|---|
| ATOM | 787 | ND2 | ASN | X | 110 | −2.178 | 68.926 | 32.782 | 1.00 | 36.18 | N |
| ATOM | 788 | C | ASN | X | 110 | 1.899 | 70.447 | 30.958 | 1.00 | 35.02 | C |
| ATOM | 789 | O | ASN | X | 110 | 2.430 | 71.048 | 31.888 | 1.00 | 35.57 | O |
| ATOM | 790 | N | GLN | X | 111 | 2.352 | 70.534 | 29.716 | 1.00 | 36.38 | N |
| ATOM | 791 | CA | GLN | X | 111 | 3.563 | 71.296 | 29.451 | 1.00 | 37.55 | C |
| ATOM | 792 | CB | GLN | X | 111 | 4.713 | 70.375 | 29.047 | 1.00 | 37.86 | C |
| ATOM | 793 | CG | GLN | X | 111 | 6.095 | 71.025 | 29.121 | 1.00 | 39.62 | C |
| ATOM | 794 | CD | GLN | X | 111 | 6.402 | 71.623 | 30.483 | 1.00 | 41.90 | C |
| ATOM | 795 | OE1 | GLN | X | 111 | 6.579 | 70.896 | 31.470 | 1.00 | 42.33 | O |
| ATOM | 796 | NE2 | GLN | X | 111 | 6.470 | 72.961 | 30.544 | 1.00 | 41.48 | N |
| ATOM | 797 | C | GLN | X | 111 | 3.369 | 72.420 | 28.445 | 1.00 | 37.98 | C |
| ATOM | 798 | O | GLN | X | 111 | 2.883 | 72.203 | 27.335 | 1.00 | 38.21 | O |
| ATOM | 799 | N | ILE | X | 112 | 3.776 | 73.619 | 28.860 | 1.00 | 38.65 | N |
| ATOM | 800 | CA | ILE | X | 112 | 3.606 | 74.851 | 28.084 | 1.00 | 39.07 | C |
| ATOM | 801 | CB | ILE | X | 112 | 3.508 | 76.088 | 29.018 | 1.00 | 39.13 | C |
| ATOM | 802 | CG1 | ILE | X | 112 | 4.823 | 76.288 | 29.793 | 1.00 | 39.83 | C |
| ATOM | 803 | CD1 | ILE | X | 112 | 4.848 | 77.481 | 30.741 | 1.00 | 39.68 | C |
| ATOM | 804 | CG2 | ILE | X | 112 | 2.305 | 75.943 | 29.964 | 1.00 | 39.97 | C |
| ATOM | 805 | C | ILE | X | 112 | 4.726 | 75.066 | 27.062 | 1.00 | 38.69 | C |
| ATOM | 806 | O | ILE | X | 112 | 4.609 | 75.922 | 26.169 | 1.00 | 39.27 | O |
| ATOM | 807 | N | GLN | X | 113 | 5.802 | 74.289 | 27.195 | 1.00 | 37.82 | N |
| ATOM | 808 | CA | GLN | X | 113 | 6.989 | 74.443 | 26.361 | 1.00 | 36.64 | C |
| ATOM | 809 | CB | GLN | X | 113 | 8.093 | 75.184 | 27.123 | 1.00 | 37.01 | C |
| ATOM | 810 | CG | GLN | X | 113 | 8.202 | 76.660 | 26.774 | 1.00 | 38.82 | C |
| ATOM | 811 | CD | GLN | X | 113 | 8.131 | 77.561 | 27.987 | 1.00 | 41.43 | C |
| ATOM | 812 | OE1 | GLN | X | 113 | 8.776 | 77.310 | 29.010 | 1.00 | 42.62 | O |
| ATOM | 813 | NE2 | GLN | X | 113 | 7.333 | 78.626 | 27.881 | 1.00 | 42.06 | N |
| ATOM | 814 | C | GLN | X | 113 | 7.508 | 73.109 | 25.849 | 1.00 | 35.43 | C |
| ATOM | 815 | O | GLN | X | 113 | 7.676 | 72.157 | 26.607 | 1.00 | 35.25 | O |
| ATOM | 816 | N | ALA | X | 114 | 7.753 | 73.059 | 24.546 | 1.00 | 33.91 | N |
| ATOM | 817 | CA | ALA | X | 114 | 8.380 | 71.913 | 23.902 | 1.00 | 32.18 | C |
| ATOM | 818 | CB | ALA | X | 114 | 8.214 | 72.037 | 22.402 | 1.00 | 32.43 | C |
| ATOM | 819 | C | ALA | X | 114 | 9.867 | 71.827 | 24.251 | 1.00 | 30.68 | C |
| ATOM | 820 | O | ALA | X | 114 | 10.418 | 70.737 | 24.419 | 1.00 | 30.39 | O |
| ATOM | 821 | N | ALA | X | 115 | 10.500 | 72.992 | 24.359 | 1.00 | 29.00 | N |
| ATOM | 822 | CA | ALA | X | 115 | 11.949 | 73.098 | 24.490 | 1.00 | 27.55 | C |
| ATOM | 823 | CB | ALA | X | 115 | 12.434 | 74.411 | 23.870 | 1.00 | 27.22 | C |
| ATOM | 824 | C | ALA | X | 115 | 12.417 | 72.988 | 25.940 | 1.00 | 26.49 | C |
| ATOM | 825 | O | ALA | X | 115 | 11.735 | 73.462 | 26.849 | 1.00 | 26.04 | O |
| ATOM | 826 | N | PHE | X | 116 | 13.583 | 72.362 | 26.130 | 1.00 | 25.25 | N |
| ATOM | 827 | CA | PHE | X | 116 | 14.278 | 72.280 | 27.432 | 1.00 | 24.37 | C |
| ATOM | 828 | CB | PHE | X | 116 | 14.855 | 73.642 | 27.838 | 1.00 | 24.42 | C |
| ATOM | 829 | CG | PHE | X | 116 | 15.704 | 74.256 | 26.770 | 1.00 | 24.56 | C |
| ATOM | 830 | CD1 | PHE | X | 116 | 17.005 | 73.825 | 26.573 | 1.00 | 24.63 | C |
| ATOM | 831 | CE1 | PHE | X | 116 | 17.786 | 74.373 | 25.562 | 1.00 | 25.42 | C |
| ATOM | 832 | CZ | PHE | X | 116 | 17.258 | 75.350 | 24.734 | 1.00 | 24.56 | C |
| ATOM | 833 | CE2 | PHE | X | 116 | 15.953 | 75.774 | 24.911 | 1.00 | 24.23 | C |
| ATOM | 834 | CD2 | PHE | X | 116 | 15.183 | 75.228 | 25.925 | 1.00 | 24.58 | C |
| ATOM | 835 | C | PHE | X | 116 | 13.406 | 71.671 | 28.514 | 1.00 | 23.76 | C |
| ATOM | 836 | O | PHE | X | 116 | 13.328 | 72.152 | 29.650 | 1.00 | 23.31 | O |
| ATOM | 837 | N | ARG | X | 117 | 12.764 | 70.583 | 28.116 | 1.00 | 22.95 | N |
| ATOM | 838 | CA | ARG | X | 117 | 11.836 | 69.836 | 28.932 | 1.00 | 22.58 | C |
| ATOM | 839 | CB | ARG | X | 117 | 11.229 | 68.739 | 28.063 | 1.00 | 23.11 | C |
| ATOM | 840 | CG | ARG | X | 117 | 10.381 | 67.786 | 28.801 | 1.00 | 26.40 | C |
| ATOM | 841 | CD | ARG | X | 117 | 9.223 | 67.388 | 27.956 | 1.00 | 31.69 | C |
| ATOM | 842 | NE | ARG | X | 117 | 8.079 | 67.243 | 28.829 | 1.00 | 35.88 | N |
| ATOM | 843 | CZ | ARG | X | 117 | 6.862 | 67.673 | 28.540 | 1.00 | 38.16 | C |
| ATOM | 844 | NH1 | ARG | X | 117 | 6.624 | 68.282 | 27.380 | 1.00 | 38.49 | N |
| ATOM | 845 | NH2 | ARG | X | 117 | 5.891 | 67.494 | 29.422 | 1.00 | 39.18 | N |
| ATOM | 846 | C | ARG | X | 117 | 12.480 | 69.246 | 30.193 | 1.00 | 21.31 | C |
| ATOM | 847 | O | ARG | X | 117 | 13.551 | 68.636 | 30.140 | 1.00 | 21.06 | O |
| ATOM | 848 | N | GLU | X | 118 | 11.804 | 69.437 | 31.321 | 1.00 | 20.15 | N |
| ATOM | 849 | CA | GLU | X | 118 | 12.299 | 69.005 | 32.618 | 1.00 | 19.48 | C |
| ATOM | 850 | CB | GLU | X | 118 | 12.835 | 70.213 | 33.407 | 1.00 | 19.54 | C |
| ATOM | 851 | CG | GLU | X | 118 | 14.101 | 70.874 | 32.785 | 1.00 | 20.03 | C |
| ATOM | 852 | CD | GLU | X | 118 | 14.407 | 72.255 | 33.371 | 1.00 | 20.32 | C |
| ATOM | 853 | OE1 | GLU | X | 118 | 13.702 | 73.220 | 33.011 | 1.00 | 20.60 | O |
| ATOM | 854 | OE2 | GLU | X | 118 | 15.354 | 72.382 | 34.190 | 1.00 | 21.21 | O |
| ATOM | 855 | C | GLU | X | 118 | 11.163 | 68.317 | 33.379 | 1.00 | 18.61 | C |
| ATOM | 856 | O | GLU | X | 118 | 9.990 | 68.672 | 33.182 | 1.00 | 18.67 | O |
| ATOM | 857 | N | PRO | X | 119 | 11.489 | 67.318 | 34.236 | 1.00 | 17.43 | N |
| ATOM | 858 | CA | PRO | X | 119 | 12.808 | 66.702 | 34.476 | 1.00 | 16.34 | C |
| ATOM | 859 | CB | PRO | X | 119 | 12.548 | 65.736 | 35.641 | 1.00 | 16.16 | C |
| ATOM | 860 | CG | PRO | X | 119 | 11.102 | 65.507 | 35.639 | 1.00 | 16.78 | C |
| ATOM | 861 | CD | PRO | X | 119 | 10.454 | 66.742 | 35.108 | 1.00 | 16.78 | C |
| ATOM | 862 | C | PRO | X | 119 | 13.356 | 65.922 | 33.280 | 1.00 | 15.31 | C |
| ATOM | 863 | O | PRO | X | 119 | 12.632 | 65.646 | 32.325 | 1.00 | 14.60 | O |

APPENDIX 1-continued

X-RAY DATA COORDINATES FOR LRP-220 (SEQ ID NO: 5)

| ATOM | 864 | N | ARG | X | 120 | 14.641 | 65.592 | 33.349 | 1.00 | 14.55 | N |
|---|---|---|---|---|---|---|---|---|---|---|---|
| ATOM | 865 | CA | ARG | X | 120 | 15.301 | 64.782 | 32.329 | 1.00 | 14.10 | C |
| ATOM | 866 | CB | ARG | X | 120 | 16.705 | 65.330 | 32.048 | 1.00 | 14.08 | C |
| ATOM | 867 | CG | ARG | X | 120 | 16.724 | 66.721 | 31.427 | 1.00 | 13.92 | C |
| ATOM | 868 | CD | ARG | X | 120 | 18.152 | 67.134 | 31.105 | 1.00 | 14.02 | C |
| ATOM | 869 | NE | ARG | X | 120 | 18.705 | 66.304 | 30.043 | 1.00 | 13.76 | N |
| ATOM | 870 | CZ | ARG | X | 120 | 19.992 | 66.008 | 29.906 | 1.00 | 15.31 | C |
| ATOM | 871 | NH1 | ARG | X | 120 | 20.883 | 66.464 | 30.777 | 1.00 | 14.55 | N |
| ATOM | 872 | NH2 | ARG | X | 120 | 20.387 | 65.236 | 28.895 | 1.00 | 17.13 | N |
| ATOM | 873 | C | ARG | X | 120 | 15.391 | 63.327 | 32.768 | 1.00 | 13.55 | C |
| ATOM | 874 | O | ARG | X | 120 | 15.600 | 62.440 | 31.953 | 1.00 | 13.14 | O |
| ATOM | 875 | N | LEU | X | 121 | 15.227 | 63.089 | 34.064 | 1.00 | 13.36 | N |
| ATOM | 876 | CA | LEU | X | 121 | 15.255 | 61.737 | 34.613 | 1.00 | 13.20 | C |
| ATOM | 877 | CB | LEU | X | 121 | 16.690 | 61.319 | 34.958 | 1.00 | 13.15 | C |
| ATOM | 878 | CG | LEU | X | 121 | 16.957 | 59.917 | 35.532 | 1.00 | 13.48 | C |
| ATOM | 879 | CD1 | LEU | X | 121 | 16.618 | 58.803 | 34.528 | 1.00 | 12.75 | C |
| ATOM | 880 | CD2 | LEU | X | 121 | 18.404 | 59.808 | 35.967 | 1.00 | 13.17 | C |
| ATOM | 881 | C | LEU | X | 121 | 14.355 | 61.665 | 35.845 | 1.00 | 13.02 | C |
| ATOM | 882 | O | LEU | X | 121 | 14.327 | 62.584 | 36.672 | 1.00 | 13.22 | O |
| ATOM | 883 | N | LEU | X | 122 | 13.617 | 60.571 | 35.953 | 1.00 | 12.73 | N |
| ATOM | 884 | CA | LEU | X | 122 | 12.721 | 60.361 | 37.073 | 1.00 | 12.88 | C |
| ATOM | 885 | CB | LEU | X | 122 | 11.274 | 60.250 | 36.577 | 1.00 | 13.01 | C |
| ATOM | 886 | CG | LEU | X | 122 | 10.217 | 59.856 | 37.614 | 1.00 | 13.55 | C |
| ATOM | 887 | CD1 | LEU | X | 122 | 10.104 | 60.923 | 38.694 | 1.00 | 12.85 | C |
| ATOM | 888 | CD2 | LEU | X | 122 | 8.867 | 59.587 | 36.953 | 1.00 | 12.51 | C |
| ATOM | 889 | C | LEU | X | 122 | 13.117 | 59.117 | 37.871 | 1.00 | 13.13 | C |
| ATOM | 890 | O | LEU | X | 122 | 13.364 | 58.048 | 37.306 | 1.00 | 12.99 | O |
| ATOM | 891 | N | VAL | X | 123 | 13.206 | 59.266 | 39.187 | 1.00 | 13.02 | N |
| ATOM | 892 | CA | VAL | X | 123 | 13.380 | 58.101 | 40.043 | 1.00 | 13.06 | C |
| ATOM | 893 | CB | VAL | X | 123 | 14.895 | 57.858 | 40.471 | 1.00 | 13.01 | C |
| ATOM | 894 | CG1 | VAL | X | 123 | 15.740 | 59.116 | 40.419 | 1.00 | 13.47 | C |
| ATOM | 895 | CG2 | VAL | X | 123 | 15.045 | 57.072 | 41.765 | 1.00 | 13.75 | C |
| ATOM | 896 | C | VAL | X | 123 | 12.300 | 58.002 | 41.135 | 1.00 | 13.24 | C |
| ATOM | 897 | O | VAL | X | 123 | 12.051 | 58.960 | 41.875 | 1.00 | 13.28 | O |
| ATOM | 898 | N | VAL | X | 124 | 11.620 | 56.858 | 41.176 | 1.00 | 13.15 | N |
| ATOM | 899 | CA | VAL | X | 124 | 10.482 | 56.661 | 42.078 | 1.00 | 13.12 | C |
| ATOM | 900 | CB | VAL | X | 124 | 9.117 | 56.447 | 41.328 | 1.00 | 13.16 | C |
| ATOM | 901 | CG1 | VAL | X | 124 | 8.872 | 57.539 | 40.282 | 1.00 | 12.38 | C |
| ATOM | 902 | CG2 | VAL | X | 124 | 9.041 | 55.066 | 40.687 | 1.00 | 12.89 | C |
| ATOM | 903 | C | VAL | X | 124 | 10.709 | 55.527 | 43.079 | 1.00 | 13.18 | C |
| ATOM | 904 | O | VAL | X | 124 | 11.514 | 54.619 | 42.847 | 1.00 | 12.76 | O |
| ATOM | 905 | N | THR | X | 125 | 9.976 | 55.598 | 44.186 | 1.00 | 13.18 | N |
| ATOM | 906 | CA | THR | X | 125 | 10.116 | 54.654 | 45.286 | 1.00 | 13.79 | C |
| ATOM | 907 | CB | THR | X | 125 | 9.684 | 55.325 | 46.617 | 1.00 | 13.80 | C |
| ATOM | 908 | OG1 | THR | X | 125 | 10.532 | 56.455 | 46.864 | 1.00 | 14.25 | O |
| ATOM | 909 | CG2 | THR | X | 125 | 9.769 | 54.358 | 47.796 | 1.00 | 13.19 | C |
| ATOM | 910 | C | THR | X | 125 | 9.338 | 53.356 | 45.065 | 1.00 | 13.98 | C |
| ATOM | 911 | O | THR | X | 125 | 9.751 | 52.304 | 45.541 | 1.00 | 13.85 | O |
| ATOM | 912 | N | ASP | X | 126 | 8.225 | 53.427 | 44.336 | 1.00 | 14.60 | N |
| ATOM | 913 | CA | ASP | X | 126 | 7.270 | 52.319 | 44.286 | 1.00 | 15.58 | C |
| ATOM | 914 | CB | ASP | X | 126 | 6.406 | 52.356 | 45.565 | 1.00 | 15.59 | C |
| ATOM | 915 | CG | ASP | X | 126 | 5.375 | 51.218 | 45.657 | 1.00 | 16.75 | C |
| ATOM | 916 | OD1 | ASP | X | 126 | 5.034 | 50.575 | 44.644 | 1.00 | 17.08 | O |
| ATOM | 917 | OD2 | ASP | X | 126 | 4.887 | 50.981 | 46.782 | 1.00 | 18.47 | O |
| ATOM | 918 | C | ASP | X | 126 | 6.418 | 52.463 | 43.032 | 1.00 | 16.06 | C |
| ATOM | 919 | O | ASP | X | 126 | 5.566 | 53.342 | 42.976 | 1.00 | 16.09 | O |
| ATOM | 920 | N | PRO | X | 127 | 6.645 | 51.606 | 42.016 | 1.00 | 16.67 | N |
| ATOM | 921 | CA | PRO | X | 127 | 5.917 | 51.738 | 40.750 | 1.00 | 17.51 | C |
| ATOM | 922 | CB | PRO | X | 127 | 6.471 | 50.580 | 39.903 | 1.00 | 17.42 | C |
| ATOM | 923 | CG | PRO | X | 127 | 7.794 | 50.297 | 40.483 | 1.00 | 17.16 | C |
| ATOM | 924 | CD | PRO | X | 127 | 7.594 | 50.483 | 41.961 | 1.00 | 16.89 | C |
| ATOM | 925 | C | PRO | X | 127 | 4.401 | 51.612 | 40.883 | 1.00 | 18.08 | C |
| ATOM | 926 | O | PRO | X | 127 | 3.671 | 52.136 | 40.042 | 1.00 | 18.48 | O |
| ATOM | 927 | N | ARG | X | 128 | 3.951 | 50.928 | 41.935 | 1.00 | 18.42 | N |
| ATOM | 928 | CA | ARG | X | 128 | 2.533 | 50.747 | 42.236 | 1.00 | 19.55 | C |
| ATOM | 929 | CB | ARG | X | 128 | 2.374 | 49.541 | 43.187 | 1.00 | 20.14 | C |
| ATOM | 930 | CG | ARG | X | 128 | 0.951 | 49.042 | 43.542 | 1.00 | 24.68 | C |
| ATOM | 931 | CD | ARG | X | 128 | 0.144 | 48.414 | 42.369 | 1.00 | 31.10 | C |
| ATOM | 932 | NE | ARG | X | 128 | 0.541 | 47.092 | 41.821 | 1.00 | 33.70 | N |
| ATOM | 933 | CZ | ARG | X | 128 | 1.310 | 46.159 | 42.396 | 1.00 | 34.27 | C |
| ATOM | 934 | NH1 | ARG | X | 128 | 1.838 | 46.322 | 43.601 | 1.00 | 34.54 | N |
| ATOM | 935 | NH2 | ARG | X | 128 | 1.549 | 45.031 | 41.739 | 1.00 | 34.73 | N |
| ATOM | 936 | C | ARG | X | 128 | 1.960 | 52.055 | 42.812 | 1.00 | 18.79 | C |
| ATOM | 937 | O | ARG | X | 128 | 1.043 | 52.636 | 42.240 | 1.00 | 18.93 | O |
| ATOM | 938 | N | ALA | X | 129 | 2.526 | 52.538 | 43.914 | 1.00 | 18.15 | N |
| ATOM | 939 | CA | ALA | X | 129 | 2.052 | 53.771 | 44.539 | 1.00 | 17.79 | C |
| ATOM | 940 | CB | ALA | X | 129 | 2.625 | 53.915 | 45.933 | 1.00 | 17.72 | C |
| ATOM | 941 | C | ALA | X | 129 | 2.366 | 55.017 | 43.699 | 1.00 | 17.52 | C |

APPENDIX 1-continued

X-RAY DATA COORDINATES FOR LRP-220 (SEQ ID NO: 5)

| ATOM | 942 | O | ALA | X | 129 | 1.605 | 55.981 | 43.697 | 1.00 | 17.04 | O |
|---|---|---|---|---|---|---|---|---|---|---|---|
| ATOM | 943 | N | ASP | X | 130 | 3.491 | 54.983 | 42.991 | 1.00 | 17.23 | N |
| ATOM | 944 | CA | ASP | X | 130 | 3.935 | 56.117 | 42.188 | 1.00 | 17.23 | C |
| ATOM | 945 | CB | ASP | X | 130 | 5.428 | 56.372 | 42.433 | 1.00 | 17.10 | C |
| ATOM | 946 | CG | ASP | X | 130 | 5.725 | 56.714 | 43.882 | 1.00 | 17.70 | C |
| ATOM | 947 | OD1 | ASP | X | 130 | 4.993 | 57.561 | 44.441 | 1.00 | 18.36 | O |
| ATOM | 948 | OD2 | ASP | X | 130 | 6.677 | 56.145 | 44.466 | 1.00 | 16.55 | O |
| ATOM | 949 | C | ASP | X | 130 | 3.635 | 55.911 | 40.707 | 1.00 | 17.03 | C |
| ATOM | 950 | O | ASP | X | 130 | 4.374 | 56.375 | 39.846 | 1.00 | 16.69 | O |
| ATOM | 951 | N | HIS | X | 131 | 2.535 | 55.219 | 40.416 | 1.00 | 17.32 | N |
| ATOM | 952 | CA | HIS | X | 131 | 2.159 | 54.916 | 39.039 | 1.00 | 17.64 | C |
| ATOM | 953 | CB | HIS | X | 131 | 0.936 | 53.987 | 38.998 | 1.00 | 18.00 | C |
| ATOM | 954 | CG | HIS | X | 131 | −0.354 | 54.683 | 39.299 | 1.00 | 19.71 | C |
| ATOM | 955 | ND1 | HIS | X | 131 | −0.868 | 54.777 | 49.576 | 1.00 | 21.28 | N |
| ATOM | 956 | CE1 | HIS | X | 131 | −1.997 | 55.464 | 40.545 | 1.00 | 22.13 | C |
| ATOM | 957 | NE2 | HIS | X | 131 | −2.233 | 55.820 | 39.294 | 1.00 | 23.52 | N |
| ATOM | 958 | CD2 | HIS | X | 131 | −1.220 | 55.344 | 38.494 | 1.00 | 20.68 | C |
| ATOM | 959 | C | HIS | X | 131 | 1.897 | 56.177 | 38.201 | 1.00 | 17.25 | C |
| ATOM | 960 | O | HIS | X | 131 | 2.167 | 56.183 | 36.997 | 1.00 | 17.72 | O |
| ATOM | 961 | N | GLN | X | 132 | 1.368 | 57.231 | 38.830 | 1.00 | 16.69 | N |
| ATOM | 962 | CA | GLN | X | 132 | 0.979 | 58.443 | 38.095 | 1.00 | 16.49 | C |
| ATOM | 963 | CB | GLN | X | 132 | 0.175 | 59.428 | 38.969 | 1.00 | 16.53 | C |
| ATOM | 964 | CG | GLN | X | 132 | −0.312 | 60.706 | 38.239 | 1.00 | 16.83 | C |
| ATOM | 965 | CD | GLN | X | 132 | −1.490 | 60.452 | 37.299 | 1.00 | 17.26 | C |
| ATOM | 966 | OE1 | GLN | X | 132 | −2.359 | 59.630 | 37.585 | 1.00 | 19.31 | O |
| ATOM | 967 | NE2 | GLN | X | 132 | −1.524 | 61.162 | 36.179 | 1.00 | 15.76 | N |
| ATOM | 968 | C | GLN | X | 132 | 2.181 | 59.111 | 37.406 | 1.00 | 16.10 | C |
| ATOM | 969 | O | GLN | X | 132 | 2.157 | 59.255 | 36.188 | 1.00 | 16.02 | O |
| ATOM | 970 | N | PRO | X | 133 | 3.229 | 59.514 | 38.174 | 1.00 | 15.88 | N |
| ATOM | 971 | CA | PRO | X | 133 | 4.436 | 60.074 | 37.536 | 1.00 | 15.39 | C |
| ATOM | 972 | CB | PRO | X | 133 | 5.405 | 60.294 | 38.711 | 1.00 | 15.57 | C |
| ATOM | 973 | CG | PRO | X | 133 | 4.829 | 59.557 | 39.862 | 1.00 | 16.05 | C |
| ATOM | 974 | CD | PRO | X | 133 | 3.350 | 59.520 | 39.645 | 1.00 | 15.63 | C |
| ATOM | 975 | C | PRO | X | 133 | 5.085 | 59.161 | 36.503 | 1.00 | 14.99 | C |
| ATOM | 976 | O | PRO | X | 133 | 5.538 | 59.652 | 35.478 | 1.00 | 15.33 | O |
| ATOM | 977 | N | LEU | X | 134 | 5.130 | 57.856 | 36.772 | 1.00 | 14.60 | N |
| ATOM | 978 | CA | LEU | X | 134 | 5.691 | 56.889 | 35.837 | 1.00 | 14.62 | C |
| ATOM | 979 | CB | LEU | X | 134 | 5.780 | 55.485 | 36.462 | 1.00 | 14.13 | C |
| ATOM | 980 | CG | LEU | X | 134 | 6.857 | 55.209 | 37.520 | 1.00 | 14.87 | C |
| ATOM | 981 | CD1 | LEU | X | 134 | 6.728 | 53.784 | 38.025 | 1.00 | 13.28 | C |
| ATOM | 982 | CD2 | LEU | X | 134 | 8.271 | 55.445 | 36.995 | 1.00 | 11.76 | C |
| ATOM | 983 | C | LEU | X | 134 | 4.898 | 56.822 | 34.539 | 1.00 | 14.42 | C |
| ATOM | 984 | O | LEU | X | 134 | 5.479 | 56.719 | 33.470 | 1.00 | 14.32 | O |
| ATOM | 985 | N | THR | X | 135 | 3.572 | 56.861 | 34.634 | 1.00 | 14.68 | N |
| ATOM | 986 | CA | THR | X | 135 | 2.752 | 56.780 | 33.431 | 1.00 | 14.87 | C |
| ATOM | 987 | CB | THR | X | 135 | 1.281 | 56.455 | 33.743 | 1.00 | 14.78 | C |
| ATOM | 988 | OG1 | THR | X | 135 | 1.227 | 55.306 | 34.594 | 1.00 | 16.39 | O |
| ATOM | 989 | CG2 | THR | X | 135 | 0.511 | 56.155 | 32.461 | 1.00 | 14.96 | C |
| ATOM | 990 | C | THR | X | 135 | 2.879 | 58.075 | 32.640 | 1.00 | 14.75 | C |
| ATOM | 991 | O | THR | X | 135 | 3.002 | 58.040 | 31.423 | 1.00 | 14.14 | O |
| ATOM | 992 | N | GLU | X | 136 | 2.876 | 59.207 | 33.347 | 1.00 | 14.94 | N |
| ATOM | 993 | CA | GLU | X | 136 | 3.068 | 60.506 | 32.709 | 1.00 | 15.53 | C |
| ATOM | 994 | CB | GLU | X | 136 | 2.861 | 61.666 | 33.701 | 1.00 | 15.40 | C |
| ATOM | 995 | CG | GLU | X | 136 | 1.420 | 61.797 | 34.192 | 1.00 | 16.02 | C |
| ATOM | 996 | CD | GLU | X | 136 | 1.098 | 63.150 | 34.818 | 1.00 | 16.58 | C |
| ATOM | 997 | OE1 | GLU | X | 136 | 1.778 | 64.155 | 34.508 | 1.00 | 17.87 | O |
| ATOM | 998 | OE2 | GLU | X | 136 | 0.149 | 63.203 | 35.627 | 1.00 | 17.77 | O |
| ATOM | 999 | C | GLU | X | 136 | 4.442 | 60.577 | 32.049 | 1.00 | 15.56 | C |
| ATOM | 1000 | O | GLU | X | 136 | 4.562 | 61.979 | 30.935 | 1.00 | 15.79 | O |
| ATOM | 1001 | N | ALA | X | 137 | 5.463 | 60.045 | 32.727 | 1.00 | 15.57 | N |
| ATOM | 1002 | CA | ALA | X | 137 | 6.819 | 59.965 | 32.175 | 1.00 | 16.00 | C |
| ATOM | 1003 | CB | ALA | X | 137 | 7.767 | 59.301 | 33.173 | 1.00 | 15.62 | C |
| ATOM | 1004 | C | ALA | X | 137 | 6.862 | 59.219 | 30.842 | 1.00 | 16.37 | C |
| ATOM | 1005 | O | ALA | X | 137 | 7.570 | 59.625 | 29.916 | 1.00 | 16.31 | O |
| ATOM | 1006 | N | SER | X | 138 | 6.115 | 58.120 | 30.763 | 1.00 | 16.92 | N |
| ATOM | 1007 | CA | SER | X | 138 | 6.014 | 57.344 | 29.532 | 1.00 | 18.02 | C |
| ATOM | 1008 | CB | SER | X | 138 | 5.191 | 56.079 | 29.748 | 1.00 | 18.15 | C |
| ATOM | 1009 | OG | SER | X | 138 | 5.486 | 55.160 | 28.709 | 1.00 | 22.02 | O |
| ATOM | 1010 | C | SER | X | 138 | 5.404 | 58.154 | 28.391 | 1.00 | 17.61 | C |
| ATOM | 1011 | O | SER | X | 138 | 5.863 | 58.053 | 27.254 | 1.00 | 18.11 | O |
| ATOM | 1012 | N | TYR | X | 139 | 4.377 | 58.949 | 28.700 | 1.00 | 17.08 | N |
| ATOM | 1013 | CA | TYR | X | 139 | 3.731 | 59.827 | 27.713 | 1.00 | 16.78 | C |
| ATOM | 1014 | CB | TYR | X | 139 | 2.561 | 60.592 | 28.352 | 1.00 | 16.51 | C |
| ATOM | 1015 | CG | TYR | X | 139 | 1.251 | 59.842 | 28.403 | 1.00 | 16.85 | C |
| ATOM | 1016 | CD1 | TYR | X | 139 | 1.211 | 58.465 | 28.644 | 1.00 | 17.24 | C |
| ATOM | 1017 | CE1 | TYR | X | 139 | 0.000 | 57.783 | 28.700 | 1.00 | 16.10 | C |
| ATOM | 1018 | CZ | TYR | X | 139 | −1.175 | 58.475 | 28.530 | 1.00 | 15.99 | C |
| ATOM | 1019 | OH | TYR | X | 139 | −2.365 | 57.801 | 28.585 | 1.00 | 16.80 | O |

APPENDIX 1-continued

X-RAY DATA COORDINATES FOR LRP-220 (SEQ ID NO: 5)

| ATOM | 1020 | CE2 | TYR | X | 139 | −1.166 | 59.836 | 28.302 | 1.00 | 16.70 | C |
|---|---|---|---|---|---|---|---|---|---|---|---|
| ATOM | 1021 | CD2 | TYR | X | 139 | 0.043 | 60.513 | 28.245 | 1.00 | 16.75 | C |
| ATOM | 1022 | C | TYR | X | 139 | 4.696 | 60.843 | 27.120 | 1.00 | 16.51 | C |
| ATOM | 1023 | O | TYR | X | 139 | 4.581 | 61.191 | 25.952 | 1.00 | 16.27 | O |
| ATOM | 1024 | N | VAL | X | 140 | 5.640 | 61.323 | 27.932 | 1.00 | 16.43 | N |
| ATOM | 1025 | CA | VAL | X | 140 | 6.535 | 62.412 | 27.506 | 1.00 | 16.24 | C |
| ATOM | 1026 | CB | VAL | X | 140 | 6.489 | 63.629 | 28.501 | 1.00 | 16.11 | C |
| ATOM | 1027 | CG1 | VAL | X | 140 | 5.067 | 64.193 | 28.598 | 1.00 | 16.15 | C |
| ATOM | 1028 | CG2 | VAL | X | 140 | 7.006 | 63.245 | 29.894 | 1.00 | 15.19 | C |
| ATOM | 1029 | C | VAL | X | 140 | 7.983 | 61.970 | 27.222 | 1.00 | 16.22 | C |
| ATOM | 1030 | O | VAL | X | 140 | 8.869 | 62.815 | 27.080 | 1.00 | 16.85 | O |
| ATOM | 1031 | N | ASN | X | 141 | 8.206 | 60.657 | 27.129 | 1.00 | 16.23 | N |
| ATOM | 1032 | CA | ASN | X | 141 | 9.540 | 60.066 | 26.927 | 1.00 | 16.12 | C |
| ATOM | 1033 | CB | ASN | X | 141 | 10.080 | 60.353 | 25.510 | 1.00 | 16.81 | C |
| ATOM | 1034 | CG | ASN | X | 141 | 9.140 | 59.874 | 24.405 | 1.00 | 18.10 | C |
| ATOM | 1035 | OD1 | ASN | X | 141 | 8.430 | 58.882 | 24.558 | 1.00 | 21.41 | O |
| ATOM | 1036 | ND2 | ASN | X | 141 | 9.146 | 60.579 | 23.284 | 1.00 | 19.83 | N |
| ATOM | 1037 | C | ASN | X | 141 | 10.566 | 60.491 | 28.001 | 1.00 | 15.49 | C |
| ATOM | 1038 | O | ASN | X | 141 | 11.721 | 60.799 | 27.700 | 1.00 | 15.25 | O |
| ATOM | 1039 | N | LEU | X | 142 | 10.120 | 60.514 | 29.252 | 1.00 | 14.66 | N |
| ATOM | 1040 | CA | LEU | X | 142 | 10.995 | 60.776 | 30.382 | 1.00 | 13.74 | C |
| ATOM | 1041 | CB | LEU | X | 142 | 10.224 | 61.539 | 31.463 | 1.00 | 13.57 | C |
| ATOM | 1042 | CG | LEU | X | 142 | 10.825 | 61.692 | 32.868 | 1.00 | 13.66 | C |
| ATOM | 1043 | CD1 | LEU | X | 142 | 12.170 | 62.397 | 32.820 | 1.00 | 11.49 | C |
| ATOM | 1044 | CD2 | LEU | X | 142 | 9.858 | 62.428 | 33.774 | 1.00 | 13.24 | C |
| ATOM | 1045 | C | LEU | X | 142 | 11.510 | 59.422 | 30.900 | 1.00 | 13.56 | C |
| ATOM | 1046 | O | LEU | X | 142 | 10.712 | 58.586 | 31.327 | 1.00 | 13.44 | O |
| ATOM | 1047 | N | PRO | X | 143 | 12.837 | 59.187 | 30.832 | 1.00 | 13.26 | N |
| ATOM | 1048 | CA | PRO | X | 143 | 13.386 | 57.916 | 31.331 | 1.00 | 12.95 | C |
| ATOM | 1049 | CB | PRO | X | 143 | 14.883 | 58.028 | 31.019 | 1.00 | 13.14 | C |
| ATOM | 1050 | CG | PRO | X | 143 | 14.968 | 59.082 | 29.927 | 1.00 | 13.92 | C |
| ATOM | 1051 | CD | PRO | X | 143 | 13.896 | 60.060 | 30.299 | 1.00 | 13.17 | C |
| ATOM | 1052 | C | PRO | X | 143 | 13.180 | 57.755 | 32.832 | 1.00 | 12.52 | C |
| ATOM | 1053 | O | PRO | X | 143 | 13.219 | 58.741 | 33.574 | 1.00 | 11.53 | O |
| ATOM | 1054 | N | THR | X | 144 | 12.981 | 56.516 | 33.278 | 1.00 | 12.24 | N |
| ATOM | 1055 | CA | THR | X | 144 | 12.633 | 56.282 | 34.674 | 1.00 | 12.51 | C |
| ATOM | 1056 | CB | THR | X | 144 | 11.169 | 55.837 | 34.837 | 1.00 | 12.44 | C |
| ATOM | 1057 | OG1 | THR | X | 144 | 10.997 | 54.577 | 34.189 | 1.00 | 13.50 | O |
| ATOM | 1058 | CG2 | THR | X | 144 | 10.219 | 56.844 | 34.220 | 1.00 | 12.05 | C |
| ATOM | 1059 | C | THR | X | 144 | 13.506 | 55.239 | 35.342 | 1.00 | 12.57 | C |
| ATOM | 1060 | O | THR | X | 144 | 14.054 | 54.340 | 34.686 | 1.00 | 13.12 | O |
| ATOM | 1061 | N | ILE | X | 145 | 13.599 | 55.369 | 36.661 | 1.00 | 11.86 | N |
| ATOM | 1062 | CA | ILE | X | 145 | 14.301 | 54.432 | 37.528 | 1.00 | 11.40 | C |
| ATOM | 1063 | CB | ILE | X | 145 | 15.642 | 55.011 | 38.047 | 1.00 | 11.28 | C |
| ATOM | 1064 | CG1 | ILE | X | 145 | 16.557 | 55.385 | 36.869 | 1.00 | 11.42 | C |
| ATOM | 1065 | CD1 | ILE | X | 145 | 17.819 | 56.141 | 37.244 | 1.00 | 11.39 | C |
| ATOM | 1066 | CG2 | ILE | X | 145 | 16.327 | 54.013 | 38.997 | 1.00 | 11.28 | C |
| ATOM | 1067 | C | ILE | X | 145 | 13.366 | 54.206 | 38.698 | 1.00 | 11.06 | C |
| ATOM | 1068 | O | ILE | X | 145 | 12.713 | 55.139 | 39.159 | 1.00 | 11.09 | O |
| ATOM | 1069 | N | ALA | X | 146 | 13.276 | 52.970 | 39.171 | 1.00 | 10.74 | N |
| ATOM | 1070 | CA | ALA | X | 146 | 12.411 | 52.690 | 40.308 | 1.00 | 10.92 | C |
| ATOM | 1071 | CB | ALA | X | 146 | 11.000 | 52.297 | 39.848 | 1.00 | 9.62 | C |
| ATOM | 1072 | C | ALA | X | 146 | 12.993 | 51.605 | 41.183 | 1.00 | 10.87 | C |
| ATOM | 1073 | O | ALA | X | 146 | 13.660 | 50.699 | 40.701 | 1.00 | 10.77 | O |
| ATOM | 1074 | N | LEU | X | 147 | 12.728 | 51.731 | 42.474 | 1.00 | 11.43 | N |
| ATOM | 1075 | CA | LEU | X | 147 | 12.900 | 50.649 | 43.424 | 1.00 | 12.11 | C |
| ATOM | 1076 | CB | LEU | X | 147 | 12.810 | 51.188 | 44.859 | 1.00 | 11.61 | C |
| ATOM | 1077 | CG | LEU | X | 147 | 13.823 | 52.263 | 45.282 | 1.00 | 11.49 | C |
| ATOM | 1078 | CD1 | LEU | X | 147 | 13.646 | 52.592 | 46.768 | 1.00 | 10.96 | C |
| ATOM | 1079 | CD2 | LEU | X | 147 | 15.267 | 51.829 | 44.982 | 1.00 | 9.30 | C |
| ATOM | 1080 | C | LEU | X | 147 | 11.772 | 49.663 | 43.163 | 1.00 | 12.57 | C |
| ATOM | 1081 | O | LEU | X | 147 | 10.599 | 50.024 | 43.254 | 1.00 | 13.01 | O |
| ATOM | 1082 | N | CYS | X | 148 | 12.120 | 48.425 | 42.834 | 1.00 | 13.23 | N |
| ATOM | 1083 | CA | CYS | X | 148 | 11.120 | 47.457 | 42.398 | 1.00 | 13.55 | C |
| ATOM | 1084 | CB | CYS | X | 148 | 11.357 | 47.064 | 40.941 | 1.00 | 13.85 | C |
| ATOM | 1085 | SG | CYS | X | 148 | 11.109 | 48.395 | 39.766 | 1.00 | 14.86 | S |
| ATOM | 1086 | C | CYS | X | 148 | 11.107 | 46.210 | 43.260 | 1.00 | 13.86 | C |
| ATOM | 1087 | O | CYS | X | 148 | 12.135 | 45.536 | 43.418 | 1.00 | 14.09 | O |
| ATOM | 1088 | N | ASN | X | 149 | 9.933 | 45.910 | 43.803 | 1.00 | 13.71 | N |
| ATOM | 1089 | CA | ASN | X | 149 | 9.699 | 44.676 | 44.532 | 1.00 | 14.37 | C |
| ATOM | 1090 | CB | ASN | X | 149 | 8.567 | 44.863 | 45.555 | 1.00 | 13.99 | C |
| ATOM | 1091 | CG | ASN | X | 149 | 8.790 | 44.056 | 46.828 | 1.00 | 14.12 | C |
| ATOM | 1092 | OD1 | ASN | X | 149 | 9.282 | 42.930 | 46.781 | 1.00 | 13.09 | O |
| ATOM | 1093 | ND2 | ASN | X | 149 | 8.426 | 44.629 | 47.968 | 1.00 | 13.05 | N |
| ATOM | 1094 | C | ASN | X | 149 | 9.376 | 43.545 | 43.551 | 1.00 | 14.94 | C |
| ATOM | 1095 | O | ASN | X | 149 | 9.238 | 43.784 | 42.346 | 1.00 | 14.75 | O |
| ATOM | 1096 | N | THR | X | 150 | 9.249 | 42.320 | 44.058 | 1.00 | 15.51 | N |
| ATOM | 1097 | CA | THR | X | 150 | 9.016 | 41.159 | 43.183 | 1.00 | 16.22 | C |

APPENDIX 1-continued

X-RAY DATA COORDINATES FOR LRP-220 (SEQ ID NO: 5)

| ATOM | 1098 | CB | THR | X | 150 | 9.097 | 39.818 | 43.953 | 1.00 | 16.08 | C |
|---|---|---|---|---|---|---|---|---|---|---|---|
| ATOM | 1099 | OG1 | THR | X | 150 | 8.102 | 39.796 | 44.982 | 1.00 | 15.68 | O |
| ATOM | 1100 | CG2 | THR | X | 150 | 10.477 | 39.646 | 44.563 | 1.00 | 15.55 | C |
| ATOM | 1101 | C | THR | X | 150 | 7.701 | 41.231 | 42.405 | 1.00 | 16.74 | C |
| ATOM | 1102 | O | THR | X | 150 | 7.619 | 40.733 | 41.286 | 1.00 | 16.41 | O |
| ATOM | 1103 | N | ASP | X | 151 | 6.687 | 41.859 | 42.995 | 1.00 | 17.93 | N |
| ATOM | 1104 | CA | ASP | X | 151 | 5.398 | 42.032 | 42.328 | 1.00 | 19.59 | C |
| ATOM | 1105 | CB | ASP | X | 151 | 4.254 | 41.705 | 43.288 | 1.00 | 20.07 | C |
| ATOM | 1106 | CG | ASP | X | 151 | 4.158 | 42.690 | 44.438 | 1.00 | 22.98 | C |
| ATOM | 1107 | OD1 | ASP | X | 151 | 3.104 | 42.715 | 45.116 | 1.00 | 27.10 | O |
| ATOM | 1108 | OD2 | ASP | X | 151 | 5.135 | 43.429 | 44.686 | 1.00 | 25.50 | O |
| ATOM | 1109 | C | ASP | X | 151 | 5.193 | 43.436 | 41.745 | 1.00 | 19.86 | C |
| ATOM | 1110 | O | ASP | X | 151 | 4.067 | 43.797 | 41.381 | 1.00 | 20.26 | O |
| ATOM | 1111 | N | SER | X | 152 | 6.264 | 44.226 | 41.668 | 1.00 | 19.95 | N |
| ATOM | 1112 | CA | SER | X | 152 | 6.185 | 45.559 | 41.063 | 1.00 | 19.88 | C |
| ATOM | 1113 | CB | SER | X | 152 | 7.465 | 46.361 | 41.299 | 1.00 | 19.46 | C |
| ATOM | 1114 | OG | SER | X | 152 | 7.505 | 46.882 | 42.616 | 1.00 | 19.58 | O |
| ATOM | 1115 | C | SER | X | 152 | 5.935 | 45.431 | 39.575 | 1.00 | 19.99 | C |
| ATOM | 1116 | O | SER | X | 152 | 6.546 | 44.589 | 38.916 | 1.00 | 20.27 | O |
| ATOM | 1117 | N | PRO | X | 153 | 5.019 | 46.253 | 39.038 | 1.00 | 20.10 | N |
| ATOM | 1118 | CA | PRO | X | 153 | 4.888 | 46.328 | 37.583 | 1.00 | 20.13 | C |
| ATOM | 1119 | CB | PRO | X | 153 | 3.572 | 47.095 | 37.397 | 1.00 | 20.02 | C |
| ATOM | 1120 | CG | PRO | X | 153 | 3.467 | 47.960 | 38.620 | 1.00 | 20.52 | C |
| ATOM | 1121 | CD | PRO | X | 153 | 4.060 | 47.132 | 39.737 | 1.00 | 20.09 | C |
| ATOM | 1122 | C | PRO | X | 153 | 6.068 | 47.100 | 36.974 | 1.00 | 20.13 | C |
| ATOM | 1123 | O | PRO | X | 153 | 6.397 | 48.201 | 37.442 | 1.00 | 20.58 | O |
| ATOM | 1124 | N | LEU | X | 154 | 6.701 | 46.527 | 35.953 | 1.00 | 19.88 | N |
| ATOM | 1125 | CA | LEU | X | 154 | 7.877 | 47.140 | 35.340 | 1.00 | 19.68 | C |
| ATOM | 1126 | CB | LEU | X | 154 | 9.006 | 46.116 | 35.137 | 1.00 | 19.67 | C |
| ATOM | 1127 | CG | LEU | X | 154 | 9.708 | 45.441 | 36.325 | 1.00 | 19.69 | C |
| ATOM | 1128 | CD1 | LEU | X | 154 | 11.099 | 44.947 | 35.932 | 1.00 | 18.97 | C |
| ATOM | 1129 | CD2 | LEU | X | 154 | 9.814 | 46.371 | 37.505 | 1.00 | 19.52 | C |
| ATOM | 1130 | C | LEU | X | 154 | 7.556 | 47.822 | 34.016 | 1.00 | 19.52 | C |
| ATOM | 1131 | O | LEU | X | 154 | 8.455 | 48.298 | 33.324 | 1.00 | 19.51 | O |
| ATOM | 1132 | N | ARG | X | 155 | 6.273 | 47.855 | 33.669 | 1.00 | 19.21 | N |
| ATOM | 1133 | CA | ARG | X | 155 | 5.807 | 48.440 | 32.414 | 1.00 | 18.99 | C |
| ATOM | 1134 | CB | ARG | X | 155 | 4.280 | 48.525 | 32.420 | 1.00 | 19.06 | C |
| ATOM | 1135 | CG | ARG | X | 155 | 3.690 | 49.105 | 31.143 | 1.00 | 20.28 | C |
| ATOM | 1136 | CD | ARG | X | 155 | 2.234 | 48.738 | 31.015 | 1.00 | 22.06 | C |
| ATOM | 1137 | NE | ARG | X | 155 | 2.086 | 47.302 | 30.790 | 1.00 | 22.67 | N |
| ATOM | 1138 | CZ | ARG | X | 155 | 0.966 | 46.619 | 30.985 | 1.00 | 23.37 | C |
| ATOM | 1139 | NH1 | ARG | X | 155 | −0.130 | 47.229 | 31.415 | 1.00 | 23.18 | N |
| ATOM | 1140 | NH2 | ARG | X | 155 | 0.951 | 45.310 | 30.758 | 1.00 | 24.79 | N |
| ATOM | 1141 | C | ARG | X | 155 | 6.409 | 49.820 | 32.100 | 1.00 | 18.45 | C |
| ATOM | 1142 | O | ARG | X | 155 | 6.827 | 50.076 | 30.968 | 1.00 | 18.62 | O |
| ATOM | 1143 | N | TYR | X | 156 | 6.446 | 50.693 | 33.106 | 1.00 | 17.73 | N |
| ATOM | 1144 | CA | TYR | X | 156 | 6.878 | 52.085 | 32.939 | 1.00 | 16.79 | C |
| ATOM | 1145 | CB | TYR | X | 156 | 5.847 | 53.023 | 33.571 | 1.00 | 16.48 | C |
| ATOM | 1146 | CG | TYR | X | 156 | 4.451 | 52.845 | 33.010 | 1.00 | 16.91 | C |
| ATOM | 1147 | CD1 | TYR | X | 156 | 4.178 | 53.106 | 31.666 | 1.00 | 16.32 | C |
| ATOM | 1148 | CE1 | TYR | X | 156 | 2.898 | 52.940 | 31.144 | 1.00 | 15.84 | C |
| ATOM | 1149 | CZ | TYR | X | 156 | 1.878 | 52.504 | 31.965 | 1.00 | 16.74 | C |
| ATOM | 1150 | OH | TYR | X | 156 | 0.610 | 52.348 | 31.456 | 1.00 | 16.88 | O |
| ATOM | 1151 | CE2 | TYR | X | 156 | 2.120 | 52.230 | 33.302 | 1.00 | 17.26 | C |
| ATOM | 1152 | CD2 | TYR | X | 156 | 3.405 | 52.402 | 33.818 | 1.00 | 17.69 | C |
| ATOM | 1153 | C | TYR | X | 156 | 8.264 | 52.348 | 33.526 | 1.00 | 16.33 | C |
| ATOM | 1154 | O | TYR | X | 156 | 8.699 | 53.504 | 33.631 | 1.00 | 16.24 | O |
| ATOM | 1155 | N | VAL | X | 157 | 8.951 | 51.273 | 33.896 | 1.00 | 15.40 | N |
| ATOM | 1156 | CA | VAL | X | 157 | 10.264 | 51.363 | 34.529 | 1.00 | 15.08 | C |
| ATOM | 1157 | CB | VAL | X | 157 | 10.365 | 50.408 | 35.768 | 1.00 | 14.94 | C |
| ATOM | 1158 | CG1 | VAL | X | 157 | 11.780 | 50.436 | 36.362 | 1.00 | 14.49 | C |
| ATOM | 1159 | CG2 | VAL | X | 157 | 9.324 | 50.769 | 36.830 | 1.00 | 13.72 | C |
| ATOM | 1160 | C | VAL | X | 157 | 11.342 | 51.001 | 33.505 | 1.00 | 15.43 | C |
| ATOM | 1161 | O | VAL | X | 157 | 11.306 | 49.903 | 32.942 | 1.00 | 15.27 | O |
| ATOM | 1162 | N | ASP | X | 158 | 12.286 | 51.918 | 33.268 | 1.00 | 15.20 | N |
| ATOM | 1163 | CA | ASP | X | 158 | 13.423 | 51.656 | 32.372 | 1.00 | 15.42 | C |
| ATOM | 1164 | CB | ASP | X | 158 | 13.912 | 52.946 | 31.685 | 1.00 | 15.78 | C |
| ATOM | 1165 | CG | ASP | X | 158 | 12.840 | 53.602 | 30.811 | 1.00 | 17.28 | C |
| ATOM | 1166 | OD1 | ASP | X | 158 | 12.315 | 52.959 | 29.869 | 1.00 | 18.93 | O |
| ATOM | 1167 | OD2 | ASP | X | 158 | 12.530 | 54.780 | 31.057 | 1.00 | 18.99 | O |
| ATOM | 1168 | C | ASP | X | 158 | 14.590 | 50.973 | 33.106 | 1.00 | 15.10 | C |
| ATOM | 1169 | O | ASP | X | 158 | 15.176 | 50.005 | 32.598 | 1.00 | 15.16 | O |
| ATOM | 1170 | N | ILE | X | 159 | 14.942 | 51.488 | 34.282 | 1.00 | 14.23 | N |
| ATOM | 1171 | CA | ILE | X | 159 | 15.939 | 50.838 | 35.125 | 1.00 | 13.89 | C |
| ATOM | 1172 | CB | ILE | X | 159 | 17.174 | 51.732 | 35.426 | 1.00 | 14.16 | C |
| ATOM | 1173 | CG1 | ILE | X | 159 | 17.942 | 52.079 | 34.139 | 1.00 | 13.81 | C |
| ATOM | 1174 | CD1 | ILE | X | 159 | 18.986 | 53.186 | 34.338 | 1.00 | 13.96 | C |
| ATOM | 1175 | CG2 | ILE | X | 159 | 18.101 | 51.034 | 36.446 | 1.00 | 13.94 | C |

APPENDIX 1-continued

X-RAY DATA COORDINATES FOR LRP-220 (SEQ ID NO: 5)

| ATOM | 1176 | C   | ILE | X | 159 | 15.285 | 50.416 | 36.432 | 1.00 | 13.63 | C |
|------|------|-----|-----|---|-----|--------|--------|--------|------|-------|---|
| ATOM | 1177 | O   | ILE | X | 159 | 14.884 | 51.267 | 37.238 | 1.00 | 13.47 | O |
| ATOM | 1178 | N   | ALA | X | 160 | 15.168 | 49.102 | 36.618 | 1.00 | 13.06 | N |
| ATOM | 1179 | CA  | ALA | X | 160 | 14.592 | 48.513 | 37.828 | 1.00 | 13.00 | C |
| ATOM | 1180 | CB  | ALA | X | 160 | 13.784 | 47.269 | 37.476 | 1.00 | 12.71 | C |
| ATOM | 1181 | C   | ALA | X | 160 | 15.687 | 48.159 | 38.822 | 1.00 | 12.72 | C |
| ATOM | 1182 | O   | ALA | X | 160 | 16.635 | 47.448 | 38.480 | 1.00 | 13.40 | O |
| ATOM | 1183 | N   | ILE | X | 161 | 15.566 | 48.673 | 40.040 | 1.00 | 12.22 | N |
| ATOM | 1184 | CA  | ILE | X | 161 | 16.452 | 48.295 | 41.126 | 1.00 | 12.07 | C |
| ATOM | 1185 | CB  | ILE | X | 161 | 16.933 | 49.525 | 41.952 | 1.00 | 11.98 | C |
| ATOM | 1186 | CG1 | ILE | X | 161 | 17.521 | 50.607 | 41.038 | 1.00 | 11.82 | C |
| ATOM | 1187 | CD1 | ILE | X | 161 | 17.733 | 51.946 | 41.727 | 1.00 | 11.76 | C |
| ATOM | 1188 | CG2 | ILE | X | 161 | 17.979 | 49.097 | 42.968 | 1.00 | 12.04 | C |
| ATOM | 1189 | C   | ILE | X | 161 | 15.679 | 47.310 | 42.024 | 1.00 | 12.00 | C |
| ATOM | 1190 | O   | ILE | X | 161 | 14.774 | 47.719 | 42.749 | 1.00 | 11.80 | O |
| ATOM | 1191 | N   | PRO | X | 162 | 16.018 | 46.008 | 41.955 | 1.00 | 12.25 | N |
| ATOM | 1192 | CA  | PRO | X | 162 | 15.244 | 45.021 | 42.712 | 1.00 | 12.11 | C |
| ATOM | 1193 | CB  | PRO | X | 162 | 15.699 | 43.686 | 42.121 | 1.00 | 12.20 | C |
| ATOM | 1194 | CG  | PRO | X | 162 | 17.072 | 43.946 | 41.591 | 1.00 | 11.87 | C |
| ATOM | 1195 | CD  | PRO | X | 162 | 17.107 | 45.385 | 41.175 | 1.00 | 12.06 | C |
| ATOM | 1196 | C   | PRO | X | 162 | 15.544 | 45.099 | 44.201 | 1.00 | 12.22 | C |
| ATOM | 1197 | O   | PRO | X | 162 | 16.711 | 45.093 | 44.597 | 1.00 | 12.32 | O |
| ATOM | 1198 | N   | CYS | X | 163 | 14.495 | 45.202 | 45.013 | 1.00 | 12.31 | N |
| ATOM | 1199 | CA  | CYS | X | 163 | 14.650 | 45.339 | 46.455 | 1.00 | 13.05 | C |
| ATOM | 1200 | CB  | CYS | X | 163 | 15.315 | 46.685 | 46.787 | 1.00 | 13.19 | C |
| ATOM | 1201 | SG  | CYS | X | 163 | 14.357 | 48.091 | 46.189 | 1.00 | 14.37 | S |
| ATOM | 1202 | C   | CYS | X | 163 | 13.302 | 45.258 | 47.166 | 1.00 | 13.21 | C |
| ATOM | 1203 | O   | CYS | X | 163 | 12.244 | 45.352 | 46.532 | 1.00 | 12.99 | O |
| ATOM | 1204 | N   | ASN | X | 164 | 13.355 | 45.070 | 48.484 | 1.00 | 13.29 | N |
| ATOM | 1205 | CA  | ASN | X | 164 | 12.220 | 45.353 | 49.355 | 1.00 | 13.54 | C |
| ATOM | 1206 | CB  | ASN | X | 164 | 12.531 | 44.883 | 50.783 | 1.00 | 13.28 | C |
| ATOM | 1207 | CG  | ASN | X | 164 | 11.386 | 45.130 | 51.769 | 1.00 | 13.91 | C |
| ATOM | 1208 | OD1 | ASN | X | 164 | 10.380 | 45.756 | 51.444 | 1.00 | 14.80 | O |
| ATOM | 1209 | ND2 | ASN | X | 164 | 11.553 | 44.638 | 52.994 | 1.00 | 13.95 | N |
| ATOM | 1210 | C   | ASN | X | 164 | 11.987 | 46.871 | 49.319 | 1.00 | 13.94 | C |
| ATOM | 1211 | O   | ASN | X | 164 | 12.741 | 47.640 | 49.926 | 1.00 | 14.14 | O |
| ATOM | 1212 | N   | ASN | X | 165 | 10.970 | 47.293 | 48.579 | 1.00 | 14.20 | N |
| ATOM | 1213 | CA  | ASN | X | 165 | 10.604 | 48.701 | 48.514 | 1.00 | 15.18 | C |
| ATOM | 1214 | CB  | ASN | X | 165 | 10.377 | 49.144 | 47.059 | 1.00 | 14.77 | C |
| ATOM | 1215 | CG  | ASN | X | 165 | 9.096  | 48.581 | 46.462 | 1.00 | 15.34 | C |
| ATOM | 1216 | OD1 | ASN | X | 165 | 8.433  | 47.737 | 47.061 | 1.00 | 17.22 | O |
| ATOM | 1217 | ND2 | ASN | X | 165 | 8.741  | 49.052 | 45.274 | 1.00 | 16.27 | N |
| ATOM | 1218 | C   | ASN | X | 165 | 9.360  | 48.988 | 49.364 | 1.00 | 15.88 | C |
| ATOM | 1219 | O   | ASN | X | 165 | 8.702  | 50.011 | 49.175 | 1.00 | 16.07 | O |
| ATOM | 1220 | N   | LYS | X | 166 | 9.049  | 48.074 | 50.284 | 1.00 | 16.53 | N |
| ATOM | 1221 | CA  | LYS | X | 166 | 7.898  | 48.202 | 51.169 | 1.00 | 17.51 | C |
| ATOM | 1222 | CB  | LYS | X | 166 | 7.095  | 46.896 | 51.176 | 1.00 | 17.80 | C |
| ATOM | 1223 | CG  | LYS | X | 166 | 5.864  | 46.935 | 52.080 | 1.00 | 21.27 | C |
| ATOM | 1224 | CD  | LYS | X | 166 | 5.281  | 45.548 | 52.301 | 1.00 | 26.08 | C |
| ATOM | 1225 | CE  | LYS | K | 166 | 4.165  | 45.584 | 53.340 | 1.00 | 29.90 | C |
| ATOM | 1226 | NZ  | LYS | X | 166 | 3.050  | 46.503 | 52.943 | 1.00 | 32.28 | N |
| ATOM | 1227 | C   | LYS | X | 166 | 8.302  | 48.596 | 52.599 | 1.00 | 17.32 | C |
| ATOM | 1228 | O   | LYS | X | 166 | 7.784  | 49.564 | 53.156 | 1.00 | 17.63 | O |
| ATOM | 1229 | N   | GLY | X | 167 | 9.226  | 47.846 | 53.190 | 1.00 | 17.29 | N |
| ATOM | 1230 | CA  | GLY | X | 167 | 9.652  | 48.098 | 54.569 | 1.00 | 16.94 | C |
| ATOM | 1231 | C   | GLY | X | 167 | 10.373 | 49.424 | 54.690 | 1.00 | 16.73 | C |
| ATOM | 1232 | O   | GLY | X | 167 | 11.108 | 49.820 | 53.782 | 1.00 | 16.04 | O |
| ATOM | 1233 | N   | ALA | X | 168 | 10.168 | 50.102 | 55.820 | 1.00 | 16.45 | N |
| ATOM | 1234 | CA  | ALA | X | 168 | 10.729 | 51.437 | 56.050 | 1.00 | 16.34 | C |
| ATOM | 1235 | CB  | ALA | X | 168 | 10.155 | 52.050 | 57.339 | 1.00 | 16.64 | C |
| ATOM | 1236 | C   | ALA | X | 168 | 12.257 | 51.488 | 56.068 | 1.00 | 16.30 | C |
| ATOM | 1237 | O   | ALA | X | 168 | 12.858 | 52.397 | 55.483 | 1.00 | 15.90 | O |
| ATOM | 1238 | N   | HIS | X | 169 | 12.886 | 50.522 | 56.738 | 1.00 | 16.23 | N |
| ATOM | 1239 | CA  | HIS | X | 169 | 14.350 | 50.485 | 56.818 | 1.00 | 16.44 | C |
| ATOM | 1240 | CB  | HIS | X | 169 | 14.823 | 49.424 | 57.812 | 1.00 | 17.20 | C |
| ATOM | 1241 | CG  | HIS | X | 169 | 14.662 | 49.818 | 59.248 | 1.00 | 20.89 | C |
| ATOM | 1242 | ND1 | HIS | X | 169 | 15.450 | 49.296 | 60.250 | 1.00 | 24.67 | N |
| ATOM | 1243 | CE1 | HIS | X | 169 | 15.084 | 49.814 | 61.411 | 1.00 | 25.88 | C |
| ATOM | 1244 | NE2 | HIS | X | 169 | 14.091 | 50.658 | 61.197 | 1.00 | 25.28 | N |
| ATOM | 1245 | CD2 | HIS | X | 169 | 13.809 | 50.681 | 59.852 | 1.00 | 23.96 | C |
| ATOM | 1246 | C   | HIS | X | 169 | 14.983 | 50.240 | 55.451 | 1.00 | 15.63 | C |
| ATOM | 1247 | O   | HIS | X | 169 | 15.973 | 50.882 | 55.096 | 1.00 | 15.48 | O |
| ATOM | 1248 | N   | SER | X | 170 | 14.398 | 49.320 | 54.692 | 1.00 | 14.82 | N |
| ATOM | 1249 | CA  | SER | X | 170 | 14.895 | 48.982 | 53.360 | 1.00 | 14.35 | C |
| ATOM | 1250 | CB  | SER | X | 170 | 14.211 | 47.724 | 52.827 | 1.00 | 14.25 | C |
| ATOM | 1251 | OG  | SER | X | 170 | 14.739 | 47.364 | 51.560 | 1.00 | 15.22 | O |
| ATOM | 1252 | C   | SER | X | 170 | 14.737 | 50.145 | 52.381 | 1.00 | 13.75 | C |
| ATOM | 1253 | O   | SER | X | 170 | 15.668 | 50.455 | 51.647 | 1.00 | 13.52 | O |

APPENDIX 1-continued

X-RAY DATA COORDINATES FOR LRP-220 (SEQ ID NO: 5)

| ATOM | 1254 | N   | VAL | X | 171 | 13.569 | 50.788 | 52.375 | 1.00 | 13.45 | N |
|------|------|-----|-----|---|-----|--------|--------|--------|------|-------|---|
| ATOM | 1255 | CA  | VAL | X | 171 | 13.360 | 51.973 | 51.523 | 1.00 | 13.20 | C |
| ATOM | 1256 | CB  | VAL | X | 171 | 11.933 | 52.544 | 51.640 | 1.00 | 12.91 | C |
| ATOM | 1257 | CG1 | VAL | X | 171 | 11.823 | 53.920 | 50.950 | 1.00 | 13.68 | C |
| ATOM | 1258 | CG2 | VAL | X | 171 | 10.926 | 51.581 | 51.061 | 1.00 | 13.64 | C |
| ATOM | 1259 | C   | VAL | X | 171 | 14.386 | 53.057 | 51.850 | 1.00 | 12.85 | C |
| ATOM | 1260 | O   | VAL | X | 171 | 15.026 | 53.605 | 50.951 | 1.00 | 12.45 | O |
| ATOM | 1261 | N   | GLY | X | 172 | 14.542 | 53.356 | 53.137 | 1.00 | 12.67 | N |
| ATOM | 1262 | CA  | GLY | X | 172 | 15.489 | 54.386 | 53.577 | 1.00 | 12.48 | C |
| ATOM | 1263 | C   | GLY | X | 172 | 16.921 | 54.052 | 53.199 | 1.00 | 12.33 | C |
| ATOM | 1264 | O   | GLY | X | 172 | 17.664 | 54.914 | 52.719 | 1.00 | 12.19 | O |
| ATOM | 1265 | N   | LEU | X | 173 | 17.297 | 52.792 | 53.402 | 1.00 | 12.45 | N |
| ATOM | 1266 | CA  | LEU | X | 173 | 18.639 | 52.313 | 53.075 | 1.00 | 12.79 | C |
| ATOM | 1267 | CB  | LEU | X | 173 | 18.847 | 50.875 | 53.560 | 1.00 | 12.76 | C |
| ATOM | 1268 | CG  | LEU | X | 173 | 20.166 | 50.183 | 53.164 | 1.00 | 13.27 | C |
| ATOM | 1269 | CD1 | LEU | X | 173 | 21.357 | 50.818 | 53.885 | 1.00 | 13.69 | C |
| ATOM | 1270 | CD2 | LEU | X | 173 | 20.104 | 48.675 | 53.440 | 1.00 | 12.89 | C |
| ATOM | 1271 | C   | LEU | X | 173 | 18.918 | 52.397 | 51.579 | 1.00 | 12.76 | C |
| ATOM | 1272 | O   | LEU | X | 173 | 20.017 | 52.778 | 51.176 | 1.00 | 13.12 | O |
| ATOM | 1273 | N   | MET | X | 174 | 17.929 | 52.034 | 50.763 | 1.00 | 12.59 | N |
| ATOM | 1274 | CA  | MET | X | 174 | 18.102 | 52.059 | 49.308 | 1.00 | 12.69 | C |
| ATOM | 1275 | CB  | MET | X | 174 | 16.875 | 51.479 | 48.591 | 1.00 | 12.53 | C |
| ATOM | 1276 | CG  | MET | X | 174 | 16.734 | 49.947 | 48.706 | 1.00 | 12.61 | C |
| ATOM | 1277 | SD  | MET | X | 174 | 18.170 | 48.973 | 48.177 | 1.00 | 13.33 | S |
| ATOM | 1278 | CE  | MET | X | 174 | 18.237 | 49.361 | 46.425 | 1.00 | 11.52 | C |
| ATOM | 1279 | C   | MET | X | 174 | 18.421 | 53.471 | 48.809 | 1.00 | 12.66 | C |
| ATOM | 1280 | O   | MET | X | 174 | 19.379 | 53.667 | 48.048 | 1.00 | 12.36 | O |
| ATOM | 1281 | N   | TRP | X | 175 | 17.628 | 54.446 | 49.258 | 1.00 | 12.66 | N |
| ATOM | 1282 | CA  | TRP | X | 175 | 17.836 | 55.850 | 48.896 | 1.00 | 13.00 | C |
| ATOM | 1283 | CB  | TRP | X | 175 | 16.670 | 56.711 | 49.395 | 1.00 | 12.45 | C |
| ATOM | 1284 | CG  | TRP | X | 175 | 15.474 | 56.665 | 48.486 | 1.00 | 11.86 | C |
| ATOM | 1285 | CD1 | TRP | X | 175 | 14.280 | 56.046 | 48.722 | 1.00 | 10.69 | C |
| ATOM | 1286 | NE1 | TRP | X | 175 | 13.431 | 56.225 | 47.653 | 1.00 | 10.74 | N |
| ATOM | 1287 | CE2 | TRP | X | 175 | 14.076 | 56.970 | 46.698 | 1.00 | 11.46 | C |
| ATOM | 1288 | CD2 | TRP | X | 175 | 15.365 | 57.269 | 47.193 | 1.00 | 11.64 | C |
| ATOM | 1289 | CE3 | TRP | X | 175 | 16.240 | 58.027 | 46.397 | 1.00 | 11.84 | C |
| ATOM | 1290 | CZ3 | TRP | X | 175 | 15.796 | 58.474 | 45.158 | 1.00 | 11.34 | C |
| ATOM | 1291 | CH2 | TRP | X | 175 | 14.500 | 58.164 | 44.696 | 1.00 | 11.34 | C |
| ATOM | 1292 | CZ2 | TRP | X | 175 | 13.632 | 57.413 | 45.444 | 1.00 | 11.62 | C |
| ATOM | 1293 | C   | TRP | X | 175 | 19.175 | 56.379 | 49.412 | 1.00 | 13.57 | C |
| ATOM | 1294 | O   | TRP | X | 175 | 19.878 | 57.098 | 48.706 | 1.00 | 14.02 | O |
| ATOM | 1295 | N   | TRP | X | 176 | 19.527 | 55.998 | 50.638 | 1.00 | 14.79 | N |
| ATOM | 1296 | CA  | TRP | X | 176 | 20.838 | 56.320 | 51.223 | 1.00 | 15.57 | C |
| ATOM | 1297 | CB  | TRP | X | 176 | 20.904 | 55.819 | 52.677 | 1.00 | 15.95 | C |
| ATOM | 1298 | CG  | TRP | X | 176 | 22.234 | 56.003 | 53.351 | 1.00 | 16.75 | C |
| ATOM | 1299 | CD1 | TRP | X | 176 | 22.640 | 57.084 | 54.089 | 1.00 | 17.25 | C |
| ATOM | 1300 | NE1 | TRP | X | 176 | 23.924 | 56.886 | 54.551 | 1.00 | 16.59 | N |
| ATOM | 1301 | CE2 | TRP | X | 176 | 24.369 | 55.664 | 54.121 | 1.00 | 16.79 | C |
| ATOM | 1302 | CD2 | TRP | X | 176 | 23.326 | 55.073 | 53.365 | 1.00 | 17.27 | C |
| ATOM | 1303 | CE3 | TRP | X | 176 | 23.528 | 53.798 | 52.811 | 1.00 | 16.82 | C |
| ATOM | 1304 | CZ3 | TRP | X | 176 | 24.752 | 53.159 | 53.025 | 1.00 | 16.49 | C |
| ATOM | 1305 | CH2 | TRP | X | 176 | 25.768 | 53.775 | 53.785 | 1.00 | 17.43 | C |
| ATOM | 1306 | CZ2 | TRP | X | 176 | 25.595 | 55.022 | 54.339 | 1.00 | 17.22 | C |
| ATOM | 1307 | C   | TRP | X | 176 | 21.986 | 55.745 | 50.385 | 1.00 | 15.71 | C |
| ATOM | 1308 | O   | TRP | X | 176 | 22.953 | 56.446 | 50.069 | 1.00 | 15.13 | O |
| ATOM | 1309 | N   | MET | X | 177 | 21.867 | 54.474 | 50.008 | 1.00 | 16.31 | N |
| ATOM | 1310 | CA  | MET | X | 177 | 22.900 | 53.831 | 49.199 | 1.00 | 17.65 | C |
| ATOM | 1311 | CB  | MET | X | 177 | 22.677 | 52.329 | 49.130 | 1.00 | 17.44 | C |
| ATOM | 1312 | CG  | MET | X | 177 | 23.975 | 51.559 | 49.074 | 1.00 | 19.87 | C |
| ATOM | 1313 | SD  | MET | X | 177 | 23.742 | 49.791 | 49.294 | 1.00 | 22.04 | S |
| ATOM | 1314 | CE  | MET | X | 177 | 23.557 | 49.637 | 51.067 | 1.00 | 21.57 | C |
| ATOM | 1315 | C   | MET | X | 177 | 23.013 | 54.425 | 47.791 | 1.00 | 16.68 | C |
| ATOM | 1316 | O   | MET | X | 177 | 24.119 | 54.573 | 47.263 | 1.00 | 16.13 | O |
| ATOM | 1317 | N   | LEU | X | 178 | 21.866 | 54.755 | 47.196 | 1.00 | 16.39 | N |
| ATOM | 1318 | CA  | LEU | X | 178 | 21.831 | 55.439 | 45.905 | 1.00 | 16.64 | C |
| ATOM | 1319 | CB  | LEU | X | 178 | 20.392 | 55.740 | 45.469 | 1.00 | 16.45 | C |
| ATOM | 1320 | CG  | LEU | X | 178 | 19.930 | 55.495 | 44.020 | 1.00 | 18.25 | C |
| ATOM | 1321 | CD1 | LEU | X | 178 | 18.855 | 56.495 | 43.575 | 1.00 | 16.38 | C |
| ATOM | 1322 | CD2 | LEU | X | 178 | 21.057 | 55.389 | 42.991 | 1.00 | 16.98 | C |
| ATOM | 1323 | C   | LEU | X | 178 | 22.603 | 56.747 | 46.016 | 1.00 | 16.16 | C |
| ATOM | 1324 | O   | LEU | X | 178 | 23.482 | 57.007 | 45.208 | 1.00 | 16.08 | O |
| ATOM | 1325 | N   | ALA | X | 179 | 22.265 | 57.548 | 47.028 | 1.00 | 16.24 | N |
| ATOM | 1326 | CA  | ALA | X | 179 | 22.939 | 58.832 | 47.300 | 1.00 | 16.51 | C |
| ATOM | 1327 | CB  | ALA | X | 179 | 22.335 | 59.510 | 48.542 | 1.00 | 16.39 | C |
| ATOM | 1328 | C   | ALA | X | 179 | 24.443 | 58.678 | 47.460 | 1.00 | 16.51 | C |
| ATOM | 1329 | O   | ALA | X | 179 | 25.215 | 59.402 | 46.829 | 1.00 | 16.60 | O |
| ATOM | 1330 | N   | ARG | X | 180 | 24.855 | 57.726 | 48.297 | 1.00 | 16.59 | N |
| ATOM | 1331 | CA  | ARG | X | 180 | 26.277 | 57.453 | 48.526 | 1.00 | 16.53 | C |

APPENDIX 1-continued

X-RAY DATA COORDINATES FOR LRP-220 (SEQ ID NO: 5)

| ATOM | 1332 | CB | ARG | X | 180 | 26.437 | 56.270 | 49.490 | 1.00 | 16.40 | C |
|---|---|---|---|---|---|---|---|---|---|---|---|
| ATOM | 1333 | CG | ARG | X | 180 | 27.846 | 56.088 | 50.056 | 1.00 | 16.13 | C |
| ATOM | 1334 | CD | ARG | X | 180 | 27.952 | 54.790 | 50.850 | 1.00 | 16.00 | C |
| ATOM | 1335 | NE | ARG | X | 180 | 27.730 | 53.637 | 49.988 | 1.00 | 17.01 | N |
| ATOM | 1336 | CZ | ARG | X | 180 | 27.668 | 52.370 | 50.395 | 1.00 | 18.18 | C |
| ATOM | 1337 | NH1 | ARG | X | 180 | 27.817 | 52.052 | 51.675 | 1.00 | 19.33 | N |
| ATOM | 1338 | NH2 | ARG | X | 180 | 27.467 | 51.413 | 49.507 | 1.00 | 18.03 | N |
| ATOM | 1339 | C | ARG | X | 180 | 27.026 | 57.170 | 47.221 | 1.00 | 16.69 | C |
| ATOM | 1340 | O | ARG | X | 180 | 28.132 | 57.681 | 47.008 | 1.00 | 17.18 | O |
| ATOM | 1341 | N | GLU | X | 181 | 26.423 | 56.357 | 46.353 | 1.00 | 16.97 | N |
| ATOM | 1342 | CA | GLU | X | 181 | 27.056 | 55.970 | 45.090 | 1.00 | 17.18 | C |
| ATOM | 1343 | CB | GLU | X | 181 | 26.392 | 54.725 | 44.483 | 1.00 | 16.83 | C |
| ATOM | 1344 | CG | GLU | X | 181 | 26.595 | 53.443 | 45.306 | 1.00 | 19.23 | C |
| ATOM | 1345 | CD | GLU | X | 181 | 28.046 | 53.213 | 45.726 | 1.00 | 19.32 | C |
| ATOM | 1346 | OE1 | GLU | X | 181 | 28.947 | 53.223 | 44.862 | 1.00 | 20.23 | O |
| ATOM | 1347 | OE2 | GLU | X | 181 | 28.280 | 53.009 | 46.926 | 1.00 | 21.36 | O |
| ATOM | 1348 | C | GLU | X | 181 | 27.083 | 57.106 | 44.072 | 1.00 | 16.79 | C |
| ATOM | 1349 | O | GLU | X | 181 | 28.018 | 57.200 | 43.282 | 1.00 | 16.37 | O |
| ATOM | 1350 | N | VAL | X | 182 | 26.053 | 57.948 | 44.081 | 1.00 | 16.86 | N |
| ATOM | 1351 | CA | VAL | X | 182 | 26.052 | 59.152 | 43.238 | 1.00 | 17.35 | C |
| ATOM | 1352 | CB | VAL | X | 182 | 24.693 | 59.895 | 43.286 | 1.00 | 17.24 | C |
| ATOM | 1353 | CG1 | VAL | X | 182 | 24.818 | 61.300 | 42.706 | 1.00 | 17.18 | C |
| ATOM | 1354 | CG2 | VAL | X | 182 | 23.620 | 59.096 | 42.539 | 1.00 | 17.12 | C |
| ATOM | 1355 | C | VAL | X | 182 | 27.208 | 60.069 | 43.660 | 1.00 | 17.37 | C |
| ATOM | 1356 | O | VAL | X | 182 | 28.003 | 60.501 | 42.827 | 1.00 | 16.87 | O |
| ATOM | 1357 | N | LEU | X | 183 | 27.306 | 60.326 | 44.961 | 1.00 | 18.04 | N |
| ATOM | 1358 | CA | LEU | X | 183 | 28.365 | 61.177 | 45.520 | 1.00 | 19.17 | C |
| ATOM | 1359 | CB | LEU | X | 183 | 28.119 | 61.446 | 47.008 | 1.00 | 18.96 | C |
| ATOM | 1360 | CG | LEU | X | 183 | 26.871 | 62.282 | 47.331 | 1.00 | 19.49 | C |
| ATOM | 1361 | CD1 | LEU | X | 183 | 26.695 | 62.445 | 48.833 | 1.00 | 19.23 | C |
| ATOM | 1362 | CD2 | LEU | X | 183 | 26.911 | 63.650 | 46.633 | 1.00 | 19.34 | C |
| ATOM | 1363 | C | LEU | X | 183 | 29.766 | 60.610 | 45.307 | 1.00 | 19.85 | C |
| ATOM | 1364 | O | LEU | X | 183 | 30.712 | 61.366 | 45.088 | 1.00 | 20.20 | O |
| ATOM | 1365 | N | ARG | X | 184 | 29.895 | 59.286 | 45.379 | 1.00 | 20.45 | N |
| ATOM | 1366 | CA | ARG | X | 184 | 31.168 | 58.630 | 45.093 | 1.00 | 21.70 | C |
| ATOM | 1367 | CB | ARG | X | 184 | 31.134 | 57.155 | 45.504 | 1.00 | 21.78 | C |
| ATOM | 1368 | CG | ARG | X | 184 | 31.334 | 56.918 | 46.995 | 1.00 | 22.18 | C |
| ATOM | 1369 | CD | ARG | X | 184 | 31.159 | 55.442 | 47.339 | 1.00 | 22.57 | C |
| ATOM | 1370 | NE | ARG | X | 184 | 31.547 | 55.136 | 48.715 | 1.00 | 23.68 | N |
| ATOM | 1371 | CZ | ARG | X | 184 | 31.359 | 53.957 | 49.306 | 1.00 | 25.29 | C |
| ATOM | 1372 | NH1 | ARG | X | 184 | 30.769 | 52.958 | 48.651 | 1.00 | 25.15 | N |
| ATOM | 1373 | NH2 | ARG | X | 184 | 31.755 | 53.779 | 50.561 | 1.00 | 26.01 | N |
| ATOM | 1374 | C | ARG | X | 184 | 31.567 | 58.764 | 43.620 | 1.00 | 22.01 | C |
| ATOM | 1375 | O | ARG | X | 184 | 32.728 | 59.025 | 43.308 | 1.00 | 22.30 | O |
| ATOM | 1376 | N | MET | X | 185 | 30.607 | 58.588 | 42.719 | 1.00 | 22.36 | N |
| ATOM | 1377 | CA | MET | X | 185 | 30.887 | 58.685 | 41.288 | 1.00 | 23.07 | C |
| ATOM | 1378 | CB | MET | X | 185 | 29.689 | 58.212 | 40.468 | 1.00 | 22.89 | C |
| ATOM | 1379 | CG | MET | X | 185 | 29.402 | 56.735 | 40.640 | 1.00 | 23.31 | C |
| ATOM | 1380 | SD | MET | X | 185 | 28.182 | 56.149 | 39.465 | 1.00 | 23.73 | S |
| ATOM | 1381 | CE | MET | X | 185 | 28.238 | 54.384 | 39.799 | 1.00 | 22.03 | C |
| ATOM | 1382 | C | MET | X | 185 | 31.304 | 60.098 | 40.886 | 1.00 | 23.37 | C |
| ATOM | 1383 | O | MET | X | 185 | 32.194 | 60.273 | 40.052 | 1.00 | 23.40 | O |
| ATOM | 1384 | N | ARG | X | 186 | 30.674 | 61.091 | 41.511 | 1.00 | 23.70 | N |
| ATOM | 1385 | CA | ARG | X | 186 | 31.020 | 62.503 | 41.327 | 1.00 | 24.39 | C |
| ATOM | 1386 | CB | ARG | X | 186 | 29.917 | 63.390 | 41.908 | 1.00 | 23.94 | C |
| ATOM | 1387 | CG | ARG | X | 186 | 28.626 | 63.399 | 41.099 | 1.00 | 22.89 | C |
| ATOM | 1388 | CD | ARG | X | 186 | 27.633 | 64.341 | 41.727 | 1.00 | 20.94 | C |
| ATOM | 1389 | NE | ARG | X | 186 | 26.332 | 64.337 | 41.062 | 1.00 | 19.69 | N |
| ATOM | 1390 | CZ | ARG | X | 186 | 25.212 | 64.781 | 41.627 | 1.00 | 17.82 | C |
| ATOM | 1391 | NH1 | ARG | X | 186 | 25.233 | 65.239 | 42.874 | 1.00 | 17.83 | N |
| ATOM | 1392 | NH2 | ARG | X | 186 | 24.067 | 64.749 | 40.959 | 1.00 | 15.96 | N |
| ATOM | 1393 | C | ARG | X | 186 | 32.364 | 62.899 | 41.953 | 1.00 | 25.26 | C |
| ATOM | 1394 | O | ARG | X | 186 | 32.916 | 63.951 | 41.625 | 1.00 | 25.21 | O |
| ATOM | 1395 | N | GLY | X | 187 | 32.873 | 62.061 | 42.855 | 1.00 | 26.07 | N |
| ATOM | 1396 | CA | GLY | X | 187 | 34.102 | 62.350 | 43.589 | 1.00 | 27.26 | C |
| ATOM | 1397 | C | GLY | X | 187 | 33.860 | 63.316 | 44.730 | 1.00 | 28.25 | C |
| ATOM | 1398 | O | GLY | X | 187 | 34.797 | 63.950 | 45.216 | 1.00 | 28.55 | O |
| ATOM | 1399 | N | THR | X | 188 | 32.599 | 63.435 | 45.147 | 1.00 | 28.80 | N |
| ATOM | 1400 | CA | THR | X | 188 | 32.201 | 64.330 | 46.230 | 1.00 | 29.74 | C |
| ATOM | 1401 | CB | THR | X | 188 | 30.675 | 64.593 | 46.200 | 1.00 | 29.52 | C |
| ATOM | 1402 | OG1 | THR | X | 188 | 30.307 | 65.134 | 44.924 | 1.00 | 29.63 | O |
| ATOM | 1403 | CG2 | THR | X | 188 | 30.250 | 65.564 | 47.302 | 1.00 | 29.67 | C |
| ATOM | 1404 | C | THR | X | 188 | 32.608 | 63.757 | 47.594 | 1.00 | 30.65 | C |
| ATOM | 1405 | O | THR | X | 188 | 32.975 | 64.505 | 48.505 | 1.00 | 30.74 | O |
| ATOM | 1406 | N | ILE | X | 189 | 32.520 | 62.434 | 47.726 | 1.00 | 31.59 | N |
| ATOM | 1407 | CA | ILE | X | 189 | 32.952 | 61.731 | 48.931 | 1.00 | 32.51 | C |
| ATOM | 1408 | CB | ILE | X | 189 | 31.761 | 61.166 | 49.167 | 1.00 | 32.45 | C |
| ATOM | 1409 | CG1 | ILE | X | 189 | 31.003 | 60.074 | 48.991 | 1.00 | 31.89 | C |

APPENDIX 1-continued

X-RAY DATA COORDINATES FOR LRP-220 (SEQ ID NO: 5)

| ATOM | 1410 | CD1 | ILE | X | 189 | 29.990 | 59.295 | 49.824 | 1.00 | 32.04 | C |
|---|---|---|---|---|---|---|---|---|---|---|---|
| ATOM | 1411 | CG2 | ILE | X | 189 | 30.842 | 62.298 | 50.244 | 1.00 | 32.02 | C |
| ATOM | 1412 | C | ILE | X | 189 | 33.905 | 60.600 | 48.565 | 1.00 | 33.74 | C |
| ATOM | 1413 | O | ILE | X | 189 | 33.996 | 60.200 | 47.401 | 1.00 | 33.49 | O |
| ATOM | 1414 | N | SER | X | 190 | 34.603 | 60.088 | 49.573 | 1.00 | 35.56 | N |
| ATOM | 1415 | CA | SER | X | 190 | 35.582 | 59.020 | 49.393 | 1.00 | 37.44 | C |
| ATOM | 1416 | CB | SER | X | 190 | 36.366 | 58.788 | 50.685 | 1.00 | 37.26 | C |
| ATOM | 1417 | OG | SER | X | 190 | 37.180 | 57.630 | 50.578 | 1.00 | 38.17 | O |
| ATOM | 1418 | C | SER | X | 190 | 34.957 | 57.707 | 48.924 | 1.00 | 38.68 | C |
| ATOM | 1419 | O | SER | X | 190 | 33.913 | 57.274 | 49.425 | 1.00 | 38.89 | O |
| ATOM | 1420 | N | ARG | X | 191 | 35.636 | 57.078 | 47.972 | 1.00 | 40.35 | N |
| ATOM | 1421 | CA | ARG | X | 191 | 35.216 | 55.820 | 47.375 | 1.00 | 42.05 | C |
| ATOM | 1422 | CB | ARG | X | 191 | 35.837 | 55.712 | 45.981 | 1.00 | 42.21 | C |
| ATOM | 1423 | CG | ARG | X | 191 | 34.941 | 55.114 | 44.924 | 1.00 | 43.86 | C |
| ATOM | 1424 | CD | ARG | X | 191 | 35.428 | 55.482 | 43.524 | 1.00 | 46.98 | C |
| ATOM | 1425 | NE | ARG | X | 191 | 35.514 | 56.931 | 43.320 | 1.00 | 48.37 | N |
| ATOM | 1426 | CZ | ARG | X | 191 | 35.511 | 57.530 | 42.130 | 1.00 | 49.47 | C |
| ATOM | 1427 | NH1 | ARG | X | 191 | 35.419 | 56.812 | 41.016 | 1.00 | 49.92 | N |
| ATOM | 1428 | NH2 | ARG | X | 191 | 35.593 | 58.854 | 42.052 | 1.00 | 49.66 | N |
| ATOM | 1429 | C | ARG | X | 191 | 35.660 | 54.631 | 48.235 | 1.00 | 42.95 | C |
| ATOM | 1430 | O | ARG | X | 191 | 35.143 | 53.517 | 48.087 | 1.00 | 43.12 | O |
| ATOM | 1431 | N | GLU | X | 192 | 36.612 | 54.876 | 49.136 | 1.00 | 44.02 | N |
| ATOM | 1432 | CA | GLU | X | 192 | 37.237 | 53.805 | 49.920 | 1.00 | 45.03 | C |
| ATOM | 1433 | CB | GLU | X | 192 | 38.759 | 53.997 | 49.991 | 1.00 | 45.27 | C |
| ATOM | 1434 | CG | GLU | X | 192 | 39.514 | 53.573 | 48.722 | 1.00 | 46.86 | C |
| ATOM | 1435 | CD | GLU | X | 192 | 39.505 | 54.633 | 47.619 | 1.00 | 49.21 | C |
| ATOM | 1436 | OE1 | GLU | X | 192 | 39.390 | 55.841 | 47.937 | 1.00 | 50.44 | O |
| ATOM | 1437 | OE2 | GLU | X | 192 | 39.622 | 54.257 | 46.429 | 1.00 | 49.88 | O |
| ATOM | 1438 | C | GLU | X | 192 | 36.641 | 53.590 | 51.320 | 1.00 | 45.20 | C |
| ATOM | 1439 | O | GLU | X | 192 | 36.235 | 52.469 | 51.649 | 1.00 | 45.52 | O |
| ATOM | 1440 | N | HIS | X | 193 | 36.589 | 54.647 | 52.136 | 1.00 | 45.32 | N |
| ATOM | 1441 | CA | HIS | X | 193 | 36.067 | 54.530 | 53.508 | 1.00 | 45.33 | C |
| ATOM | 1442 | CB | HIS | X | 193 | 36.903 | 55.343 | 54.519 | 1.00 | 45.76 | C |
| ATOM | 1443 | CG | HIS | X | 193 | 36.728 | 56.830 | 54.423 | 1.00 | 47.14 | C |
| ATOM | 1444 | ND1 | HIS | X | 193 | 35.675 | 57.498 | 55.014 | 1.00 | 48.11 | N |
| ATOM | 1445 | CE1 | HIS | X | 193 | 35.788 | 58.794 | 54.777 | 1.00 | 48.61 | C |
| ATOM | 1446 | NE2 | HIS | X | 193 | 36.886 | 58.994 | 54.069 | 1.00 | 48.65 | N |
| ATOM | 1447 | CD2 | HIS | X | 193 | 37.496 | 57.783 | 53.841 | 1.00 | 48.49 | C |
| ATOM | 1448 | C | HIS | X | 193 | 34.567 | 54.847 | 53.617 | 1.00 | 44.88 | C |
| ATOM | 1449 | O | HIS | X | 193 | 34.028 | 55.576 | 52.779 | 1.00 | 44.95 | O |
| ATOM | 1450 | N | PRO | X | 194 | 33.887 | 54.274 | 54.636 | 1.00 | 44.30 | N |
| ATOM | 1451 | CA | PRO | X | 194 | 32.461 | 54.508 | 54.881 | 1.00 | 43.71 | C |
| ATOM | 1452 | CB | PRO | X | 194 | 32.249 | 53.908 | 56.272 | 1.00 | 43.81 | C |
| ATOM | 1453 | CG | PRO | X | 194 | 33.240 | 52.809 | 56.343 | 1.00 | 44.02 | C |
| ATOM | 1454 | CD | PRO | X | 194 | 34.451 | 53.324 | 55.618 | 1.00 | 44.29 | C |
| ATOM | 1455 | C | PRO | X | 194 | 32.061 | 55.984 | 54.885 | 1.00 | 43.07 | C |
| ATOM | 1456 | O | PRO | X | 194 | 32.853 | 56.846 | 55.277 | 1.00 | 42.96 | O |
| ATOM | 1457 | N | TRP | X | 195 | 30.830 | 56.245 | 54.451 | 1.00 | 42.19 | N |
| ATOM | 1458 | CA | TRP | X | 195 | 30.264 | 57.590 | 54.380 | 1.00 | 41.46 | C |
| ATOM | 1459 | CB | TRP | X | 195 | 29.054 | 57.583 | 53.433 | 1.00 | 40.37 | C |
| ATOM | 1460 | CG | TRP | X | 195 | 28.438 | 58.928 | 53.110 | 1.00 | 39.32 | C |
| ATOM | 1461 | CD1 | TRP | X | 195 | 29.039 | 60.156 | 53.173 | 1.00 | 38.23 | C |
| ATOM | 1462 | NE1 | TRP | X | 195 | 28.158 | 61.139 | 52.781 | 1.00 | 37.52 | N |
| ATOM | 1463 | CE2 | TRP | X | 195 | 26.967 | 60.557 | 52.435 | 1.00 | 37.76 | C |
| ATOM | 1464 | CD2 | TRP | X | 195 | 27.107 | 59.162 | 52.619 | 1.00 | 38.28 | C |
| ATOM | 1465 | CE3 | TRP | X | 195 | 26.015 | 58.329 | 52.333 | 1.00 | 37.46 | C |
| ATOM | 1466 | CZ3 | TRP | X | 195 | 24.833 | 58.907 | 51.875 | 1.00 | 37.85 | C |
| ATOM | 1467 | CH2 | TRP | X | 195 | 24.728 | 60.297 | 51.701 | 1.00 | 38.37 | C |
| ATOM | 1468 | CZ2 | TRP | X | 195 | 25.780 | 61.137 | 51.975 | 1.00 | 38.03 | C |
| ATOM | 1469 | C | TRP | X | 195 | 29.864 | 58.091 | 55.767 | 1.00 | 41.67 | C |
| ATOM | 1470 | O | TRP | X | 195 | 29.347 | 57.324 | 56.584 | 1.00 | 41.85 | O |
| ATOM | 1471 | N | GLU | X | 196 | 30.110 | 59.381 | 56.007 | 1.00 | 41.79 | N |
| ATOM | 1472 | CA | GLU | X | 196 | 29.788 | 60.068 | 57.265 | 1.00 | 41.88 | C |
| ATOM | 1473 | CB | GLU | X | 196 | 30.214 | 61.548 | 57.171 | 1.00 | 42.20 | C |
| ATOM | 1474 | CG | GLU | X | 196 | 29.283 | 62.434 | 56.318 | 1.00 | 43.93 | C |
| ATOM | 1475 | CD | GLU | X | 196 | 30.009 | 63.428 | 55.412 | 1.00 | 45.98 | C |
| ATOM | 1476 | OE1 | GLU | X | 196 | 29.649 | 64.627 | 55.450 | 1.00 | 46.79 | O |
| ATOM | 1477 | OE2 | GLU | X | 196 | 30.917 | 63.018 | 54.650 | 1.00 | 46.73 | O |
| ATOM | 1478 | C | GLU | X | 196 | 28.308 | 59.950 | 57.673 | 1.00 | 41.33 | C |
| ATOM | 1479 | O | GLU | X | 196 | 27.996 | 59.714 | 58.843 | 1.00 | 41.42 | O |
| ATOM | 1480 | N | VAL | X | 197 | 27.414 | 60.110 | 56.697 | 1.00 | 40.67 | N |
| ATOM | 1481 | CA | VAL | X | 197 | 25.964 | 60.085 | 56.908 | 1.00 | 39.71 | C |
| ATOM | 1482 | CB | VAL | X | 197 | 25.214 | 60.688 | 55.683 | 1.00 | 39.76 | C |
| ATOM | 1483 | CG1 | VAL | X | 197 | 23.701 | 60.599 | 55.846 | 1.00 | 39.02 | C |
| ATOM | 1484 | CG2 | VAL | X | 197 | 25.642 | 62.136 | 55.458 | 1.00 | 39.49 | C |
| ATOM | 1485 | C | VAL | X | 197 | 25.484 | 58.661 | 57.190 | 1.00 | 39.35 | C |
| ATOM | 1486 | O | VAL | X | 198 | 25.827 | 57.727 | 56.462 | 1.00 | 39.19 | O |
| ATOM | 1487 | N | MET | X | 198 | 24.710 | 58.510 | 58.264 | 1.00 | 38.79 | N |

APPENDIX 1-continued

X-RAY DATA COORDINATES FOR LRP-220 (SEQ ID NO: 5)

| ATOM | 1488 | CA | MET | X | 198 | 24.122 | 57.228 | 58.643 | 1.00 | 38.71 | C |
|---|---|---|---|---|---|---|---|---|---|---|---|
| ATOM | 1489 | CB | MET | X | 198 | 23.902 | 57.156 | 60.157 | 1.00 | 38.67 | C |
| ATOM | 1490 | CG | MET | X | 198 | 25.182 | 57.054 | 60.988 | 1.00 | 40.04 | C |
| ATOM | 1491 | SD | MET | X | 198 | 24.856 | 56.740 | 62.744 | 1.00 | 42.11 | S |
| ATOM | 1492 | CE | MET | X | 198 | 23.934 | 58.216 | 63.213 | 1.00 | 41.75 | C |
| ATOM | 1493 | C | MET | X | 198 | 22.794 | 56.993 | 57.923 | 1.00 | 37.14 | C |
| ATOM | 1494 | O | MET | X | 198 | 22.029 | 57.938 | 57.715 | 1.00 | 36.78 | O |
| ATOM | 1495 | N | PRO | X | 199 | 22.521 | 55.731 | 57.531 | 1.00 | 36.06 | N |
| ATOM | 1496 | CA | PRO | X | 199 | 21.247 | 55.353 | 56.915 | 1.00 | 35.29 | C |
| ATOM | 1497 | CB | PRO | X | 199 | 21.331 | 53.825 | 56.857 | 1.00 | 35.14 | C |
| ATOM | 1498 | CG | PRO | X | 199 | 22.786 | 53.549 | 56.744 | 1.00 | 35.18 | C |
| ATOM | 1499 | CD | PRO | X | 199 | 23.446 | 54.583 | 57.606 | 1.00 | 35.80 | C |
| ATOM | 1500 | C | PRO | X | 199 | 19.997 | 55.795 | 57.683 | 1.00 | 34.70 | C |
| ATOM | 1501 | O | PRO | X | 199 | 19.013 | 56.175 | 57.053 | 1.00 | 34.06 | O |
| ATOM | 1502 | N | ASP | X | 200 | 20.038 | 55.759 | 59.017 | 1.00 | 34.37 | N |
| ATOM | 1503 | CA | ASP | X | 200 | 18.851 | 56.064 | 59.835 | 1.00 | 34.36 | C |
| ATOM | 1504 | CB | ASP | X | 200 | 19.066 | 55.719 | 61.323 | 1.00 | 34.77 | C |
| ATOM | 1505 | CG | ASP | X | 200 | 20.318 | 56.353 | 61.908 | 1.00 | 35.96 | C |
| ATOM | 1506 | OD1 | ASP | X | 200 | 20.520 | 57.578 | 61.757 | 1.00 | 36.32 | O |
| ATOM | 1507 | OD2 | ASP | X | 200 | 21.100 | 55.614 | 62.546 | 1.00 | 38.55 | O |
| ATOM | 1508 | C | ASP | X | 200 | 18.294 | 57.484 | 59.661 | 1.00 | 33.81 | C |
| ATOM | 1509 | O | ASP | X | 200 | 17.142 | 57.752 | 60.012 | 1.00 | 33.78 | O |
| ATOM | 1510 | N | LEU | X | 201 | 19.107 | 58.379 | 59.104 | 1.00 | 33.23 | N |
| ATOM | 1511 | CA | LEU | X | 201 | 18.654 | 59.721 | 58.732 | 1.00 | 32.90 | C |
| ATOM | 1512 | CB | LEU | X | 201 | 19.855 | 60.602 | 58.351 | 1.00 | 33.14 | C |
| ATOM | 1513 | CG | LEU | X | 201 | 20.646 | 61.383 | 59.424 | 1.00 | 33.94 | C |
| ATOM | 1514 | CD1 | LEU | X | 201 | 20.907 | 60.605 | 60.718 | 1.00 | 34.33 | C |
| ATOM | 1515 | CD2 | LEU | X | 201 | 21.965 | 61.886 | 58.857 | 1.00 | 33.61 | C |
| ATOM | 1516 | C | LEU | X | 201 | 17.622 | 59.679 | 57.595 | 1.00 | 32.28 | C |
| ATOM | 1517 | O | LEU | X | 201 | 16.834 | 60.608 | 57.430 | 1.00 | 32.29 | O |
| ATOM | 1518 | N | TYR | X | 202 | 17.622 | 58.587 | 56.832 | 1.00 | 31.44 | N |
| ATOM | 1519 | CA | TYR | X | 202 | 16.721 | 58.410 | 55.688 | 1.00 | 30.77 | C |
| ATOM | 1520 | CB | TYR | X | 202 | 17.450 | 57.674 | 54.556 | 1.00 | 29.63 | C |
| ATOM | 1521 | CG | TYR | X | 202 | 18.407 | 58.530 | 53.759 | 1.00 | 28.57 | C |
| ATOM | 1522 | CD1 | TYR | X | 202 | 19.514 | 59.133 | 54.361 | 1.00 | 27.58 | C |
| ATOM | 1523 | CE1 | TYR | X | 202 | 20.389 | 59.925 | 53.628 | 1.00 | 26.51 | C |
| ATOM | 1524 | CZ | TYR | X | 202 | 20.170 | 60.107 | 52.273 | 1.00 | 27.26 | C |
| ATOM | 1525 | OH | TYR | X | 202 | 21.036 | 60.880 | 51.539 | 1.00 | 27.46 | O |
| ATOM | 1526 | CE2 | TYR | X | 202 | 19.087 | 59.516 | 51.650 | 1.00 | 26.92 | C |
| ATOM | 1527 | CD2 | TYR | X | 202 | 18.212 | 58.732 | 52.392 | 1.00 | 27.09 | C |
| ATOM | 1528 | C | TYR | X | 202 | 15.430 | 57.664 | 56.044 | 1.00 | 31.15 | C |
| ATOM | 1529 | O | TYR | X | 202 | 14.497 | 57.616 | 55.235 | 1.00 | 30.65 | O |
| ATOM | 1530 | N | PHE | X | 203 | 15.377 | 57.096 | 57.251 | 1.00 | 32.02 | N |
| ATOM | 1531 | CA | PHE | X | 203 | 14.262 | 56.229 | 57.657 | 1.00 | 33.09 | C |
| ATOM | 1532 | CB | PHE | X | 203 | 14.651 | 55.269 | 58.802 | 1.00 | 32.95 | C |
| ATOM | 1533 | CG | PHE | X | 203 | 15.769 | 54.303 | 58.475 | 1.00 | 32.93 | C |
| ATOM | 1534 | CD1 | PHE | X | 203 | 16.303 | 54.202 | 57.193 | 1.00 | 32.79 | C |
| ATOM | 1535 | CE1 | PHE | X | 203 | 17.332 | 53.303 | 56.917 | 1.00 | 33.35 | C |
| ATOM | 1536 | CZ | PHE | X | 203 | 17.828 | 52.472 | 57.930 | 1.00 | 33.35 | C |
| ATOM | 1537 | CE2 | PHE | X | 203 | 17.300 | 52.556 | 59.206 | 1.00 | 33.16 | C |
| ATOM | 1538 | CD2 | PHE | X | 203 | 16.271 | 53.465 | 59.472 | 1.00 | 33.62 | C |
| ATOM | 1539 | C | PHE | X | 203 | 13.031 | 57.012 | 58.096 | 1.00 | 33.78 | C |
| ATOM | 1540 | O | PHE | X | 203 | 13.129 | 57.957 | 58.876 | 1.00 | 33.94 | O |
| ATOM | 1541 | N | TYR | X | 204 | 11.875 | 56.599 | 57.593 | 1.00 | 34.96 | N |
| ATOM | 1542 | CA | TYR | X | 204 | 10.591 | 57.032 | 58.124 | 1.00 | 36.43 | C |
| ATOM | 1543 | CB | TYR | X | 204 | 9.480 | 56.775 | 57.103 | 1.00 | 36.63 | C |
| ATOM | 1544 | CG | TYR | X | 204 | 8.075 | 56.885 | 57.662 | 1.00 | 36.91 | C |
| ATOM | 1545 | CD1 | TYR | X | 204 | 7.522 | 58.126 | 57.975 | 1.00 | 36.88 | C |
| ATOM | 1546 | CE1 | TYR | X | 204 | 6.231 | 58.232 | 58.487 | 1.00 | 37.29 | C |
| ATOM | 1547 | CZ | TYR | X | 204 | 5.483 | 57.084 | 58.685 | 1.00 | 37.32 | C |
| ATOM | 1548 | OH | TYR | X | 204 | 4.210 | 57.181 | 59.193 | 1.00 | 37.95 | O |
| ATOM | 1549 | CE2 | TYR | X | 204 | 6.007 | 55.838 | 58.378 | 1.00 | 37.62 | C |
| ATOM | 1550 | CD2 | TYR | X | 204 | 7.296 | 55.745 | 57.866 | 1.00 | 31.39 | C |
| ATOM | 1551 | C | TYR | X | 204 | 10.312 | 56.254 | 59.407 | 1.00 | 37.42 | C |
| ATOM | 1552 | O | TYR | X | 204 | 10.431 | 55.024 | 59.434 | 1.00 | 37.79 | O |
| ATOM | 1553 | N | ARG | X | 205 | 9.940 | 56.968 | 60.465 | 1.00 | 38.43 | N |
| ATOM | 1554 | CA | ARG | X | 205 | 9.665 | 56.348 | 61.767 | 1.00 | 39.46 | C |
| ATOM | 1555 | CB | ARG | X | 205 | 9.767 | 57.378 | 62.901 | 1.00 | 39.76 | C |
| ATOM | 1556 | CG | ARG | X | 205 | 11.014 | 58.268 | 62.864 | 1.00 | 41.74 | C |
| ATOM | 1557 | CD | ARG | X | 205 | 10.913 | 59.357 | 61.791 | 1.00 | 44.07 | C |
| ATOM | 1558 | NE | ARG | X | 205 | 12.076 | 60.240 | 61.801 | 1.00 | 46.72 | N |
| ATOM | 1559 | CZ | ARG | X | 205 | 12.019 | 61.562 | 61.939 | 1.00 | 48.19 | C |
| ATOM | 1560 | NH1 | ARG | X | 205 | 10.848 | 62.179 | 62.064 | 1.00 | 48.90 | N |
| ATOM | 1561 | NH2 | ARG | X | 205 | 13.140 | 62.274 | 61.940 | 1.00 | 49.01 | N |
| ATOM | 1562 | C | ARG | X | 205 | 8.295 | 55.665 | 61.795 | 1.00 | 39.44 | C |
| ATOM | 1563 | O | ARG | X | 205 | 7.258 | 56.324 | 61.900 | 1.00 | 39.65 | O |
| ATOM | 1564 | OW0 | HOH | W | 1 | 17.328 | 30.841 | 41.342 | 1.00 | 13.55 | O |
| ATOM | 1565 | OW0 | HOH | W | 2 | 6.080 | 55.905 | 47.160 | 1.00 | 13.76 | O |

APPENDIX 1-continued

X-RAY DATA COORDINATES FOR LRP-220 (SEQ ID NO: 5)

| ATOM | 1566 | OW0 | HOH | W | 3 | 4.048 | 59.906 | 43.347 | 1.00 | 14.05 | O |
|---|---|---|---|---|---|---|---|---|---|---|---|
| ATOM | 1567 | OW0 | HOH | W | 4 | 0.704 | 57.513 | 41.713 | 1.00 | 15.24 | O |
| ATOM | 1568 | OW0 | HOH | W | 5 | 5.651 | 50.433 | 35.931 | 1.00 | 17.32 | O |
| ATOM | 1569 | OW0 | HOH | W | 6 | 23.026 | 64.481 | 38.188 | 1.00 | 10.96 | O |
| ATOM | 1570 | OW0 | HOH | W | 7 | 12.555 | 37.870 | 34.182 | 1.00 | 19.82 | O |
| ATOM | 1571 | OW0 | HOH | W | 8 | 11.922 | 54.852 | 55.497 | 1.00 | 18.27 | O |
| ATOM | 1572 | OW0 | HOH | W | 9 | 8.818 | 43.207 | 50.381 | 1.00 | 14.96 | O |
| ATOM | 1573 | OW0 | HOH | W | 10 | 27.800 | 66.142 | 44.438 | 1.00 | 26.20 | O |
| ATOM | 1574 | OW0 | HOH | W | 11 | 11.787 | 57.813 | 54.420 | 1.00 | 19.92 | O |
| ATOM | 1575 | OW0 | HOH | W | 12 | 3.596 | 40.091 | 46.527 | 1.00 | 22.31 | O |
| ATOM | 1576 | OW0 | HOH | W | 13 | 29.206 | 53.589 | 53.969 | 1.00 | 21.19 | O |
| ATOM | 1577 | OW0 | HOH | W | 14 | 3.076 | 67.750 | 41.467 | 1.00 | 22.33 | O |
| ATOM | 1578 | OW0 | HOH | W | 15 | 26.620 | 64.484 | 38.091 | 1.00 | 17.05 | O |
| ATOM | 1579 | OW0 | HOH | W | 16 | 19.359 | 34.768 | 41.035 | 1.00 | 15.57 | O |
| ATOM | 1580 | OW0 | HOH | W | 17 | 21.010 | 64.857 | 40.624 | 1.00 | 16.67 | O |
| ATOM | 1581 | OW0 | HOH | W | 18 | 19.888 | 36.931 | 39.432 | 1.00 | 23.52 | O |
| ATOM | 1582 | OW0 | HOH | W | 19 | 27.622 | 58.662 | 34.483 | 1.00 | 19.48 | O |
| ATOM | 1583 | OW0 | HOH | W | 20 | 12.579 | 47.128 | 55.855 | 1.00 | 16.64 | O |
| ATOM | 1584 | OW0 | HOH | W | 21 | 5.023 | 62.006 | 44.777 | 1.00 | 17.04 | O |
| ATOM | 1585 | OW0 | HOH | W | 22 | 12.419 | 69.310 | 25.291 | 1.00 | 22.84 | O |
| ATOM | 1586 | OW0 | HOH | W | 23 | 18.045 | 48.671 | 59.395 | 1.00 | 34.19 | O |
| ATOM | 1587 | OW0 | HOH | W | 24 | 21.204 | 72.606 | 40.012 | 1.00 | 19.76 | O |
| ATOM | 1588 | OW0 | HOH | W | 25 | 8.025 | 55.157 | 31.622 | 1.00 | 19.49 | O |
| ATOM | 1589 | OW0 | HOH | W | 26 | 21.198 | 59.382 | 32.295 | 1.00 | 16.12 | O |
| ATOM | 1590 | OW0 | HOH | W | 27 | 26.059 | 47.843 | 37.230 | 1.00 | 20.06 | O |
| ATOM | 1591 | OW0 | HOH | W | 28 | 23.148 | 42.497 | 59.773 | 1.00 | 20.86 | O |
| ATOM | 1592 | OW0 | HOH | W | 29 | 15.204 | 68.185 | 50.111 | 1.00 | 23.32 | O |
| ATOM | 1593 | OW0 | HOH | W | 30 | 13.652 | 67.881 | 37.933 | 1.00 | 24.96 | O |
| ATOM | 1594 | OW0 | HOH | W | 31 | 7.882 | 66.774 | 31.839 | 1.00 | 28.46 | O |
| ATOM | 1595 | OW0 | HOH | W | 32 | 20.646 | 71.206 | 42.370 | 1.00 | 16.13 | O |
| ATOM | 1596 | OW0 | HOH | W | 33 | 28.643 | 37.966 | 50.225 | 1.00 | 34.91 | O |
| ATOM | 1597 | OW0 | HOH | W | 34 | 9.845 | 56.350 | 30.277 | 1.00 | 20.05 | O |
| ATOM | 1598 | OW0 | HOH | W | 35 | 28.649 | 40.248 | 55.059 | 1.00 | 23.37 | O |
| ATOM | 1599 | OW0 | HOH | W | 36 | 8.995 | 59.883 | 55.595 | 1.00 | 35.28 | O |
| ATOM | 1600 | OW0 | HOH | W | 37 | 9.497 | 44.727 | 54.972 | 1.00 | 27.65 | O |
| ATOM | 1601 | OW0 | HOH | W | 38 | 3.544 | 51.694 | 37.348 | 1.00 | 19.23 | O |
| ATOM | 1602 | OW0 | HOH | W | 39 | 8.560 | 64.565 | 24.883 | 1.00 | 36.70 | O |
| ATOM | 1603 | OW0 | HOH | W | 40 | 7.634 | 78.032 | 23.865 | 1.00 | 79.88 | O |
| ATOM | 1604 | OW0 | HOH | W | 41 | 28.072 | 34.958 | 45.439 | 1.00 | 29.28 | O |
| ATOM | 1605 | OW0 | HOH | W | 42 | 5.695 | 48.163 | 44.053 | 1.00 | 23.93 | O |
| ATOM | 1606 | OW0 | HOH | W | 43 | 3.718 | 38.814 | 35.388 | 1.00 | 28.41 | O |
| ATOM | 1607 | OW0 | HOH | W | 44 | 7.063 | 67.338 | 24.804 | 0.50 | 44.82 | O |
| ATOM | 1608 | OW0 | HOH | W | 45 | 23.810 | 53.672 | 33.588 | 1.00 | 20.53 | O |
| ATOM | 1609 | OW0 | HOH | W | 46 | 25.722 | 66.756 | 37.670 | 1.00 | 21.69 | O |
| ATOM | 1610 | OW0 | HOH | W | 47 | 22.474 | 43.283 | 37.008 | 1.00 | 31.52 | O |
| ATOM | 1611 | OW0 | HOH | W | 48 | 1.425 | 57.265 | 52.722 | 1.00 | 36.34 | O |
| ATOM | 1612 | OW0 | HOH | W | 49 | 11.169 | 64.598 | 28.922 | 1.00 | 28.96 | O |
| ATOM | 1613 | OW0 | HOH | W | 50 | 34.865 | 61.830 | 51.709 | 1.00 | 29.19 | O |
| ATOM | 1614 | OW0 | HOH | W | 51 | 20.529 | 48.485 | 57.562 | 1.00 | 24.13 | O |
| ATOM | 1615 | OW0 | HOH | W | 52 | 24.623 | 55.853 | 32.317 | 1.00 | 20.99 | O |
| ATOM | 1616 | OW0 | HOH | W | 53 | 18.317 | 47.805 | 33.566 | 1.00 | 28.59 | O |
| ATOM | 1617 | OW0 | HOH | W | 54 | 12.895 | 50.563 | 28.740 | 1.00 | 28.50 | O |
| ATOM | 1618 | OW0 | HOH | W | 55 | −6.406 | 62.362 | 36.578 | 1.00 | 29.56 | O |
| ATOM | 1619 | OW0 | HOH | W | 56 | 9.486 | 71.154 | 31.652 | 1.00 | 30.54 | O |
| ATOM | 1620 | OW0 | HOH | W | 57 | 4.077 | 66.859 | 46.968 | 1.00 | 23.74 | O |
| ATOM | 1621 | OW0 | HOH | W | 58 | 6.314 | 42.630 | 49.426 | 1.00 | 38.02 | O |
| ATOM | 1622 | OW0 | HOH | W | 59 | 7.069 | 33.565 | 57.902 | 1.00 | 33.17 | O |
| ATOM | 1623 | OW0 | HOH | W | 60 | 10.022 | 65.589 | 31.172 | 1.00 | 25.32 | O |
| ATOM | 1624 | OW0 | HOH | W | 61 | −4.508 | 58.652 | 36.641 | 1.00 | 25.95 | O |
| ATOM | 1625 | OW0 | HOH | W | 62 | 1.246 | 50.368 | 36.771 | 1.00 | 23.12 | O |
| ATOM | 1626 | OW0 | HOH | W | 63 | 18.779 | 58.847 | 31.608 | 1.00 | 22.18 | O |
| ATOM | 1627 | OW0 | HOH | W | 64 | 10.843 | 63.364 | 23.031 | 1.00 | 32.27 | O |
| ATOM | 1628 | OW0 | HOH | W | 65 | 20.715 | 62.939 | 42.136 | 1.00 | 29.55 | O |
| ATOM | 1629 | OW0 | HOH | W | 66 | 0.328 | 69.253 | 45.663 | 1.00 | 51.19 | O |
| ATOM | 1630 | OW0 | HOH | W | 67 | 27.567 | 64.900 | 34.385 | 1.00 | 28.74 | O |
| ATOM | 1631 | OW0 | HOH | W | 68 | 39.584 | 55.441 | 52.982 | 1.00 | 56.79 | O |
| ATOM | 1632 | OW0 | HOH | W | 69 | 22.538 | 62.716 | 53.219 | 1.00 | 31.08 | O |
| ATOM | 1633 | OW0 | HOH | W | 70 | 2.632 | 68.395 | 43.791 | 1.00 | 45.23 | O |
| ATOM | 1634 | OW0 | HOH | W | 71 | 13.947 | 35.361 | 33.766 | 1.00 | 28.13 | O |
| ATOM | 1635 | OW0 | HOH | W | 72 | 35.236 | 59.612 | 45.072 | 1.00 | 56.78 | O |
| ATOM | 1636 | OW0 | HOH | W | 73 | 0.229 | 49.559 | 39.212 | 1.00 | 30.20 | O |
| ATOM | 1637 | OW0 | HOH | W | 74 | 0.068 | 61.386 | 44.549 | 1.00 | 33.50 | O |
| ATOM | 1638 | OW0 | HOH | W | 75 | 20.812 | 70.177 | 47.212 | 1.00 | 29.48 | O |
| ATOM | 1639 | OW0 | HOH | W | 76 | 33.222 | 41.166 | 46.547 | 1.00 | 102.49 | O |
| ATOM | 1640 | OW0 | HOH | W | 77 | 32.816 | 57.977 | 51.761 | 1.00 | 40.60 | O |
| ATOM | 1641 | OW0 | HOH | W | 78 | 6.562 | 43.845 | 33.931 | 1.00 | 35.81 | O |
| ATOM | 1642 | OW0 | HOH | W | 79 | 18.456 | 56.610 | 32.498 | 1.00 | 28.33 | O |
| ATOM | 1643 | OW0 | HOH | W | 80 | 27.538 | 69.465 | 35.257 | 1.00 | 32.01 | O |

APPENDIX 1-continued

X-RAY DATA COORDINATES FOR LRP-220 (SEQ ID NO: 5)

| | | | | | | | | | | |
|---|---|---|---|---|---|---|---|---|---|---|
| ATOM | 1644 | OW0 | HOH | W | 81 | 26.080 | 52.220 | 32.438 | 1.00 | 41.15 | O |
| ATOM | 1645 | OW0 | HOH | W | 82 | 27.106 | 47.009 | 58.301 | 1.00 | 34.89 | O |
| ATOM | 1646 | OW0 | HOH | W | 83 | 23.231 | 64.872 | 28.117 | 1.00 | 31.34 | O |
| ATOM | 1647 | OW0 | HOH | W | 84 | 24.934 | 64.631 | 52.680 | 1.00 | 31.24 | O |
| ATOM | 1648 | OW0 | HOH | W | 85 | 3.258 | 42.665 | 38.698 | 1.00 | 31.19 | O |
| ATOM | 1649 | OW0 | HOH | W | 86 | 18.392 | 36.517 | 33.372 | 1.00 | 30.32 | O |
| ATOM | 1650 | OW0 | HOH | W | 87 | 24.722 | 46.488 | 59.681 | 1.00 | 35.45 | O |
| ATOM | 1651 | OW0 | HOH | W | 88 | 16.606 | 65.079 | 28.152 | 1.00 | 29.22 | O |
| ATOM | 1652 | OW0 | HOH | W | 89 | 8.072 | 43.179 | 52.938 | 1.00 | 33.09 | O |
| ATOM | 1653 | OW0 | HOH | W | 90 | −1.402 | 61.539 | 41.769 | 1.00 | 34.63 | O |
| ATOM | 1654 | OW0 | HOH | W | 91 | 34.094 | 43.537 | 51.724 | 1.00 | 38.99 | O |
| ATOM | 1655 | OW0 | HOH | W | 92 | 17.093 | 54.167 | 30.473 | 1.00 | 36.50 | O |
| ATOM | 1656 | OW0 | HOH | W | 93 | 8.340 | 67.613 | 47.745 | 1.00 | 28.60 | O |
| ATOM | 1657 | OW0 | HOH | W | 94 | 6.149 | 52.606 | 56.112 | 1.00 | 37.53 | O |
| ATOM | 1658 | OW0 | HOH | W | 95 | 2.948 | 40.454 | 40.144 | 1.00 | 30.02 | O |
| ATOM | 1659 | OW0 | HOH | W | 96 | 28.110 | 49.723 | 54.553 | 1.00 | 38.42 | O |
| ATOM | 1660 | OW0 | HOH | W | 97 | 22.675 | 57.203 | 31.092 | 1.00 | 29.09 | O |
| ATOM | 1661 | OW0 | HOH | W | 98 | 30.410 | 50.169 | 49.746 | 1.00 | 35.38 | O |
| ATOM | 1662 | OW0 | HOH | W | 99 | 20.420 | 54.974 | 31.004 | 1.00 | 36.31 | O |
| ATOM | 1663 | OW0 | HOH | W | 100 | −4.624 | 67.662 | 37.763 | 1.00 | 29.29 | O |
| ATOM | 1664 | OW0 | HOH | W | 101 | 32.903 | 59.925 | 53.842 | 1.00 | 57.65 | O |
| ATOM | 1665 | OW0 | HOH | W | 102 | 8.251 | 48.921 | 57.957 | 1.00 | 32.56 | O |
| ATOM | 1666 | OW0 | HOH | W | 103 | 9.529 | 69.708 | 43.742 | 1.00 | 34.52 | O |
| ATOM | 1667 | OW0 | HOH | W | 104 | −1.125 | 51.287 | 33.096 | 1.00 | 51.90 | O |
| ATOM | 1668 | OW0 | HOH | W | 105 | 22.008 | 61.060 | 30.191 | 1.00 | 33.62 | O |
| ATOM | 1669 | OW0 | HOH | W | 106 | 7.453 | 59.198 | 61.616 | 1.00 | 70.12 | O |
| ATOM | 1670 | OW0 | HOH | W | 107 | −0.874 | 51.284 | 40.694 | 1.00 | 35.22 | O |
| ATOM | 1671 | OW0 | HOH | W | 108 | 20.943 | 41.645 | 35.526 | 1.00 | 32.26 | O |
| ATOM | 1672 | OW0 | HOH | W | 109 | 5.620 | 70.636 | 25.877 | 1.00 | 61.44 | O |
| ATOM | 1673 | OW0 | HOH | W | 110 | 22.275 | 54.122 | 60.734 | 1.00 | 36.32 | O |
| ATOM | 1674 | OW0 | HOH | W | 111 | 26.307 | 66.084 | 49.785 | 1.00 | 34.11 | O |
| ATOM | 1675 | OW0 | HOH | W | 112 | 11.407 | 48.301 | 58.411 | 1.00 | 29.02 | O |
| ATOM | 1676 | OW0 | HOH | W | 113 | 26.806 | 63.460 | 31.122 | 1.00 | 34.71 | O |
| ATOM | 1677 | OW0 | HOH | W | 114 | 8.884 | 30.582 | 40.992 | 1.00 | 36.30 | O |
| ATOM | 1678 | OW0 | HOH | W | 115 | 11.479 | 63.554 | 59.426 | 1.00 | 56.37 | O |
| ATOM | 1679 | OW0 | HOH | W | 116 | 14.803 | 63.347 | 29.162 | 1.00 | 39.68 | O |
| ATOM | 1680 | OW0 | HOH | W | 117 | 12.150 | 53.474 | 60.742 | 1.00 | 41.19 | O |
| ATOM | 1681 | OW0 | HOH | W | 118 | 28.575 | 47.112 | 48.173 | 1.00 | 34.99 | O |
| ATOM | 1682 | OW0 | HOH | W | 119 | 10.076 | 30.133 | 34.488 | 1.00 | 47.15 | O |
| ATOM | 1683 | OW0 | HOH | W | 120 | 28.402 | 61.033 | 31.016 | 1.00 | 39.73 | O |
| ATOM | 1684 | OW0 | HOH | W | 121 | 25.479 | 67.945 | 46.049 | 1.00 | 39.36 | O |
| ATOM | 1685 | OW0 | HOH | W | 122 | 0.734 | 56.578 | 47.909 | 1.00 | 38.00 | O |
| ATOM | 1686 | OW0 | HOH | W | 123 | 9.395 | 49.839 | 30.508 | 1.00 | 35.16 | O |
| ATOM | 1687 | OW0 | HOH | W | 124 | 31.550 | 49.603 | 47.391 | 1.00 | 32.71 | O |
| ATOM | 1688 | OW0 | HOH | W | 125 | 0.816 | 41.368 | 43.751 | 1.00 | 35.22 | O |
| ATOM | 1689 | OW0 | HOH | W | 126 | 5.486 | 47.377 | 47.613 | 1.00 | 44.89 | O |
| ATOM | 1690 | OW0 | HOH | W | 127 | 31.113 | 51.669 | 45.682 | 1.00 | 38.04 | O |
| ATOM | 1691 | OW0 | HOH | W | 128 | 1.436 | 59.923 | 42.862 | 1.00 | 26.88 | O |
| ATOM | 1692 | OW0 | HOH | W | 129 | 18.586 | 43.366 | 33.846 | 1.00 | 38.47 | O |
| ATOM | 1693 | OW0 | HOH | W | 130 | 16.561 | 69.834 | 48.474 | 1.00 | 32.88 | O |
| ATOM | 1694 | OW0 | HOH | W | 131 | 34.295 | 43.982 | 47.100 | 1.00 | 68.28 | O |
| ATOM | 1695 | OW0 | HOH | W | 132 | 5.298 | 34.689 | 38.229 | 1.00 | 49.39 | O |
| ATOM | 1696 | OW0 | HOH | W | 133 | 3.300 | 35.280 | 40.898 | 1.00 | 35.60 | O |
| ATOM | 1697 | OW0 | HOH | W | 134 | 12.437 | 70.145 | 37.142 | 1.00 | 40.97 | O |
| ATOM | 1698 | OW0 | HOH | W | 135 | 27.766 | 65.255 | 29.010 | 1.00 | 36.38 | O |
| ATOM | 1699 | OW0 | HOH | W | 136 | 6.084 | 41.962 | 46.625 | 1.00 | 47.13 | O |
| ATOM | 1700 | OW0 | HOH | W | 137 | 5.960 | 49.922 | 55.359 | 1.00 | 34.78 | O |
| ATOM | 1701 | OW0 | HOH | W | 138 | 19.695 | 36.565 | 36.333 | 1.00 | 37.61 | O |
| ATOM | 1702 | OW0 | HOH | W | 139 | 26.815 | 55.165 | 58.919 | 1.00 | 61.16 | O |
| ATOM | 1703 | OW0 | HOH | W | 140 | 21.895 | 52.796 | 31.863 | 1.00 | 42.17 | O |
| ATOM | 1704 | OW0 | HOH | W | 141 | 1.460 | 65.803 | 50.346 | 1.00 | 40.26 | O |
| ATOM | 1705 | OW0 | HOH | W | 142 | 4.323 | 46.032 | 44.857 | 1.00 | 37.04 | O |
| ATOM | 1706 | OW0 | HOH | W | 143 | 13.181 | 47.109 | 33.427 | 1.00 | 40.11 | O |
| ATOM | 1707 | OW0 | HOH | W | 144 | 18.021 | 60.476 | 62.244 | 1.00 | 58.10 | O |
| ATOM | 1708 | OW0 | HOH | W | 145 | 34.229 | 42.239 | 57.157 | 1.00 | 45.39 | O |
| ATOM | 1709 | OW0 | HOH | W | 146 | 22.591 | 48.081 | 59.775 | 1.00 | 32.69 | O |
| ATOM | 1710 | OW0 | HOH | W | 147 | 7.290 | 34.657 | 36.557 | 1.00 | 38.37 | O |
| ATOM | 1711 | OW0 | HOH | W | 148 | 30.205 | 51.763 | 38.560 | 1.00 | 43.21 | O |
| ATOM | 1712 | OW0 | HOH | W | 149 | 9.512 | 60.561 | 58.672 | 1.00 | 47.60 | O |
| ATOM | 1713 | OW0 | HOH | W | 150 | 1.012 | 47.871 | 35.078 | 1.00 | 33.28 | O |
| ATOM | 1714 | OW0 | HOH | W | 151 | 28.668 | 53.537 | 56.609 | 1.00 | 43.90 | O |
| ATOM | 1715 | OW0 | HOH | W | 152 | 29.440 | 57.784 | 36.320 | 1.00 | 46.19 | O |
| ATOM | 1716 | OW0 | HOH | W | 153 | 14.716 | 41.521 | 57.984 | 1.00 | 42.10 | O |
| ATOM | 1717 | OW0 | HOH | W | 154 | 2.405 | 29.431 | 51.398 | 1.00 | 54.51 | O |
| ATOM | 1718 | OW0 | HOH | W | 155 | 15.742 | 47.273 | 34.380 | 1.00 | 32.73 | O |
| ATOM | 1719 | OW0 | HOH | W | 156 | −0.872 | 51.922 | 36.097 | 1.00 | 28.11 | O |
| ATOM | 1720 | OW0 | HOH | W | 157 | 31.688 | 65.491 | 39.530 | 1.00 | 39.88 | O |
| ATOM | 1721 | OW0 | HOH | W | 158 | 21.560 | 46.873 | 62.631 | 1.00 | 38.78 | O |

APPENDIX 1-continued

X-RAY DATA COORDINATES FOR LRP-220 (SEQ ID NO: 5)

| ATOM | 1722 | OW0 | HOH | W | 159 | −0.474 | 56.276 | 45.289 | 1.00 | 46.96 | O |
| ATOM | 1723 | OW0 | HOH | W | 160 | 6.427 | 28.246 | 48.315 | 1.00 | 36.54 | O |
| ATOM | 1724 | OW0 | HOH | W | 161 | 31.532 | 37.651 | 51.492 | 1.00 | 56.31 | O |
| ATOM | 1725 | OW0 | HOH | W | 162 | 9.015 | 29.318 | 55.310 | 1.00 | 42.95 | O |
| ATOM | 1726 | OW0 | HOH | W | 163 | 28.298 | 64.095 | 52.742 | 1.00 | 50.08 | O |
| ATOM | 1727 | OW0 | HOH | W | 164 | −0.594 | 60.533 | 46.930 | 1.00 | 41.52 | O |

What is claimed is:

1. A laminin receptor (LamR) crystal comprising residues 1-220 of the full-length human 37 kDa LamR protein, wherein said protein is in the tetragonal spacegroup $P4_32_12$ and has unit cell dimensions of a=75.7 Angstroms, b=75.7 Angstroms and c=99.0 Angstroms.

2. The LamR crystal of claim 1 having atomic structure coordinates listed in Appendix 1, or any part thereof.

3. The LamR crystal of claim 1 having an active site including relative structural coordinates of amino acid residues Leu25, Gly26, Gly27 Ile46, Arg80, Asp126, Arg128, Asn149, Asp151, Ser152, Asp164, Asp165, Lys166, Gln33, Gln35, Tyr36, Lys57, Ala137, Ser138, Asn141, Leu142, Pro143, Thr144, Met10, Leu19, His24, Ile49, Asn50, Leu51, Lys52, Gln9, Lys11, Trp55, Leu59, Glu181, Arg184, Met185 and Arg191, or any portion thereof, and having a root mean square deviation from residue backbone atoms of said amino acid residues of not more than 1.5 Å.

4. The LamR crystal of claim 3, wherein
said active site is complexed with a compound,
said active site includes, relative structural coordinates of amino acid residues: Leu25, Gly26, Gly27, Thr28, Ile46, Asp126, Pro127, Arg128, Ala129, Asn149, Asp151, Ser152, Asn164, Asn165, Lys166, Val15, Phe18, Leu19, His24, Leu25, Ile49, Asn50, Leu51, and Lys52, Arg80 and Asn81, or any portion thereof, and
a root mean square deviation from residue backbone atoms of said amino acid residues being not more than 1.5 Å.

5. The LamR crystal of claim 3, wherein
said active site is complexed with a protein or peptide,
said active site includes relative structural coordinates of amino acid residues: Gln33, Leu60, Arg63, Ala64, Ala67, Asn70, Pro71, Ala72, Asp73, Val74, Ser75, Ala91, Ala92, Ala93, Thr94, Gly95, Ala96, Thr97, Pro98, Ile99, Arg102, Phe103, Thr104, Pro105, Gly106, Thr107, Phe108, Thr109, Asn110, Gln111, Ile112, Gln113, Ala114, Ala115, Phe116, Arg117, Glu118, Pro119, Arg120, Leu121, Leu134, Ala137, Ser138, Asn141, Leu142, Pro143, Thr144, Ile145, Leu154, Arg155, Tyr156, Val157, Asp158, Ile159, Leu183, Arg186, or any portion thereof, and
a root mean square deviation from residue backbone atoms of said amino acid residues being not more than 1.5 Å.

6. The LamR crystal of claim 3, wherein
said active site is complexed with a protein or peptide,
said active site includes relative structural coordinates of amino acid, residues: Ala72, Asp73, Val74, Ser75, Thr97, Ile99, Thr104, Pro105, Gly106, Thr107, Phe108, Asn110, Gln111, Ile112, Gln113, Ala114, Ala115, Phe116, Arg117, Glu118, Pro119, or any portion thereof, and
a root mean square deviation from residue backbone atoms of said amino acid residues being not more than 1.5 Å.

* * * * *